(12) United States Patent
Stevenson et al.

(10) Patent No.: US 8,903,505 B2
(45) Date of Patent: Dec. 2, 2014

(54) IMPLANTABLE LEAD BANDSTOP FILTER EMPLOYING AN INDUCTIVE COIL WITH PARASITIC CAPACITANCE TO ENHANCE MRI COMPATIBILITY OF ACTIVE MEDICAL DEVICES

(75) Inventors: Robert A. Stevenson, Canyon Country, CA (US); Henry R. Halperin, Pikesville, MD (US); Albert C. Lardo, Baldwin, MD (US); Warren S. Dabney, Orchard Park, NY (US); Kishore Kumar Kondabatni, Williamsville, NY (US); Christine A. Frysz, Orchard Park, NY (US); Robert Shawn Johnson, North Tonawanda, NY (US); Holly Noelle Moschiano, Lancaster, NY (US); Barry C. Muffoletto, Alden, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/276,484

(22) Filed: Oct. 19, 2011

(65) Prior Publication Data

US 2012/0071956 A1    Mar. 22, 2012

Related U.S. Application Data

(60) Continuation-in-part of application No. 12/170,811, filed on Jul. 10, 2008, which is a division of application No. 11/423,073, filed on Jun. 8, 2006, now Pat. No. 8,244,370.

(51) Int. Cl.
*A61B 5/055* (2006.01)
*A61N 1/05* (2006.01)
(Continued)

(52) U.S. Cl.
CPC .......... *A61N 1/05* (2013.01); *H03H 2001/005* (2013.01); *A61N 1/3718* (2013.01); *A61B 2019/5236* (2013.01); *A61N 1/0551* (2013.01); *A61B 18/1492* (2013.01); *H03H 2001/0042* (2013.01); *A61B 2018/00839* (2013.01); *H03H 2007/013* (2013.01); *H03H 7/1766* (2013.01); *A61N 2001/086* (2013.01); *A61N 1/056* (2013.01); *H03H 1/0007* (2013.01)
USPC .......................................... 607/116; 600/377

(58) Field of Classification Search
CPC ....... A61N 1/05; A61N 1/056; A61N 1/0551; A61N 1/3718
USPC ................... 607/2, 9; 600/411, 424
See application file for complete search history.

(56) References Cited

U.S. PATENT DOCUMENTS

| | | |
|---|---|---|
| 3,871,382 A | 3/1975 | Mann |
| 3,968,802 A | 7/1976 | Ballis |

(Continued)

FOREIGN PATENT DOCUMENTS

| | | |
|---|---|---|
| EP | 0243573 | 11/1987 |
| EP | 0145430 | 5/1991 |

(Continued)

OTHER PUBLICATIONS

R.S. Johnson, H. Moschiano, R. Stevenson, S. Brainard, S. YE, J.E. Spaulding, and W. Dabney; Characterization of the Relationship between MR-Induced Distal tip Heating in Cardiac Pacing Leads and the Electrical Performance of Novel Filtered Tip Assemblies; 17th Scientific Meeting & Exhibition of the International Society for Magnetic Resonance in Medicine, Honolulu, Hawaii, Apr. 18-24, 2009, p. 307.

(Continued)

*Primary Examiner* — Christopher D Koharski
*Assistant Examiner* — Michael D Abreu
(74) *Attorney, Agent, or Firm* — Michael F. Scalise

(57) ABSTRACT

A medical lead system includes at least one bandstop filter for attenuating current flow through the lead across a range of frequencies. The bandstop filter has an overall circuit Q wherein the resultant 3 dB bandwidth is at least 10 kHz. The values of capacitance and inductance of the bandstop filter are selected such that the bandstop filter is resonant at a selected center frequency or range of frequencies. Preferably, the bandstop filter has an overall circuit Q wherein the resultant 10 dB bandwidth is at least 10 kHz. Such bandstop filters are backwards compatible with known implantable deployment systems and extraction systems.

46 Claims, 27 Drawing Sheets

(51) Int. Cl.
*A61B 18/14* (2006.01)
*H03H 1/00* (2006.01)
*A61N 1/37* (2006.01)
*A61B 19/00* (2006.01)
*A61B 18/00* (2006.01)
*H03H 7/01* (2006.01)
*A61N 1/08* (2006.01)

(56) References Cited

U.S. PATENT DOCUMENTS

| | | |
|---|---|---|
| 4,188,598 A | 2/1980 | Hunt |
| 4,295,467 A | 10/1981 | Mann et al. |
| 4,320,763 A | 3/1982 | Money |
| 4,424,551 A | 1/1984 | Stevenson et al. |
| 4,431,005 A | 2/1984 | McCormick |
| 4,445,501 A | 5/1984 | Bresler |
| 4,572,198 A | 2/1986 | Codrington |
| 4,585,001 A | 4/1986 | Belt |
| 4,633,181 A | 12/1986 | Murphy-Boesch et al. |
| 4,643,186 A | 2/1987 | Rosen et al. |
| 4,654,880 A | 3/1987 | Sontag |
| 4,672,972 A | 6/1987 | Berke |
| 4,689,621 A | 8/1987 | Kleinberg |
| 4,754,752 A | 7/1988 | Ginsburg et al. |
| 4,757,820 A | 7/1988 | Itoh |
| 4,766,381 A | 8/1988 | Conturo et al. |
| 4,799,499 A | 1/1989 | Bisping |
| 4,813,429 A | 3/1989 | Eshel et al. |
| 4,823,812 A | 4/1989 | Eshel et al. |
| 4,832,023 A | 5/1989 | Murphy-Chutorian et al. |
| 4,858,623 A | 8/1989 | Bradshaw et al. |
| 4,859,950 A | 8/1989 | Keren |
| 4,932,411 A | 6/1990 | Fritschy et al. |
| 4,960,106 A | 10/1990 | Kubokawa et al. |
| 4,989,608 A | 2/1991 | Ratner |
| 5,019,075 A | 5/1991 | Spears et al. |
| 5,095,911 A | 3/1992 | Pomeranz |
| 5,099,208 A | 3/1992 | Fitzpatrick et al. |
| 5,167,233 A | 12/1992 | Eberle et al. |
| 5,178,618 A | 1/1993 | Kandarpa |
| 5,190,046 A | 3/1993 | Shturman |
| 5,197,468 A | 3/1993 | Proctor et al. |
| 5,209,233 A * | 5/1993 | Holland et al. ............... 600/412 |
| 5,211,165 A | 5/1993 | Dumoulin et al. |
| 5,217,010 A * | 6/1993 | Tsitlik et al. ..................... 607/9 |
| 5,246,438 A | 9/1993 | Langberg |
| 5,251,120 A | 10/1993 | Smith |
| 5,271,400 A | 12/1993 | Dumoulin et al. |
| 5,300,108 A | 4/1994 | Rebell et al. |
| 5,307,808 A | 5/1994 | Dumoulin et al. |
| 5,307,814 A | 5/1994 | Kressel et al. |
| 5,318,025 A | 6/1994 | Dumoulin et al. |
| 5,323,776 A | 6/1994 | Blakeley et al. |
| 5,323,778 A | 6/1994 | Kandarpa et al. |
| 5,333,095 A | 7/1994 | Stevenson et al. |
| 5,334,045 A | 8/1994 | Cappa et al. |
| 5,334,193 A | 8/1994 | Nardella |
| 5,348,010 A | 9/1994 | Schnall et al. |
| 5,352,979 A | 10/1994 | Conturo |
| 5,358,515 A | 10/1994 | Hurter et al. |
| 5,363,845 A | 11/1994 | Chowdhury et al. |
| 5,365,928 A | 11/1994 | Rhinehart et al. |
| 5,370,644 A | 12/1994 | Langberg |
| 5,398,683 A | 3/1995 | Edwards et al. |
| 5,400,787 A | 3/1995 | Marandos |
| 5,413,104 A | 5/1995 | Buijs et al. |
| 5,419,325 A | 5/1995 | Dumoulin et al. |
| 5,433,717 A | 7/1995 | Rubinsky et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,447,156 A | 9/1995 | Dumoulin et al. |
| 5,451,232 A | 9/1995 | Rinehart et al. |
| 5,462,055 A | 10/1995 | Casey et al. |
| 5,476,095 A | 12/1995 | Becker et al. |
| 5,498,261 A | 3/1996 | Strul |
| 5,507,743 A | 4/1996 | Edwards et al. |
| 5,512,825 A | 4/1996 | Atalar et al. |
| 5,514,173 A | 5/1996 | Rebell et al. |
| 5,540,679 A | 7/1996 | Fram et al. |
| 5,545,201 A | 8/1996 | Helland et al. |
| 5,558,093 A | 9/1996 | Pomeranz |
| 5,578,008 A | 11/1996 | Hara |
| 5,588,432 A | 12/1996 | Crowley |
| 5,590,657 A | 1/1997 | Cain et al. |
| 5,591,218 A | 1/1997 | Jacobson |
| 5,623,241 A | 4/1997 | Minkoff |
| 5,629,622 A | 5/1997 | Scampini |
| 5,662,108 A | 9/1997 | Budd et al. |
| 5,682,897 A | 11/1997 | Pomeranz |
| 5,685,878 A | 11/1997 | Falwell et al. |
| 5,697,958 A | 12/1997 | Paul et al. |
| 5,699,801 A | 12/1997 | Atalar et al. |
| 5,706,810 A | 1/1998 | Rubinsky et al. |
| 5,715,825 A | 2/1998 | Crowley |
| 5,716,390 A | 2/1998 | Li |
| 5,722,998 A | 3/1998 | Prutchi et al. |
| 5,735,887 A | 4/1998 | Barreras et al. |
| 5,741,321 A | 4/1998 | Brennen |
| 5,751,539 A | 5/1998 | Stevenson et al. |
| 5,759,202 A | 6/1998 | Schroeppel |
| 5,769,800 A | 6/1998 | Gelfand et al. |
| 5,772,693 A | 6/1998 | Brownlee |
| 5,775,338 A | 7/1998 | Hastings |
| 5,779,669 A | 7/1998 | Haissaguerre et al. |
| 5,792,055 A | 8/1998 | McKinnon |
| 5,824,029 A | 10/1998 | Weijand et al. |
| 5,833,608 A | 11/1998 | Acker |
| 5,840,031 A | 11/1998 | Crowley |
| 5,864,234 A | 1/1999 | Ludeke |
| 5,868,674 A | 2/1999 | Glowinski et al. |
| 5,879,347 A | 3/1999 | Saadat |
| 5,891,134 A | 4/1999 | Goble et al. |
| 5,905,627 A | 5/1999 | Brendel et al. |
| 5,916,162 A | 6/1999 | Snelten et al. |
| 5,928,145 A | 7/1999 | Ocali et al. |
| 5,928,159 A | 7/1999 | Eggers et al. |
| 5,938,609 A | 8/1999 | Pomeranz |
| 5,938,692 A | 8/1999 | Rudie |
| 5,959,829 A | 9/1999 | Stevenson et al. |
| 5,964,705 A | 10/1999 | Truwit et al. |
| 5,973,906 A | 10/1999 | Stevenson et al. |
| 5,978,204 A | 11/1999 | Stevenson |
| 6,004,269 A | 12/1999 | Crowley et al. |
| 6,008,980 A * | 12/1999 | Stevenson et al. ............. 361/302 |
| 6,011,995 A | 1/2000 | Guglielmi et al. |
| 6,026,316 A | 2/2000 | Kucharczyk et al. |
| 6,027,500 A | 2/2000 | Buckles et al. |
| 6,031,375 A | 2/2000 | Atalar et al. |
| 6,045,532 A | 4/2000 | Eggers et al. |
| 6,055,457 A | 4/2000 | Bonner |
| 6,066,136 A | 5/2000 | Geistert |
| 6,099,524 A | 8/2000 | Lipson et al. |
| 6,101,417 A | 8/2000 | Vogel et al. |
| 6,128,522 A | 10/2000 | Acker et al. |
| 6,129,670 A | 10/2000 | Burdette et al. |
| 6,141,594 A | 10/2000 | Flynn et al. |
| 6,159,560 A | 12/2000 | Stevenson et al. |
| 6,171,240 B1 | 1/2001 | Young et al. |
| 6,171,241 B1 | 1/2001 | McVeigh et al. |
| 6,188,219 B1 | 2/2001 | Reeder et al. |
| 6,226,545 B1 | 5/2001 | Gilderdale |
| 6,236,205 B1 | 5/2001 | Ludeke et al. |
| 6,238,390 B1 | 5/2001 | Tu et al. |
| 6,263,229 B1 | 7/2001 | Atalar et al. |
| 6,272,370 B1 | 8/2001 | Gillies et al. |
| 6,275,369 B1 | 8/2001 | Stevenson et al. |
| 6,280,385 B1 | 8/2001 | Melzer et al. |
| 6,284,971 B1 | 9/2001 | Atalar et al. |
| 6,332,089 B1 | 12/2001 | Acker et al. |
| 6,370,427 B1 | 4/2002 | Alt et al. |
| 6,390,996 B1 | 5/2002 | Halperin et al. |
| 6,408,202 B1 | 6/2002 | Lima et al. |

(56) References Cited

U.S. PATENT DOCUMENTS

| | | |
|---|---|---|
| 6,424,234 B1 | 7/2002 | Stevenson |
| 6,428,537 B1 | 8/2002 | Swanson et al. |
| 6,456,481 B1 | 9/2002 | Stevenson |
| 6,473,291 B1 | 10/2002 | Stevenson |
| 6,493,591 B1 | 12/2002 | Stokes |
| 6,529,103 B1 | 3/2003 | Brendel et al. |
| 6,535,766 B1 | 3/2003 | Thompson et al. |
| 6,539,253 B2 | 3/2003 | Thompson et al. |
| 6,539,261 B2 | 3/2003 | Molin |
| 6,549,800 B1 | 4/2003 | Atalar et al. |
| 6,556,009 B2 | 4/2003 | Kellman et al. |
| 6,566,987 B2 | 5/2003 | Okada et al. |
| 6,567,259 B2 | 5/2003 | Stevenson et al. |
| 6,567,703 B1 | 5/2003 | Thompson et al. |
| 6,593,884 B1 | 7/2003 | Gilboae et al. |
| 6,606,513 B2 | 8/2003 | Lardo et al. |
| 6,628,980 B2 | 9/2003 | Atalar et al. |
| 6,633,780 B1 | 10/2003 | Berger et al. |
| 6,643,903 B2 | 11/2003 | Stevenson et al. |
| 6,654,628 B1 | 11/2003 | Silber et al. |
| 6,675,033 B1 | 1/2004 | Lardo et al. |
| 6,675,779 B2 | 1/2004 | King et al. |
| 6,675,780 B1 | 1/2004 | Wendels et al. |
| 6,687,550 B1 | 2/2004 | Doan |
| 6,690,963 B2 | 2/2004 | Ben-Haim et al. |
| 6,701,176 B1 | 3/2004 | Halperin et al. |
| 6,714,809 B2 | 3/2004 | Lee et al. |
| 6,759,388 B1 | 7/2004 | Marchant et al. |
| 6,765,779 B2 | 7/2004 | Stevenson et al. |
| 6,765,780 B2 | 7/2004 | Brendel et al. |
| 6,771,067 B2 | 8/2004 | Kellman et al. |
| 6,829,509 B1 | 12/2004 | MacDonald et al. |
| 6,847,837 B1 | 1/2005 | Melzer et al. |
| 6,868,288 B2 | 3/2005 | Thompson |
| 6,871,091 B2 | 3/2005 | Wilkinson et al. |
| 6,876,885 B2 | 4/2005 | Swoyer et al. |
| 6,882,248 B2 | 4/2005 | Stevenson et al. |
| 6,896,454 B2 | 5/2005 | Gerhardt et al. |
| 6,898,454 B2 | 5/2005 | Atalar et al. |
| 6,901,292 B2 | 5/2005 | Hrdlicka et al. |
| 6,904,307 B2 | 6/2005 | Karmarkar et al. |
| 6,925,328 B2 | 8/2005 | Foster et al. |
| 6,931,286 B2 | 8/2005 | Sigg et al. |
| 6,944,489 B2 | 9/2005 | Zeijlemaker et al. |
| 6,949,929 B2 | 9/2005 | Gray et al. |
| 6,952,613 B2 | 10/2005 | Swoyer et al. |
| 6,971,391 B1 | 12/2005 | Wang et al. |
| 6,985,347 B2 | 1/2006 | Stevenson et al. |
| 6,985,775 B2 | 1/2006 | Reinke et al. |
| 6,999,818 B2 | 2/2006 | Stevenson et al. |
| 7,013,180 B2 | 3/2006 | Villaseca et al. |
| 7,038,900 B2 | 5/2006 | Stevenson et al. |
| 7,092,766 B1 | 8/2006 | Salys et al. |
| 7,113,387 B2 | 9/2006 | Stevenson et al. |
| 7,149,773 B2 | 12/2006 | Haller et al. |
| 7,155,271 B2 | 12/2006 | Halperin |
| 7,174,219 B2 | 2/2007 | Wahlstrand et al. |
| 7,236,716 B2 | 6/2007 | Ishino et al. |
| 7,276,474 B2 | 10/2007 | Marchant et al. |
| 7,319,905 B1 | 1/2008 | Morgan et al. |
| 7,363,090 B2 | 4/2008 | Halperin |
| 7,422,568 B2 | 9/2008 | Yang et al. |
| 7,899,551 B2 | 3/2011 | Westlund et al. |
| 2002/0055678 A1 | 5/2002 | Scott et al. |
| 2002/0095197 A1 | 7/2002 | Lardo et al. |
| 2002/0177771 A1 | 11/2002 | Guttman et al. |
| 2002/0192688 A1 | 12/2002 | Yang et al. |
| 2003/0028094 A1 | 2/2003 | Kumar et al. |
| 2003/0028095 A1 | 2/2003 | Tulley et al. |
| 2003/0050557 A1 | 3/2003 | Susil et al. |
| 2003/0083726 A1 | 5/2003 | Zeijlemaker et al. |
| 2003/0144720 A1 | 7/2003 | Villaseca et al. |
| 2003/0144721 A1* | 7/2003 | Villaseca et al. ............... 607/122 |
| 2003/0208252 A1 | 11/2003 | O'Boyle et al. |
| 2003/0212373 A1 | 11/2003 | Hall et al. |
| 2004/0015079 A1 | 1/2004 | Berger et al. |
| 2004/0034338 A1 | 2/2004 | Thierfelder et al. |
| 2004/0167392 A1 | 8/2004 | Halperin et al. |
| 2004/0263173 A1* | 12/2004 | Gray ............................ 324/322 |
| 2004/0263174 A1 | 12/2004 | Gray et al. |
| 2005/0070972 A1 | 3/2005 | Wahlstrand et al. |
| 2005/0197677 A1 | 9/2005 | Stevenson |
| 2005/0222658 A1 | 10/2005 | Hoegh et al. |
| 2006/0009819 A1 | 1/2006 | Przybyszewski |
| 2006/0100506 A1 | 5/2006 | Halperin et al. |
| 2006/0211979 A1 | 9/2006 | Smith et al. |
| 2006/0247684 A1 | 11/2006 | Halperin |
| 2007/0112398 A1 | 5/2007 | Stevenson |
| 2007/0167867 A1 | 7/2007 | Wolf |
| 2007/0168005 A1 | 7/2007 | Gray |
| 2007/0255332 A1 | 11/2007 | Cabelka et al. |
| 2008/0049376 A1 | 2/2008 | Stevenson |
| 2008/0071313 A1 | 3/2008 | Stevenson |
| 2008/0116997 A1 | 5/2008 | Dabney |
| 2008/0132987 A1 | 6/2008 | Westlund |
| 2008/0161886 A1 | 7/2008 | Stevenson et al. |
| 2008/0221638 A1 | 9/2008 | Wedan et al. |
| 2008/0262592 A1 | 10/2008 | Jordan et al. |
| 2009/0163980 A1 | 6/2009 | Stevenson |
| 2009/0243756 A1 | 10/2009 | Stevenson et al. |
| 2010/0023095 A1 | 1/2010 | Stevenson et al. |
| 2010/0160989 A1 | 6/2010 | Legay |
| 2010/0217264 A1 | 8/2010 | Odom et al. |
| 2010/0217341 A1 | 8/2010 | John et al. |
| 2010/0234907 A1 | 9/2010 | Dobak, III |
| 2011/0043297 A1 | 2/2011 | Stevenson et al. |

FOREIGN PATENT DOCUMENTS

| | | |
|---|---|---|
| EP | 466424 | 1/1992 |
| EP | 557127 | 8/1993 |
| EP | 0673621 | 9/1995 |
| EP | 0498996 | 3/1997 |
| EP | 0930509 | 12/1998 |
| EP | 1021730 | 4/1999 |
| JP | 60141034 | 7/1985 |
| JP | 61181925 | 8/1985 |
| JP | 62233905 | 10/1987 |
| JP | 4071536 | 3/1992 |
| JP | 6054823 | 3/1994 |
| JP | 6199470902 | 3/1994 |
| JP | 994238 | 4/1997 |
| JP | 11239572 | 9/1999 |
| WO | 87/04080 | 7/1987 |
| WO | 92/10213 | 6/1992 |
| WO | 94/23782 | 10/1994 |
| WO | 97/40396 | 10/1997 |
| WO | 98/52461 | 11/1998 |
| WO | 99/19739 | 4/1999 |
| WO | 00/10456 | 3/2000 |
| WO | 00/25672 | 5/2000 |
| WO | 02/083016 | 10/2002 |
| WO | 2008077037 | 6/2008 |
| WO | 2010008833 | 1/2010 |

OTHER PUBLICATIONS

F.G. Shellock, H. Moschiano, R.S. Johnson, R. Stevenson, S. Brainard, S. Ye, and W. Dabney; Comparative Analyses of MR-Induced Distal Heating in Novel Filtered Cardiac Pacing Leads Using Two Geometric Configurations; 17th Scientific Meeting & Exhibition of the International Society for Magnetic Resonance in Medicine, Honolulu, Hawaii, Apr. 18-24, 2009, p. 3104.

G.D. Wilk, R.M. Wallace and J.M. Anthony, High-k Gate Dielectrics: Current Status and Materials Properties Considerations, Journal of Applied Physics, vol. 89, No. 10, May 15, 2001, pp. 5243-5275, 2001 American Physics.

Wes Clement, et al., "Estimation of Effective Lead Loop Area for Implantable Pulse Generators and Implantable Cardioverter Defibrillators," AAMI EMC Task Force, Apr. 12, 2004, 10 pages.

Ariel Roguin et al., Modem Pacemaker and Implantable Cardioverter/Defibrillator Systems Can Be Magnetic Resonance

(56) References Cited

OTHER PUBLICATIONS

Imaging Safe, Circulation—Journal of the American Heart Association, Aug. 4, 2004 (originally published online Jul. 26, 2004), pp. 475-482, American Heart Association, Dallas, Texas, USA.

Roger Christoph Luchinger, Safety Aspects of Cardiac Pacemakers in Magnetic Resonance Imaging, a dissertation submitted to the Swiss Federal Institute of Technology Zurich. Zurich, Switzerland, 2002.

C. Gabriel, S. Gabriel and E. Cortout, I. Dielectric Properties of Biological Tissues: Literature Survey.

S. Gabriel, R.W. Lau and C. Gabriel, II. Dielectric Properies of Biological Tssues: Measurements and the Frequency Range 0Hz to 20 GHz.

Gabriel, R.W. Lau and C. Gabriel, III. Dielectric Properties of Biological Tissues: Parametric Models for the Dielectric Spectrum of Tissues.

Constatine A. Balanis, Advanced Engineering Electromagnetics, John Wiley & Sons, Inc., 1989.

Robert C. Susil, Christopher J. Yeung, Henry R. Halperin, Albert CL. Lardo, Ergin Atalar, Multifunctional Interventional Devices for MRI: A Combined Electrophysiology/MRI Catheter. Magnetic Resonance in Medicine, 2002, pp. 594-600, Wiley-Liss, Inc., Departments of Biomedical Engineering, Radiology & Medicine, Johns Hopkins University School of Medicine, Baltimore, Maryland.

Robert C. Susil, Ergin Atalar, Albert Lardo, Multifunctional Interventional Devices for Use in MRI, U.S. Appl. No. 60/283,725, filed Apr. 13, 2001.

European Search Report dated Oct. 10, 2012.

European Search Report dated Sep. 19, 2012.

Maurts K. Konings, Lambertus W. Bartels, Henk F.M. Smits and Chris J.G. Bakker, "Heating around Intravascular Guidewires by Resonating RF Waves," Journal of Magnetic Resonance Imaging, 12:79-85, 2000.

Michael J. Weiner, Wilson Greatbatch, Patrick R. Connelly, U.S. Appl. No. 60/269,817 filed Feb. 20, 2001, entitled "Electromagnetic Interference Immune Cardiac Assist System."

Bruce L. Wilkoff M.D., "ICD Extraction Infected/Redundant Leads—Everyday Clinical Practice," Cleveland Clinic, ICD Lead Extraction, Every Day Practice.

Frank G. Shellock, Ph.D. "MRI Issues for Neuromodulation Devices," Institute for Magnetic Resonance Safety, Education, and Research (IMRSER).

R.S. Johnson et al., Characterization of the Relationship between MR-Induced Distal tip Heating in Cardiac Pacing Leads and the Electrical Performance of Novel Filtered Tip Assemblies; 17th Scientific Meeting & Exhibition of the INternational Society for Magnetic Resonance in Medicine, Honolulu, Hawaii, Apr. 18-24, 2009, p. 307.

F.G. Shellock et al., Comparative Analysis of MR-Induced Distal Heating in Novel Filtered Cardiac Pacing Leads Using Two Geometric Configurations; 17th Scientific Meeting & Exhibition of the International Society for Magnetic Resonance in Medicine, Honolulu, Hawaii, Apr. 18-24, 2009, p. 3104.

G.D. Wilk et al., High-k Gate Dielectrics: Current Status and Materials Properties Considerations, Journal of Applied Physics, vol. 89. No. 10, May 15, 2001, pp. 5243-5275, 2001 American Physics.

Wes Clement et al., "Estimation of Effective Lead Loop Area for Implantable Pulse Generators and Implantable Cardioverter Defibriallators," AAMI EMC Task Force, Apr. 12, 2004, 10 pages.

Massarini, Antonio et al., Modeling the Parasitic Capacitance of Inductors—CARTS 96: 16th Capacitor and Resistor Technology Symposium, Mar. 11-15, 1996, pp. 78-84, New Orleans, Louisiana.

Massarini, A. et al., Lumped Parameter Models for Single-and Multiple-Layer Inductors, Jun. 23-27, 1996, IEEE.

\* cited by examiner

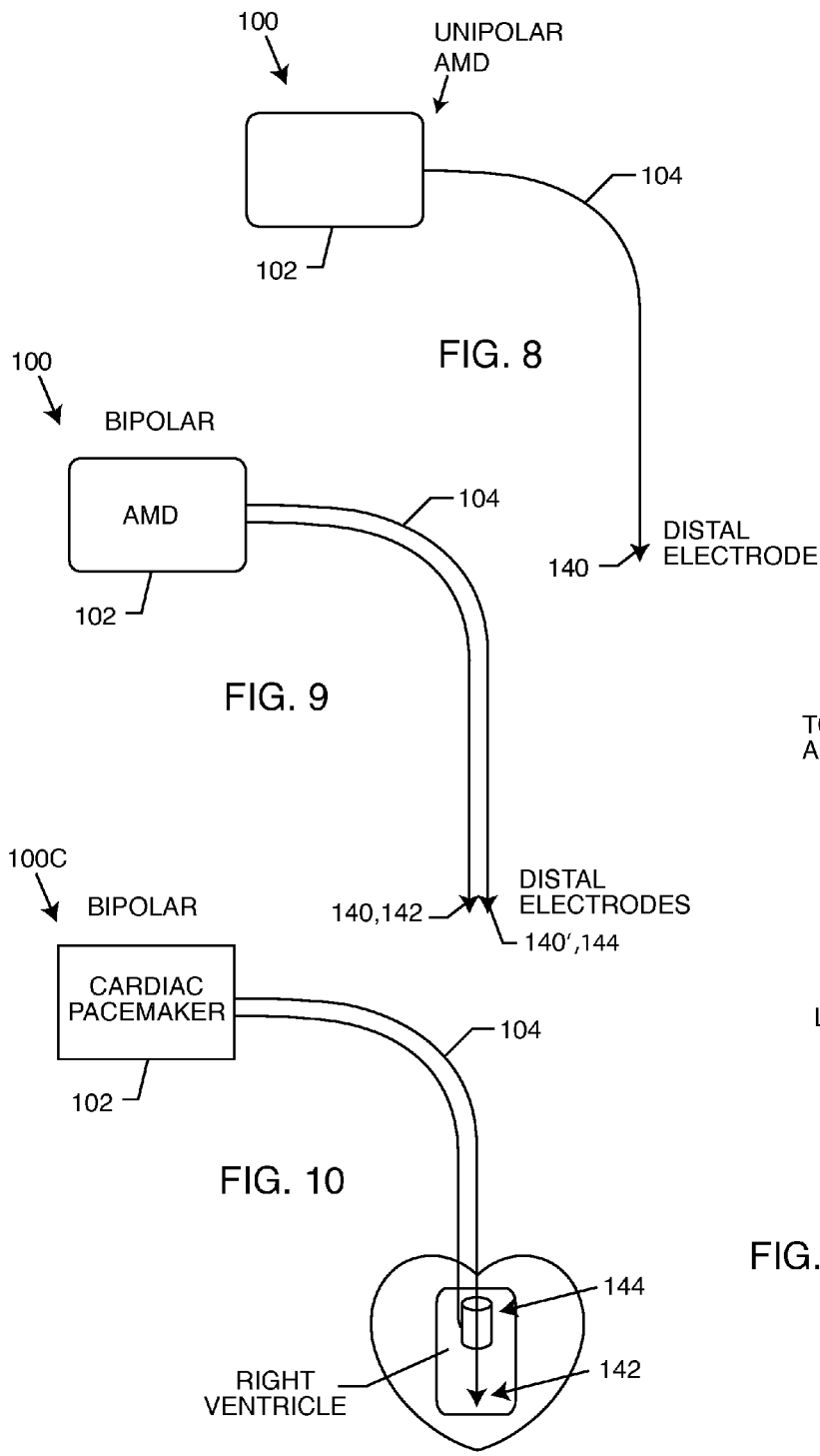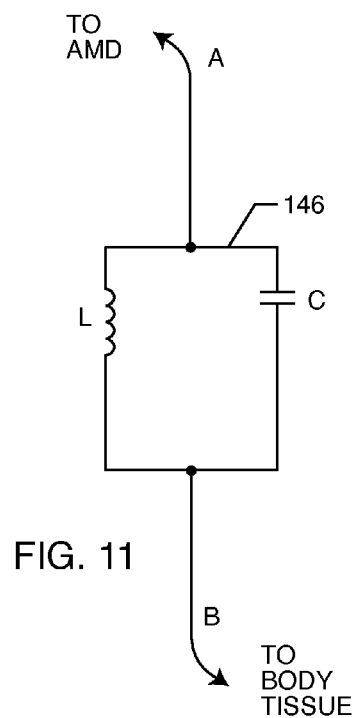

$$fr = \frac{1}{2\pi\sqrt{LC}}$$

Where:  fr = resonant frequency
L = inductance in henries
C = capacitance in farads Solving for C:                    Solving for L:

$$C = \frac{1}{(fr)^2 (2\pi)^2 L} \qquad L = \frac{1}{(fr)^2 (2\pi)^2 C}$$

→ assume a 1.5 Tesla MRI System,
  then the RF pulsed frequency = 64 MHz

→ assume that L = 1 nanohenry (1 x 10$^{-9}$)

$$\text{then; } C = \frac{1}{(64 \times 10^6)^2 (2\pi)^2 (1 \times 10^{-9})}$$

or;  C = 6.18 x 10$^{-9}$ f  (6.18 nanofared)

FIG. 14   $z_{ab} = \dfrac{(j\omega L)(-j/\omega C)}{(j\omega L - j/\omega C)}$

FIG. 15   $X_L = +j(2\pi fL) = +j\omega L$
$X_C = -j\left(\dfrac{1}{2\pi fC}\right) = \dfrac{-j}{\omega C}$

IMPLANTABLE LEAD BANDSTOP FILTER EMPLOYING AN INDUCTIVE COIL WITH PARASITIC CAPACITANCE TO ENHANCE MRI COMPATIBILITY OF ACTIVE MEDICAL DEVICES

CROSS-REFERENCE TO RELATED APPLICATIONS

This application is a continuation-in-part of U.S. application Ser. No. 12/170,811, filed on Jul. 10, 2008, which is a divisional of U.S. application Ser. No. 11/423,073, filed on Jun. 8, 2006, now U.S. Pat. No. 8,244,370.

FIELD OF THE INVENTION

This invention relates generally to novel inductive coil-parasitic capacitance bandstop filter assemblies, particularly of the type used in the implantable leads of active medical devices (AMDs) such as cardiac pacemakers, cardioverter defibrillators, neurostimulators, externally worn Holter monitors and the like, which decouple lead wires and/or electronic components of the medical device from undesirable electromagnetic interference (EMI) signals at a selected center frequency or range of frequencies, such as the RF pulsed fields of Magnetic Resonance Imaging (MRI) equipment.

BACKGROUND OF THE INVENTION

Compatibility of cardiac pacemakers, implantable defibrillators and other types of active implantable medical devices with magnetic resonance imaging (MRI) and other types of hospital diagnostic equipment has become a major issue. If one goes to the websites of the major cardiac pacemaker manufacturers in the United States, which include St. Jude Medical, Medtronic and Boston Scientific (formerly Guidant), one will see that the use of MRI is generally contra-indicated with pacemakers and implantable defibrillators. See also:
(1) "Safety Aspects of Cardiac Pacemakers in Magnetic Resonance Imaging", a dissertation submitted to the Swiss Federal Institute of Technology Zurich presented by Roger Christoph Luchinger, Zurich 2002;
(2) "I. Dielectric Properties of Biological Tissues: Literature Survey", by C. Gabriel, S. Gabriel and E. Cortout;
(3) "II. Dielectric Properties of Biological Tissues: Measurements and the Frequency Range 0 Hz to 20 GHz", by S. Gabriel, R. W. Lau and C. Gabriel;
(4) "III. Dielectric Properties of Biological Tissues: Parametric Models for the Dielectric Spectrum of Tissues", by S. Gabriel, R. W. Lau and C. Gabriel; and
(5) "Advanced Engineering Electromagnetics, C. A. Balanis, Wiley, 1989;
(6) Systems and Methods for Magnetic-Resonance-Guided Interventional Procedures, U.S. Patent Application Pub. 2003/0050557, now U.S. Pat. No. 7,844,319 to Susil et. al.;
(7) Multifunctional Interventional Devices for MRI: A Combined Electrophysiology/MRI Catheter, by, Robert C. Susil, Henry R. Halperin, Christopher J. Yeung, Albert C. Lardo and Ergin Atalar, MRI in Medicine, 2002; and
(8) Multifunctional Interventional Devices for Use in MRI, U.S. Patent Application Ser. No. 60/283,725, filed Apr. 13, 2001, now expired.
(9) Characterization of the Relationship Between MR-Induced Distal Tip Heating in Cardiac Pacing Leads and the Electrical Performance of Novel Filtered Tip Assemblies, by Robert S. Johnson, Holly Moschiano, Robert Stevenson, Scott Brainard, Sam Ye, Joseph E. Spaulding, Warren Dabney, 17$^{th}$ Scientific Meeting & Exhibition of the International Society for Magnetic Resonance in Medicine, Honolulu, Hi., 18-24 Apr. 2009, Page No. 307.
(10) Comparative Analyses of MRI-Induced Distal Heating and Novel Filtered Cardiac Pacing Leads Using Two Geometric Configurations, by F. G. Shellock, Holly Moschiano, Robert Johnson, Robert Stevenson, Scott Brainard, Sam Ye and Warren Dabney, 17$^{th}$ Scientific Meeting & Exhibition of the International Society for Magnetic Resonance in Medicine, Honolulu, Hi., 18-24 Apr. 2009, Page No. 3104. The contents of the foregoing are all incorporated herein by reference.

However, an extensive review of the literature indicates that MRI is indeed often used with pacemaker, neurostimulator and other active medical device (AMD) patients. The safety and feasibility of MRI in patients with cardiac pacemakers is an issue of gaining significance. The effects of MRI on patients' pacemaker systems have only been analyzed retrospectively in some case reports. MRI is one of medicine's most valuable diagnostic tools. MRI is, of course, extensively used for imaging, but is also used for interventional medicine (surgery). In addition, MRI is used in real time to guide ablation catheters, neurostimulator tips, deep brain probes and the like. An absolute contra-indication for pacemaker patients means that pacemaker and ICD wearers are excluded from MRI. This is particularly true of scans of the thorax and abdominal areas. Because of MRI's incredible value as a diagnostic tool for imaging organs and other body tissues, many physicians simply take the risk and go ahead and perform MRI on a pacemaker patient. The literature indicates a number of precautions that physicians should take in this case, including limiting the power of the MRI RF Pulsed field (Specific Absorption Rate—SAR level), programming the pacemaker to fixed or asynchronous pacing mode, and then careful reprogramming and evaluation of the pacemaker and patient after the procedure is complete. There have been reports of latent problems with cardiac pacemakers or other AMDs after an MRI procedure sometimes occurring many days later. Moreover, there are a number of recent papers that indicate that the SAR level is not entirely predictive of the heating that would be found in implanted lead wires or devices. For example, for magnetic resonance imaging devices operating at the same magnetic field strength and also at the same SAR level, considerable variations have been found relative to heating of implanted lead wires. It is speculated that SAR level alone is not a good predictor of whether or not an implanted device or its associated lead wire system will overheat.

There are three types of electromagnetic fields used in an MRI unit. The first type is the main static magnetic field designated B$_0$ which is used to align protons in body tissue. The field strength varies from 0.5 to 3.0 Tesla in most of the currently available MRI units in clinical use. At the International Society for Magnetic Resonance in Medicine (ISMRM), which was held on 5 and 6 Nov. 2005, it was reported that certain research systems are going up as high as 11.7 Tesla. This is over 100,000 times the magnetic field strength of the earth. A static magnetic field can induce powerful mechanical forces and torque on any magnetic materials implanted within the patient. This would include certain components within the cardiac pacemaker itself and or lead wire systems. It is not likely (other than sudden system shut down) that the static MRI magnetic field can induce currents into the pacemaker lead wire system and hence into the pacemaker itself. It is a basic principle of physics that a magnetic field must either be time-varying as it cuts across the conductor, or the conductor itself must move within the magnetic field for currents to be induced.

The second type of field produced by magnetic resonance imaging is the pulsed RF field which is generated by the body coil or head coil. This is used to change the energy state of the protons and illicit MRI signals from tissue. The RF field is homogeneous in the central region and has two main components: (1) the magnetic field is circularly polarized in the actual plane; and (2) the electric field is related to the magnetic field by Maxwell's equations. In general, the RF field is switched on and off during measurements and usually has a frequency of 21 MHz to 64 MHz to 128 MHz depending upon the static magnetic field strength. The frequency of the RF pulse varies with the field strength of the main static field where, for a hydrogen MRI scanner: RF PULSED FREQUENCY in MHz=(42.56) (STATIC FIELD STRENGTH IN TESLA).

The third type of electromagnetic field is the time-varying magnetic gradient fields designated $B_1$ which are used for spatial localization. These change their strength along different orientations and operating frequencies on the order of 1 kHz. The vectors of the magnetic field gradients in the x, y and z directions are produced by three sets of orthogonally positioned coils and are switched on only during the measurements. In some cases, the gradient field has been shown to elevate natural heart rhythms (heart beat). This is not completely understood, but it is a repeatable phenomenon. The gradient field is not considered by many researchers to create any other adverse effects.

It is instructive to note how voltages and EMI are induced into an implanted lead wire system. At very low frequency (VLF), voltages are induced at the input to the cardiac pacemaker as currents circulate throughout the patient's body and create voltage drops. Because of the vector displacement between the pacemaker housing and, for example, the Tip electrode, voltage drop across the resistance of body tissues may be sensed due to Ohms Law and the circulating current of the RF signal. At higher frequencies, the implanted lead wire systems actually act as antennas where currents are induced along their length. These antennas are not very efficient due to the damping effects of body tissue; however, this can often be offset by extremely high power fields (such as MRI RF pulsed fields) and/or body resonances.

Gradient field coupling into an implanted lead wire system is based on loop areas. For example, in a cardiac pacemaker, there is a loop formed by the lead wire as it comes from the cardiac pacemaker housing to its distal Tip electrode, for example, located in the right ventricle. The return path is through body fluid and tissue generally straight from the Tip electrode in the right ventricle back up to the pacemaker case or housing. This forms an enclosed area which can be measured from patient X-rays in square centimeters. The average loop area is 200 to 225 square centimeters (Ref. ANSI/AAMI Standard PC69). This is an average and is subject to great statistical variation. For example, in a large adult patient with an abdominal implant, the implanted loop area is much larger (greater than 450 square centimeters).

Relating now to the specific case of MRI, the magnetic gradient fields would be induced through enclosed loop areas. However, the pulsed RF fields, which are generated by the MRI body coil, would be primarily induced into the lead wire system by antenna action.

There are a number of potential problems with MRI, including:

(1) Closure of the pacemaker reed switch. A pacemaker reed switch, which can also be a Hall Effect device, is designed to detect a permanent magnet held close to the patient's chest. This magnet placement allows a physician or even the patient themselves to put the implantable medical device into what is known as the "magnet mode response." The "magnet mode response" varies from one manufacturer to another; however, in general, this puts the pacemaker into a fixed rate or asynchronous pacing mode. This is normally done for short times and is very useful for diagnostic and clinical purposes. In some cases, when a pacemaker is brought into the bore or close to the MRI scanner, the MRI static field can make the pacemaker's internal reed or Hall effect switch to close, which puts the pacemaker into a fixed rate or asynchronous pacing mode. Worse yet, the reed switch may bounce or oscillate. Asynchronous pacing may compete with the patient's underlying cardiac rhythm. This is one reason why pacemaker patients have generally been advised not to undergo MRI. Fixed rate or asynchronous pacing for most patients is not an issue. However, in patients with unstable conditions, such as myocardial ischemia, there is a substantial risk for ventricular fibrillation during asynchronous pacing. In most modern pacemakers the magnetic reed switch (or Hall Effect device) function is programmable. If the magnetic reed switch response is switched off, then synchronous pacing is still possible even in strong magnetic fields. The possibility to open and re-close the reed switch in the main magnetic field by the gradient field cannot be excluded. However, it is generally felt that the reed switch will remain closed due to the powerful static magnetic field. It is theoretically possible for certain reed switch orientations at the gradient field to be capable of repeatedly closing and re-opening the reed switch.

(2) Reed switch damage. Direct damage to the reed switch is theoretically possible, but has not been reported in any of the known literature. In an article written by Roger Christoph Luchinger of Zurich, he reports on testing in which reed switches were exposed to the static magnetic field of MRI equipment. After extended exposure to these static magnetic fields, the reed switches functioned normally at close to the same field strength as before the test.

(3) Pacemaker displacement. Some parts of pacemakers, such as the batteries and reed switch, contain ferromagnetic materials and are thus subject to mechanical forces during MRI. Pacemaker displacement may occur in response to magnetic force or magnetic torque. There are several recent reports on modern pacemakers and ICDs that force and torque are not of concern for MRI systems up to 3 Tesla.

(4) Radio frequency field. At the frequencies of interest in MRI, RF energy can be absorbed and converted to heat. The power deposited by RF pulses during MRI is complex and is dependent upon the power (Specific Absorption Rate (SAR) Level) and duration of the RF pulse, the transmitted frequency, the number of RF pulses applied per unit time, and the type of configuration of the RF transmitter coil used. The amount of heating also depends upon the volume of tissue imaged, the electrical resistivity of tissue and the configuration of the anatomical region imaged. There are also a number of other variables that depend on the placement in the human body of the AMD and its associated lead wire(s). For example, it will make a difference how much current is induced into a pacemaker lead wire system as to whether it is a left or right pectoral implant. In addition, the routing of the lead and the lead length are also very critical as to the amount of induced current and heating that would occur. Also, distal Tip electrode design is very important as the distal Tip electrode itself can act as its own antenna wherein eddy currents can create heating. The cause of heating in an MRI environment is twofold: (a) RF field coupling to the lead can occur which induces significant local heating; and (b) currents induced between the distal Tip electrode and tissue during MRI RF pulse transmission sequences can cause local Ohms Law heating in tissue next to the distal Tip electrode of the implanted lead. The RF field of an MRI scanner can produce enough energy to induce lead wire currents sufficient to destroy some of the adjacent myocardial tissue. Tissue ablation has also been observed. The effects of this heating are not readily detectable by monitoring during the MRI. Indications that heating has occurred would include an increase in pacing threshold or loss of capture, venous ablation, Larynx or esophageal ablation, myocardial perforation and lead penetration, or even arrhythmias caused by scar tissue. Such long term heating effects of MRI have not been well studied yet for all types of AMD lead wire geometries. There can also be localized heating problems associated with various types of electrodes in addition to Tip electrodes. This includes Ring electrodes or PAD electrodes. Ring electrodes are commonly used with a wide variety of implanted devices including cardiac pacemakers, neurostimulators, probes, catheters and the like. PAD electrodes are very common in neurostimulator applications. For example, spinal cord stimulators or deep brain stimulators can include a plurality of PAD electrodes to make contact with nerve tissue. A good example of this also occurs in a cochlear implant. In a typical cochlear implant there would be approximately 20 Ring electrodes that the physician places by pushing the electrode up into the cochlea. Several of these Ring electrodes make contact with auditory nerves.

(5) Alterations of pacing rate due to the applied MRI radio frequency field. It has been observed that the RF field may induce undesirable fast pacing (QRS complex) rates. There are various mechanisms which have been proposed to explain rapid pacing: direct tissue stimulation, interference with pacemaker electronics or pacemaker reprogramming (or reset). In all of these cases, it is very desirable to raise the lead system impedance (at the MRI RF pulsed frequency) to make an AIMD internal EMI filter feedthrough capacitor more effective and thereby provide a higher degree of protection to AMD electronics. This will make alterations in pacemaker pacing rate and/or pacemaker reprogramming much more unlikely.

(6) Time-varying magnetic gradient fields. The contribution of the time-varying gradient to the total strength of the MRI magnetic field is negligible, however, pacemaker systems could be affected because these fields are rapidly applied and removed. The time rate of change of the magnetic field is directly related to how much electromagnetic force and hence current can be induced into a lead wire system. Luchinger reports that even using today's gradient systems with a time-varying field up to 50 Tesla per second, the induced currents are likely to stay below the biological thresholds for cardiac fibrillation. A theoretical upper limit for the induced voltage by the time-varying magnetic gradient field is 20 volts. Such a voltage during more than 0.1 milliseconds could be enough energy to directly pace the heart.

(7) Heating. Currents induced by time-varying magnetic gradient fields may lead to local heating. Researchers feel that the calculated heating effect of the gradient field is much less as compared to that caused by the RF field and therefore for the purposes herein may be neglected.

There are additional problems possible with implantable cardioverter defibrillators (ICDs). ICDs use different and larger batteries which could cause higher magnetic forces. The programmable sensitivity in ICD biological sense circuits is normally much higher (more sensitive) than it is for pacemakers; therefore, ICDs may falsely detect a ventricular tachyarrhythmia and inappropriately deliver therapy. In this case, therapy might include anti-tachycardia pacing, cardio version or defibrillation (high voltage shock) therapies. MRI magnetic fields may prevent detection of a dangerous ventricular arrhythmia or fibrillation. There can also be heating problems of ICD leads which are expected to be comparable to those of pacemaker leads. Ablation of vascular walls is another concern. Fortunately, ICDs have a sort of built-in fail-safe mechanism. That is, during an MRI procedure, if they inadvertently sense the MRI fields as a dangerous ventricular arrhythmia, the ICD will attempt to charge up and deliver a high voltage shock. However, there is a transformer contained within the ICD that is necessary to function in order to charge up the high-energy storage capacitor contained within the ICD. In the presence of the main static field of the MRI the ferromagnetic core of this transformer tends to saturate thereby preventing the high voltage capacitor from fully charging up. This makes it highly unlikely that an ICD patient undergoing an MRI would receive an appropriate high voltage shock therapy. While ICDs cannot charge during MRI due to the saturation of their ferro-magnetic transformers, the battery will be effectively shorted and lose life. This is a highly undesirable condition.

In summary, there are a number of studies that have shown that MRI patients with active medical devices, such as cardiac pacemakers, can be at risk for potential hazardous effects. However, there are a number of reports in the literature that MRI can be safe for imaging of pacemaker patients when a number of precautions are taken (only when an MRI is thought to be an absolute diagnostic necessity). These anecdotal reports are of interest, however, they are certainly not scientifically convincing that all MRI can be safe. As previously mentioned, just variations in the pacemaker lead wire length can significantly affect how much heat is generated. From the layman's point of view, this can be easily explained by observing the typical length of the antenna on a cellular telephone compared to the vertical rod antenna more common on older automobiles. The relatively short antenna on the cell phone is designed to efficiently couple with the very high frequency wavelengths (approximately 950 MHz) of cellular telephone signals. In a typical AM and FM radio in an automobile, these wavelength signals would not efficiently couple to the relatively short antenna of a cell phone. This is why the antenna on the automobile is relatively longer. An analogous situation exists with an AMD patient in an MRI system. If one assumes, for example, a 3.0 Tesla MRI system, which would have an RF pulsed frequency of 128 MHz, there are certain implanted lead lengths that would couple efficiently as fractions of the 128 MHz wavelength. It is typical that a hospital will maintain an inventory of various leads and that the implanting physician will make a selection depending on the size of the patient, implant location and other factors. Accordingly, the implanted or effective lead wire length can vary considerably. There are certain implanted lead wire lengths that just do not couple efficiently with the MRI frequency and there are others that would couple very efficiently and thereby produce the worst case for heating.

The effect of an MRI system on the function of pacemakers, ICDs and neurostimulators depends on various factors, including the strength of the static magnetic field, the pulse sequence (gradient and RF field used), the anatomic region being imaged, lead length and trajectory, and many other factors. Further complicating this is the fact that each patient's condition and physiology is different and each manufacturer's pacemaker and ICD designs also are designed and behave differently. Most experts still conclude that MRI for the pacemaker patient should not be considered safe.

Paradoxically, this also does not mean that the patient should not receive MRI. The physician must make an evaluation given the pacemaker patient's condition and weigh the potential risks of MRI against the benefits of this powerful diagnostic tool. As MRI technology progresses, including higher field gradient changes over time applied to thinner tissue slices at more rapid imagery, the situation will continue to evolve and become more complex. An example of this paradox is a pacemaker patient who is suspected to have a cancer of the lung. RF ablation treatment of such a tumor may require stereotactic imaging only made possible through real time fine focus MRI. With the patient's life literally at risk, the physician with patient informed consent may make the decision to perform MRI in spite of all of the previously described attendant risks to the pacemaker system.

It is clear that MRI will continue to be used in patients with both external and active implantable medical devices. There are a number of other hospital procedures, including electrocautery surgery, lithotripsy, etc., to which a pacemaker patient may also be exposed. Accordingly, there is a need for AMD system and/or circuit protection devices which will improve the immunity of active medical device systems to diagnostic procedures such as MRI.

As one can see, many of the undesirable effects in an implanted lead system from MRI and other medical diagnostic procedures are related to undesirable induced currents in the conductor(s) of the lead system and/or its distal Ring electrode (or Ring). This can lead to overheating either in the lead or at the body tissue at the distal Ring electrode. For a pacemaker application, these currents can also directly stimulate the heart into sometimes dangerous arrhythmias.

Accordingly, there is a need for a novel resonant bandstop filter assembly which can be placed at one or more locations along the active implantable medical device lead system, which presents a high impedance that prevents RF current from circulating at selected frequencies of the medical therapeutic device. Preferably, such novel bandstop filters would be designed to resonate at 64 MHz for use in an MRI system operating at 1.5 Tesla (or 128 MHz for 3 Tesla system). The present invention fulfills these needs and provides other related advantages.

SUMMARY OF THE INVENTION

The present invention comprises resonant bandstop filters to be placed at one or more locations along the active medical device (AMD) implantable lead system, including at, near or within its distal electrode(s). These bandstop filters prevent current from circulating at selected frequencies of the medical therapeutic device. For example, for an MRI system operating at 1.5 Tesla, the pulsed RF frequency is 64 MHz. The novel bandstop filters of the present invention can be designed to resonate at 64 MHz (and also its harmonics) and thus create a high impedance circuit in the lead wire system at that selected frequency(ies) or across a selected range of frequencies. For example, the bandstop filter of the present invention, when placed at or near the distal Tip electrode, will prevent currents from flowing through the distal Tip electrode, prevent currents from flowing in the lead wires and also prevent currents from flowing into body tissue. It will be apparent to those skilled in the art that all of the embodiments described herein are equally applicable to a wide range of other active implantable or external medical devices, including deep brain stimulators, spinal cord stimulators, cochlear implants, ventricular assist devices, artificial hearts, drug pumps, Holter monitors and the like. The present invention fulfills all of the needs regarding reduction or elimination of undesirable currents and associated heating in implanted lead systems. The bandstop filter structures as described herein also have a broad application to other fields, including telecommunications, military, space and the like.

Electrically engineering a capacitor in parallel with an inductor and causing them to resonate is known as a bandstop or tank filter. It is also well known that when the bandstop filter is at its resonant frequency, it will present a very high impedance. This is a basic principle of all radio receivers. In fact, multiple bandstop filters are often used to improve the selectivity of a radio receiver. One can adjust the resonant frequency of the bandstop filter by either adjusting the capacitor value or the inductor value or both. Since medical diagnostic equipment which is capable of producing very large fields operates at discrete frequencies, this is an ideal situation for a specific bandstop filter. Bandstop filters, also known as tank filters, are more efficient for eliminating one single frequency than broadband low pass filters. Because the bandstop filter is targeted at this one center frequency or range of frequencies, it can be much smaller and volumetrically efficient. In addition, the way MRI RF pulse fields couple with lead systems, various loops and associated loop currents result along various sections of the lead. For example, at the distal Tip electrode of a cardiac pacemaker lead, direct electromagnetic forces (EMF) can be produced which result in current loops through the distal Tip electrode and into the associated myocardial tissue. This current system is largely decoupled from the currents that are induced near the active implantable medical device, for example, near the cardiac pacemaker. There the MRI RF field may set up a separate loop with its associated currents. Accordingly, one or more bandstop filters may be required to completely control all of the various induced EMI and associated currents in a lead system.

The present invention is also designed to work in concert with the EMI filter which is typically used at the point of lead wire ingress and egress of the active implantable medical device, such as those shown in U.S. Pat. No. 5,333,095 to Stevenson et al.; U.S. Pat. No. 6,999,818 to Stevenson et al.; U.S. Pat. No. 7,765,005 to Stevenson; U.S. Patent Application Pub. No. 2007/0083244 A1, now abandoned; U.S. Patent Application Pub. No. 2010/0217264 to Odom et al.; and U.S. Patent Application Pub. No. 2011/0043297 to Stevenson et al., the contents of all being incorporated herein by reference.

As described in U.S. Pat. No. 7,844,319 and U.S. Patent Application Ser. No. 60/283,725, now expired, the present invention is also applicable to probes and catheters. For example, ablation probes are used to selectively cauterize or ablate tissue on the inside or outside of the heart to control erratic electrical pulses. These procedures are best performed during real time fluoroscopy or MRI imaging. However, a major concern is the overheating of the distal Tip electrode at inappropriate times because of the induced currents from the MRI system. It will be apparent to one skilled in the art that the novel bandstop filters of the present invention can be adapted to any probe or catheter that is used in the human body.

Moreover, the present invention is also applicable to a number of external leads that might be placed on a patient during MRI. For example, patients frequently wear Holter monitors to monitor their cardiac activity over a period of days. It is an aggravation to physicians to have a patient sent up to the MRI Department and have all these carefully placed electrodes removed from the patient's body. Typically the MRI technicians are concerned about leaving these leads on during an MRI because they don't want them to overheat and cause surface burns on the patient's skin. The problem is that after the MRI procedure, the MRI technicians often replace these electrodes or skin patches in different or even in the wrong locations. This greatly confounds the cardiac physician because now the Holter monitor results are no longer consistent. It is a feature of the present invention that the bandstop filters could be placed in any externally worn lead wires such that they do not need to be removed for an MRI procedure.

In one embodiment, the invention provides a medical therapeutic device comprising an active medical device (AMD), a lead extending from the AMD to a distal electrode(s) thereof, and one or more bandstop filters associated with the implantable lead for attenuating current flow through the lead conductor(s) at a selected frequency or frequency range.

The AMD may comprise cochlear implants, piezoelectric sound bridge transducers, neurostimulators, brain stimulators, cardiac pacemakers, ventricular assist devices, artificial hearts, drug pumps, bone growth stimulators, bone fusion stimulators, urinary incontinence devices, pain relief spinal cord stimulators, anti-tremor stimulators, gastric stimulators, implantable cardioverter defibrillators, pH probes, congestive heart failure devices, pill cameras, neuromodulators, cardiovascular stents, orthopedic implants, external insulin pumps, external drug pumps, external neurostimulators, and probes or catheters.

In a preferred embodiment, the bandstop filter itself comprises a coiled inductor (L) (and its resistance or an added resistance) in parallel with a parasitic capacitance (C) that is formed between adjacent inductor coils (and its parasitic resistance or an added resistance), said parallel inductance and capacitance combination being placed in series with the medical device lead conductor(s) wherein the values of capacitance and inductance have been selected such that the L-C bandstop filter is resonant at a selected center frequency or frequency range (such as an MRI RF pulsed frequency or range of MRI RF pulsed frequencies). The inductance is inherently derived from the lead's material of construction or structure, and the capacitance is inherently derived from the lead's material of construction or structure.

The $Q_i$ of the inductor may be relatively minimized (or maximized) and the $Q_c$ of the capacitor may be relatively maximized (or minimized) to reduce and/or control the overall Q of the bandstop filter. For example, the $Q_i$ of the inductor is relatively minimized by increasing/controlling the resistive loss in the inductor, and the $Q_c$ of the capacitor is relatively maximized by raising or lowering the equivalent series resistance (ESR) of the capacitor (in this case, the dielectric loss tangent of the inductor coil insulation is important). This reduces the overall Q of the bandstop filter in order to broaden its 3 dB and 10 dB bandwidth points and thereby attenuate current flow through the lead along a range of selected frequencies. The range of selected frequencies may include a plurality of MRI RF pulsed frequencies.

Conversely, the overall Q and 3 dB and 10 dB bandwidths of the resonant bandstop filter may also be controlled with a relatively higher $Q_i$ inductor and a lower $Q_c$ capacitor (or, a balance between the two where the Q of the capacitor and inductor are more equal). To control the capacitor $Q_c$, the equivalent series resistance of the capacitor is based upon the dielectric loss tangent of the insulation dielectric material that coats the elongated wire that forms the coils of the inductor portion of the bandstop filter. Accordingly, dielectric material selection is primarily based on both dielectric constant and on the dielectric loss tangent at the MRI pulsed frequencies of interest.

Preferably, the bandstop filter may be disposed at, near or within the distal electrode(s) of the implantable lead (or external lead in the case of a Holter monitor, etc.) of an active medical device (AMD) and is best integrated into the distal electrode. It may also be integrated into one or more electrodes. The implantable lead may also comprise an externally worn active medical device electronics module, wherein said lead penetrates through the skin surface to an implanted distal electrode. As used herein, the acronym "AMD" shall be inclusive of all AIMDs and AMDs and external devices such as Holter the Pulse OX monitors such as those described above and in FIG. 1.

The present invention provides a novel process for attenuating RF current flow in a lead for an active medical device about a selected center frequency, comprising the steps of: selecting an inductor and parasitic capacitor parallel combination which forms an L-C bandstop filter which is resonant at the selected center frequency or across a selected range of frequencies, and placing the bandstop filter circuit in series with the conductor(s) of the implantable (or external) lead.

In summary, the overall Q of the bandstop filter circuit may be reduced by increasing the $Q_i$ of the inductor and reducing the $Q_c$ of the capacitor. In this regard, minimizing resistive loss in the inductor maximizes the $Q_i$ of the inductor, and raising the equivalent series resistance of the capacitor minimizes the $Q_c$ of the capacitor. Conversely, the overall Q of the bandstop filter may be reduced by decreasing the Q of the inductor and increasing the Q of the capacitor. The overall Q of the bandstop filter could also be reduced by reducing the Q of both the inductor and the capacitor.

The preferred embodiment is to reduce the overall Q of the bandstop filter circuit which widens the 3 dB and 10 dB bandwidths to attenuate current flow through the lead along a range of selected RF frequencies. As discussed herein, the range of selected frequencies may include a plurality of MRI RF pulse frequencies.

It should be noted that the gradient field of the MRI scanner "grades" the static magnetic field $B_0$. This means that the static magnetic field varies at different locations in the human body. This is so a slice (image) of a particular anatomic location and slice width can be generated. This also means that because of the Lamour frequency wherein the RF-pulsed frequency for a hydrogen scanner is equal to 42.56 times the static magnetic field strength, that there is a variation in the RF frequency. This variation can be as much as 270 kHz for a 1.5 Tesla scanner. In other words, it is very important that the 3 dB and 10 dB bandwidths of the bandstop filters be sufficient to attenuate the full range of RF frequencies as the static magnetic field is graded.

It should also be noted that not all 1.5 Tesla (or other) clinical MRI scanners are created equal. They may be all labeled 1.5 Tesla, however, there are significant variations in the static field strength (aka, "the magnet") between one manufacturer's models and particularly between various manufacturers, such as GE, Toshiba, Siemens and the like. As previously noted, the RF pulsed frequency for a hydrogen MRI scanner as given by the Lamour frequency is 42.56 times the static magnetic field strength. However, since the magnets do vary in field strength (even within one manufacturer's model number), there is a corresponding variation in the RF pulsed frequency. This variation can be as much as 0.5 MHz for 1.5 Tesla scanners. Accordingly, controlling the Q and the 3 dB and 10 dB bandwidths of the bandstop filter becomes critical if one is to label an AMD and its lead system for compatibility with all 1.5 Tesla scanners. This is not the case in a dedicated catheter lab (aka "cath lab"). A probe or catheter is inserted into the patient during a short-term minimally invasive cath lab procedure. The dedicated cath lab typically has a single dedicated MRI scanner. For example, it may be a particular GE model number, wherein the static magnetic field strength is precisely known as well as the RF pulsed frequency. In this case, a much more narrow 3 dB bandwidth bandstop filter will suffice. Accordingly, for a dedicated cath lab (and a limited scan protocol), a 10 kHz 10 dB bandwidth may suffice for a particular tissue slice. However, if one were to label, in general, for all 1.5 Tesla scanners, then a bandstop filter 3 dB bandwidth at resonance of approximately 0.5 MHz would be required.

At first glance, it seems contradictory when one can have as narrow as a 10 kHz 10 dB bandwidth. This has to do with the impedance of the bandstop filter. There is a considerable impedance or insertion loss safety margin for a typical bandstop filter, which may have as much as 2000 ohms impedance at its resonant center frequency. In other words, even 15 or 20 dB down, it may provide adequate impedance and adequate protection to protect a lead conductor and/or its distal electrode from RF induced current overheating in an MRI environment. The amount of impedance actually needed from the bandstop filter is subject to a number of variables including the implanted lead trajectory, the implanted lead length, the implanted lead characteristics, the characteristics of the body tissue being imaged, and the like. By way of example, for a particular bandstop filter that had a 10 kHz 3 dB bandwidth with an attenuation of 42 dB at its resonant center frequency, the same filter may have a 20-dB bandwidth of 270 kHz which means that it would provide at least 22 dB of attenuation over the entire gradient modified RF pulse frequency range for a particular MRI scanner. In most cases, 20 dB of attenuation would be adequate to prevent an implanted lead and/or its distal electrode from overheating. The range of frequencies comprises a plurality of MRI RF pulsed frequencies. Moreover, the bandstop filter is designed to have an overall circuit Q wherein the resultant 3 dB bandwidth is at least, in some embodiments, 10 kHz, in others at least 100 kHz, and in still others at least 0.5 MHz.

In a particularly preferred form, the range of frequencies comprises a plurality of MRI RF pulsed frequencies. Moreover, the bandstop filter is designed to have an overall circuit Q wherein the resultant 10 dB bandwidth is at least, in some embodiments, 25 kHz, in others at least 200 kHz, and in still others at least 0.5 MHz.

The lead may comprise a proximal section and a reduced-diameter lead extension, wherein the bandstop filter is disposed between the proximal section and the lead extension (see U.S. Pat. No. 7,899,551). The bandstop filter may also include optional fixation tines. The physical length of the lead extension is preferably less than ½ of the electrical wavelength of the selected center frequency, and in some cases is designed to be less than ¼ or ⅛ of the electrical wavelength of the selected center frequency. Preferably, the lead extension beyond the bandstop filter is less than 15 cm.

The inductance of the bandstop filter may be formed from a coiled or spiral conductor installed in series with the conductor of an implanted lead, and the parallel capacitance is the parasitic capacitance formed between adjacent turns of said inductance. The coiled or spiral conductor that forms the inductor preferably comprises a rectangular or square cross-sectional configuration. One or more conductive end caps may also be conductively conducted to the coiled or spiral conductor to facilitate connection in series with the lead conductor and/or a sensing or therapy delivery electrode. The overall inductor shape may be round, square or flattened (rectangular).

The bandstop filter is designed to resonate at a selected RF center frequency, at multiple frequencies including one or more MRI RF pulse frequencies, or across a selected range of frequencies. The coiled or spiral conductor of the implanted lead inductor(s) may have separate distinct segments having different cross-sectional areas or a different number of turns to form distinct bandstop filters which resonate at different selected center frequencies or ranges or frequencies.

In preferred embodiments, electrical insulation is provided for attenuating stray RF currents from flowing around the bandstop filter through body fluids and tissues. Such stray currents are undesirable in that they thereby degrade the impedance of the bandstop filter at resonance. The insulation may be contiguous with an overall insulation of the implanted lead.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 8 is a schematic diagram of a unipolar active medical device;

FIG. 9 is a diagram similar to FIG. 8, illustrating a bipolar AMD system;

FIG. 10 is a diagram similar to FIGS. 8 and 9, illustrating a bipolar lead wire system with distal Tip and Ring electrodes, typically used in a cardiac pacemaker;

FIG. 11 is a schematic diagram showing a parallel combination of an inductor L and a capacitor C placed in series with the lead wire systems of FIGS. 8-10;

FIG. 12 is a chart illustrating calculation of frequency of resonance for the parallel bandstop filter circuit of FIG. 11;

FIG. 14 is an equation for the impedance of an inductor in parallel with a capacitor;

FIG. 15 is a chart illustrating reactance equations for the inductor and the capacitor of the parallel bandstop filter circuit of FIG. 11;

DETAILED DESCRIPTION OF THE PREFERRED EMBODIMENTS

The present invention is directed to medical lead systems comprising an implantable lead having a proximal end and an electrode in contact with biological cells at a distal end. At least one bandstop filter is associated with a lead conductor for attenuating current flow through the lead over a range of frequencies. The bandstop filter has an overall circuit Q wherein the resultant 3 dB bandwidth is at least 10 kHz and where the bandstop filter comprises a capacitance in parallel with an inductance, wherein values of capacitance and inductance are selected such that the bandstop filter is resonant at a selected center frequency.

As used herein, the term "bandwidth" refers to an attenuation or insertion loss plot measured (or calculated) in a balanced 50-ohm system (50-ohm source and load impedance). The best method is by swept measurements in a 50-ohm spectrum or network analyzer system with proper attention to "thru" and "short" calibrations. The most accurate measurements are of the bandstop filter portion of the lead which shows the performance of the bandstop filter versus frequency. It is best to measure bandstop filter bandwidth before the bandstop filter is installed into the implantable lead. Alternatively, the bandstop filter could be carefully removed (dissected) from the rest of the lead in order to perform the swept measurement. At its resonant center frequency, the bandstop filter has an attenuation peak. The bandwidth is the difference in frequency either computed or measured 3 dB or 10 dB down from the peak.

Figure 1:
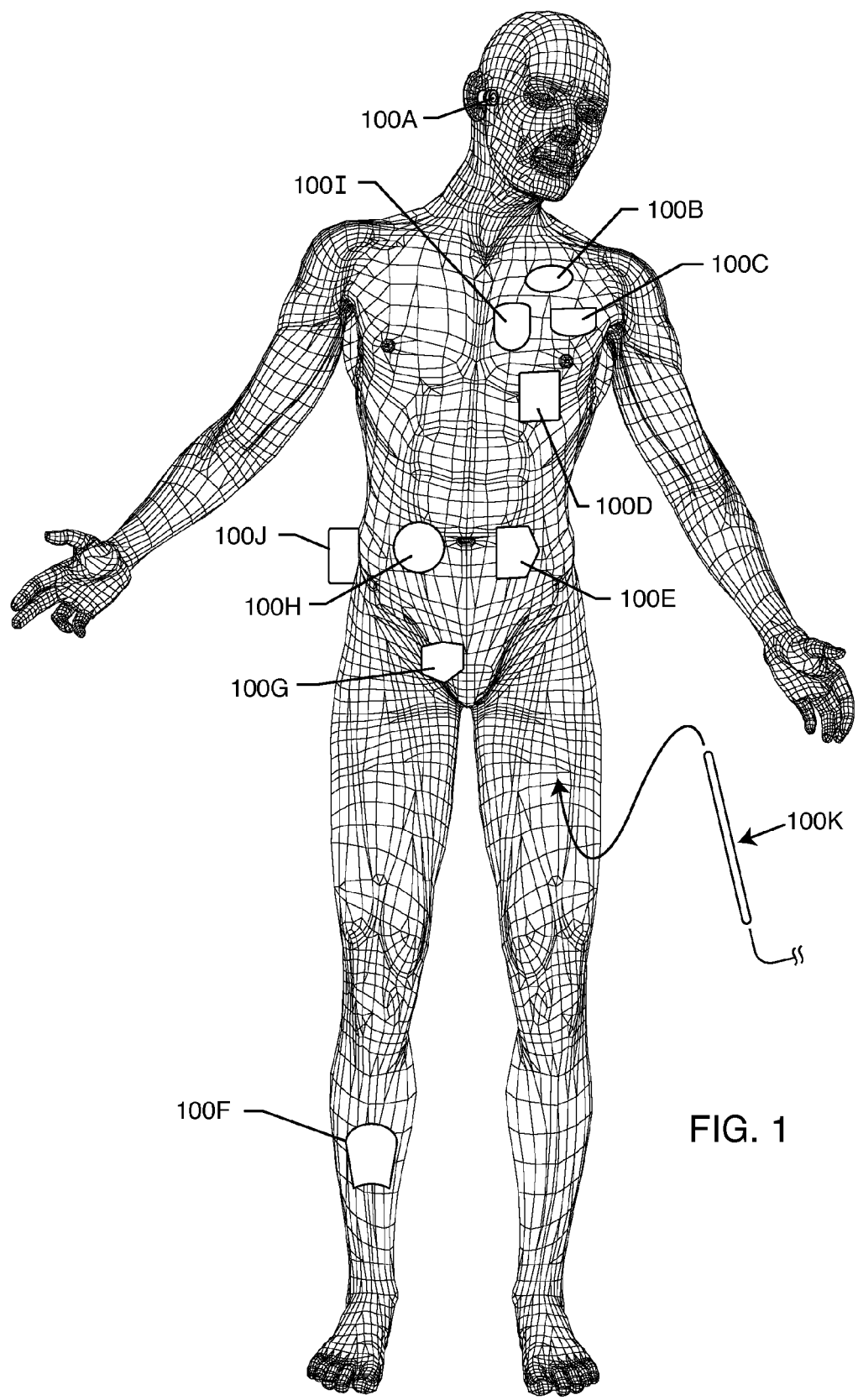
FIG. 1 is a wire-formed diagram of a generic human body showing a number of active implantable medical devices (AMDs)

FIG. 1 illustrates various types of active implantable and external medical devices 100 that are currently in use. FIG. 1 is a wire formed diagram of a generic human body showing a number of implanted medical devices. 100A is a family of external and implantable hearing devices which can include the group of hearing aids, cochlear implants, piezoelectric sound bridge transducers and the like. 100B includes an entire variety of neurostimulators and brain stimulators. Neurostimulators are used to stimulate the Vagus nerve, for example, to treat epilepsy, obesity and depression. Brain stimulators are similar to a pacemaker-like device and include electrodes implanted deep into the brain for sensing the onset of the seizure and also providing electrical stimulation to brain tissue to prevent the seizure from actually happening. The lead wires that come from a deep brain stimulator are often placed using real time imaging. Most commonly such lead wires are placed during real time MRI. 100C shows a cardiac pacemaker which is well-known in the art. 100D includes the family of left ventricular assist devices (LVAD's), and artificial hearts, including the recently introduced artificial heart known as the Abiocor. 100E includes an entire family of drug pumps which can be used for dispensing of insulin, chemotherapy drugs, pain medications and the like. Insulin pumps are evolving from passive devices to ones that have sensors and closed loop systems. That is, real time monitoring of blood sugar levels will occur. These devices tend to be more sensitive to EMI than passive pumps that have no sense circuitry or externally implanted lead wires. 100F includes a variety of external or implantable bone growth stimulators for rapid healing of fractures. 100G includes urinary incontinence devices. 100H includes the family of pain relief spinal cord stimulators and anti-tremor stimulators. 100H also includes an entire family of other types of neurostimulators used to block pain. 100I includes a family of implantable cardioverter defibrillators (ICD) devices and also includes the family of congestive heart failure devices (CHF). This is also known in the art as cardio resynchronization therapy devices, otherwise known as CRT devices. 100J illustrates an externally worn pack. This pack could be an external insulin pump, an external drug pump, an external neurostimulator, a Holter monitor with skin electrodes, a pulse ox monitor, or even a ventricular assist device power pack. 100K illustrates the insertion of an external probe or catheter. These probes can be inserted into the femoral artery, for example, or in any other number of locations in the human body.

Figure 2:
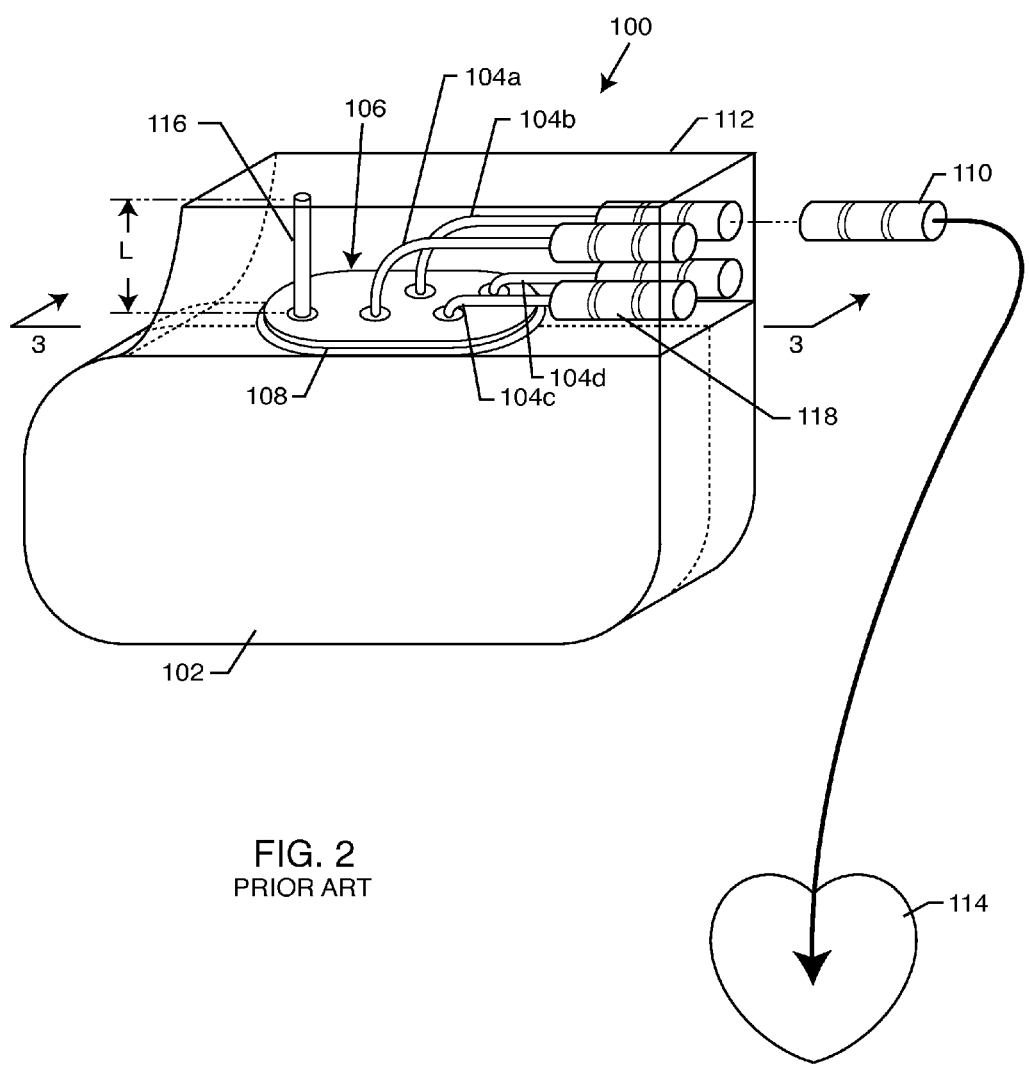
FIG. 2 is a perspective and somewhat schematic view of a prior art active implantable medical device (AMD) including a lead wire directed to the heart of a patient.

FIG. 2 illustrates a prior art active medical device (AMD) 100. In general, the AMD 100 could, for example, be a cardiac pacemaker 100C which is enclosed by a titanium housing 102 as indicated. The titanium housing is hermetically sealed, however there is a point where leads 104 must ingress and egress the hermetic seal. This is accomplished by providing a hermetic terminal assembly 106. Hermetic terminal assemblies are well known and generally consist of a ferrule 108 which is laser welded to the titanium housing 102 of the AMD 100. The hermetic terminal assembly 106 with its associated EMI filter is better shown in FIG. 3. Referring once again to FIG. 2, four leads are shown consisting of lead wire pair 104a and 104b and lead wire pair 104c and 104d. This is typical of what's known as a dual chamber bipolar cardiac pacemaker.

The IS1 connectors 110 that are designed to plug into the header block 112 are low voltage (pacemaker) connectors covered by an ANSI/AAMI standard IS-1. Higher voltage devices, such as implantable cardioverter defibrillators, are covered by a standard known as the ANSI/AAMI DF-1. There is a new standard which integrates both high voltage and low voltage connectors into a new miniature connector series known as the IS4/DF4 series. These connectors are typically routed in a pacemaker application down into the right ventricle and right atrium of the heart 114. There are also new generation devices that have been introduced to the market that couple lead wires to the outside of the left ventricle. These are known as biventricular devices and are very effective in cardiac resynchronization therapy (CRT) and treating congestive heart failure (CHF).

Referring once again to FIG. 2, one can see the bipolar lead wires 104a and 104b that could be routed, for example, to the distal Tip and Ring electrodes into the right ventricle. The bipolar lead wires 104c and 104d could be routed to a distal Tip and Ring electrodes in the right atrium. There is also an RF telemetry pin antenna 116 which is not connected to the IS-1 or DS-1 connector block. This acts as a short stub antenna for picking up telemetry signals that are transmitted from the outside of the device 100.

It should also be apparent to those skilled in the art that all of the descriptions herein are equally applicable to other types of AMDs. These include implantable cardioverter defibrillators (ICDs), neurostimulators, including deep brain stimulators, spinal cord stimulators, cochlear implants, incontinence stimulators and the like, and drug pumps. The present invention is also applicable to a wide variety of minimally invasive AMDs. For example, in certain hospital cath lab procedures, one can insert an AMD for temporary use such as an ICD. Ventricular assist devices also can fall into this type of category. This list is not meant to be limiting, but is only example of the applications of the novel technology currently described herein.

Figure 3:
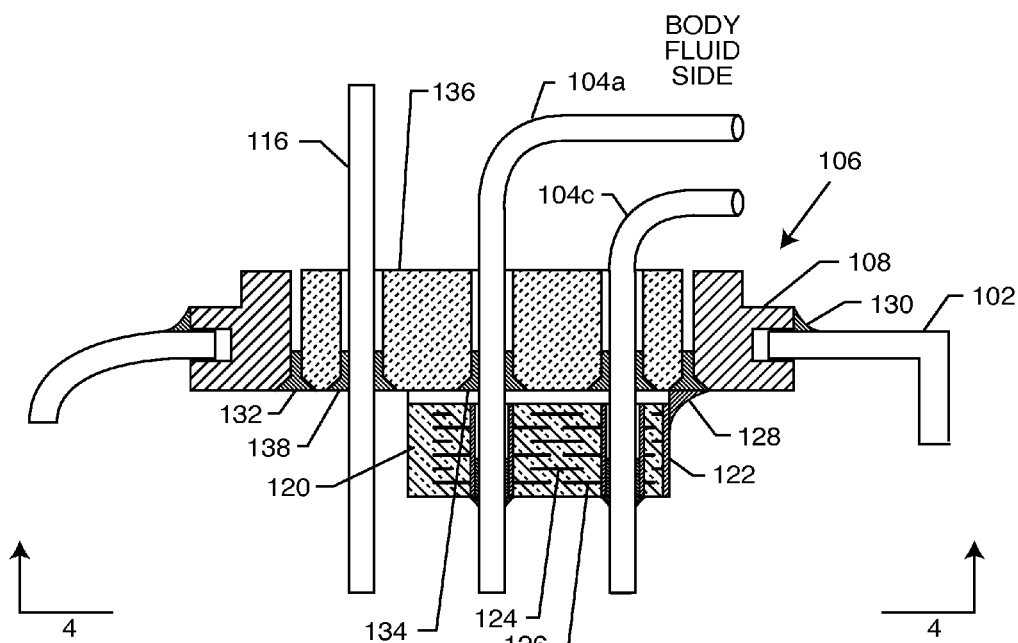
FIG. 3 is an enlarged sectional view taken generally along the line 3-3 of FIG. 2.

FIG. 3 is an enlarged, fragmented cross-sectional view taken generally along line 3-3 of FIG. 2. Here one can see in cross-section the RF telemetry pin 116 and the bipolar lead wires 104a and 104c which would be routed to the cardiac chambers by connecting these lead wires to the internal connectors 118 of the IS-1 header block 112 (FIG. 2). These connectors are designed to receive the plug 110 which allows the physicians to thread leads through the venous system down into the appropriate chambers of the heart 114. It will be apparent to those skilled in the art that tunneling of deep brain electrodes or neurostimulators are equivalent.

One can see a prior art feedthrough capacitor 120 which has been bonded to the hermetic terminal assembly 106. These feedthrough capacitors are well known in the art and are described and illustrated in U.S. Pat. No. 5,333,095; U.S. Pat. No. 5,751,539; U.S. Pat. No. 5,905,627; U.S. Pat. No. 5,959,829; U.S. Pat. No. 5,973,906; U.S. Pat. No. 5,978,204; U.S. Pat. No. 6,008,980; U.S. Pat. No. 6,159,560; U.S. Pat. No. 6,275,369; U.S. Pat. No. 6,424,234; U.S. Pat. No. 6,456,481; U.S. Pat. No. 6,473,291; U.S. Pat. No. 6,529,103; U.S. Pat. No. 6,566,978; U.S. Pat. No. 6,567,259; U.S. Pat. No. 6,643,903; U.S. Pat. No. 6,675,779; U.S. Pat. No. 6,765,780 and U.S. Pat. No. 6,882,248. In this case, a rectangular quadpolar feedthrough capacitor 120 is illustrated which has an external metallized termination surface 122. It includes embedded electrode plate sets 124 and 126. Electrode plate set 124 is known as the ground electrode plate set and is terminated at the outside of the capacitor 120 at the termination surface 122. These ground electrode plates 124 are electrically and mechanically connected to the ferrule 108 of the hermetic terminal assembly 106 using a thermosetting conductive polyimide or equivalent material 128 (equivalent materials will include solders, brazes, conductive epoxies and the like). In turn, the hermetic seal terminal assembly 106 is designed to have its titanium ferrule 108 laser welded 130 to the overall housing 102 of the AMD 100. This forms a continuous hermetic seal thereby preventing body fluids from penetrating into and causing damage to the electronics of the AMD.

It is also essential that the leads 104 and insulator 136 be hermetically sealed, such as by the gold brazes or glass seals 132 and 134. The gold braze 132 wets from the titanium ferrule 108 to the alumina ceramic insulator 136. In turn, the ceramic alumina insulator 136 is also gold brazed at 134 to each of the lead wires 104. The RF telemetry pin 116 is also gold brazed at 138 to the alumina ceramic insulator 136. There are a variety of other ways of making such a hermetic terminal. This would include glass sealing the leads into the ferrule directly without the need for the gold brazes.

As shown in FIG. 3, the RF telemetry pin 116 has not been included in the area of the feedthrough capacitor 120. The reason for this is the feedthrough capacitor 120 is a very broadband single element EMI filter which would undesirably attenuate the RF telemetry frequency.

Figure 4:
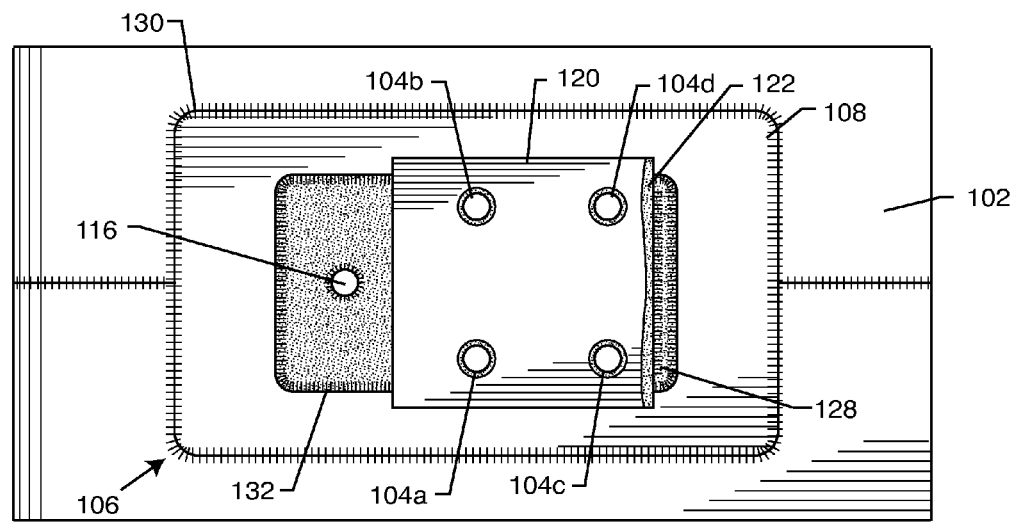
FIG. 4 is a view taken generally along the line 4-4 of FIG. 3.

FIG. 4 is a bottom plan view taken generally along line 4-4 in FIG. 3. One can see the gold braze 132 which completely seals the hermetic terminal insulator 136 into the overall titanium ferrule 108. One can also see the overlap of the capacitor attachment materials, shown as a thermosetting conductive adhesive 128, which makes contact to the gold braze 132 that forms the hermetic terminal 106.

Figure 5:
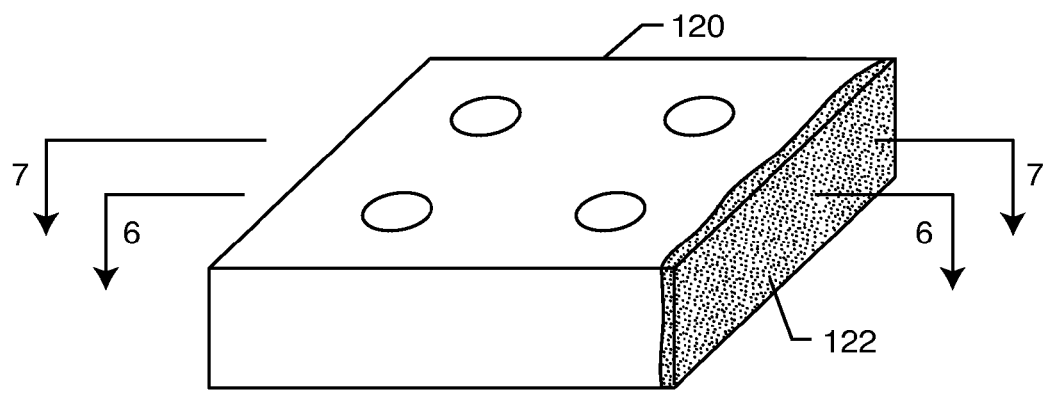
FIG. 5 is a perspective/isometric view of a prior art rectangular quadpolar feedthrough capacitor of the type shown in FIGS. 3 and 4.
Figure 6:
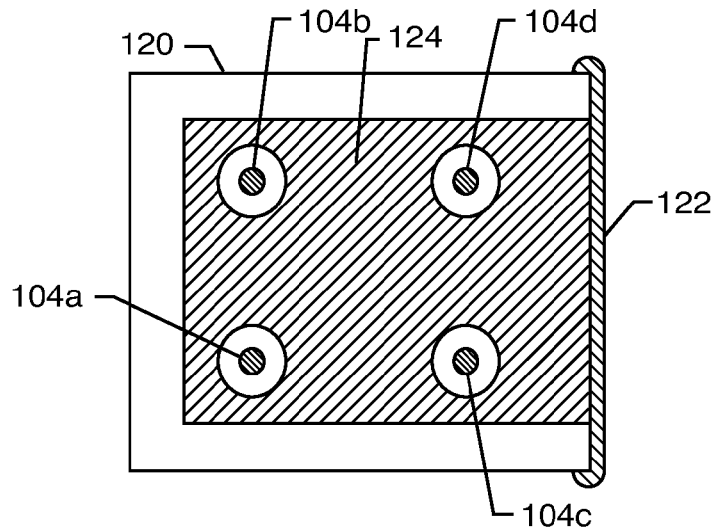
FIG. 6 is sectional view taken generally along the line 6-6 of FIG. 5.
Figure 7:
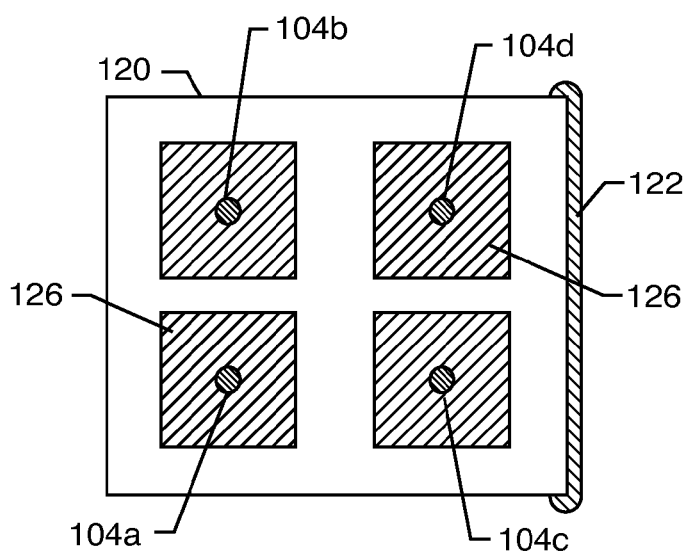
FIG. 7 is a sectional view taken generally along the line 7-7 of FIG. 5.

FIG. 5 is an isometric view of the feedthrough capacitor 120, wherein the termination surface 122 connects to the capacitor's internal ground plate set 124. This is best seen in FIG. 6 where ground plate set 124, which is typically silk-screened onto ceramic layers, is brought out and exposed to the termination surface 122. The capacitor's four (quadpolar) active electrode plate sets 126 are illustrated in FIG. 7. In FIG. 6 one can see that the lead wires 104 are in non-electrical communication with the ground electrode plate set 124. However, in FIG. 7 one can see that each one of the lead wires 104 is in electrical contact with its corresponding active electrode plate set 126. The amount of capacitance is determined by the overlap of the active electrode plate area 126 over the ground electrode plate area. One can increase the amount of capacitance by increasing the area of the active electrode plate set 126. One can also increase the capacitance by adding additional layers. In this particular application, we are only showing six electrode layers: three ground plates 124 and three active electrode plate sets 126 (FIG. 3). However, 10, 60 or even more than 100 such sets can be placed in parallel thereby greatly increasing the capacitance value. The capacitance value is also related to the dielectric thickness or spacing between the ground electrode set 124 and the active electrode set 126. Reducing the dielectric thickness increases the capacitance significantly while at the same time reducing its voltage rating. This gives the designer many degrees of freedom in selecting the capacitance value.

In the following description, functionally equivalent elements shown in various embodiments will often be referred to utilizing the same reference number.

FIG. 8 is a general diagram of a unipolar active medical device (AIMD) system 100. FIG. 8 could also be representative of an externally worn medical device such as a Holter monitor. In the case of a Holter monitor, the distal electrode 140 would typically be a scan or patch electrode. The housing 102 of the active medical device 100 is typically titanium, ceramic, stainless steel or the like. Inside of the device housing are the AMD electronic circuits. Usually AMDs (particularly the type of AMD known as an active "implantable" medical device (AIMD)) include a battery, but that is not always the case. For example, for a Bion, it can receive its energy from an external pulsing magnetic field. A lead 104 is routed from the AMD 100 to a point 140 where it is embedded in or affixed to body tissue. In the case of a spinal cord stimulator 100H, the distal electrode 140 could be in the spinal cord. In the case of a deep brain stimulator 100B, the distal electrode 140 would be placed deep into the brain, etc. In the case of a cardiac pacemaker 100C, the distal electrode 140 would typically be placed in the cardiac right ventricle.

FIG. 9 is very similar to FIG. 8 except that it is a bipolar system. In this case, the electric circuit return path is between the two distal electrodes 140 and 140'. In the case of a cardiac pacemaker 100C, this would be known as a bipolar lead system with one of the electrodes known as the distal Tip electrode 142 and the other electrode which would float in the blood pool known as the Ring electrode 144 (see FIG. 10). In contrast, the electrical return path in FIG. 8 is between the distal electrode 140 through body tissue to the conductive housing 102 of the active medical device 100.

FIG. 10 illustrates a bipolar lead system with a distal Tip electrode 142 and a Ring electrode 144 typically as used in a cardiac pacemaker 100C. In all of these applications, the patient could be exposed to the fields of an MRI scanner or other powerful emitter used during a medical diagnostic procedure. Currents that are directly induced in the lead system 104 can cause heating by $I^2R$ losses in the lead system or by heating caused by current flowing in body tissue. If these currents become excessive, the associated heating can cause damage or even destructive ablation to body tissue.

The distal Tip electrode 142 is designed to be implanted into or affixed to the myocardial tissue of the heart. The Ring electrode 144 is designed to float in the blood pool. Because the blood is flowing and is thermally conductive, the Ring electrode 144 structure is substantially cooled. However, if the lead curves, the Ring electrode 144 could also touch and become encapsulated by body tissue. The distal Tip electrode 142, on the other hand, is always thermally insulated by surrounding body tissue and can readily heat up due to the RF pulse currents of an MRI field.

FIG. 11 is a schematic diagram showing a parallel combination of an inductor or inductance L and a capacitor or capacitance C to be placed in the lead wire systems 104 previously described. This combination forms a parallel bandstop filter circuit 146 which is designed to resonate at a particular RF center frequency ($f_r$).

FIG. 12 gives the frequency of resonance equation $f_r$ for the parallel bandstop circuit 146 of FIG. 11: where $f_r$ is the frequency of resonance in hertz, L is the inductance in henries and C is the capacitance in farads. MRI systems vary in static field strength from 0.5 Tesla all the way up to 3 Tesla with newer research machines going much higher. This is the force of the main static magnetic field. For a hydrogen MRI scanner, the frequency of the pulsed RF field associated with MRI is found by multiplying the static field strength in Teslas times 42.46. Accordingly, a 3 Tesla MRI system has a pulsed RF field of approximately 128 MHz.

Referring once again to FIG. 11, one can see that if the values of the inductance and the capacitance are selected properly, one could obtain a parallel bandstop resonant frequency of 128 MHz. For a 1.5 Tesla MRI system, the RF pulse frequency is 64 MHz. Referring to FIG. 12, one can see the calculations assuming that the inductance value L is equal to one nanohenry. The one nanohenry comes from the fact that given the small geometries involved inside of the human body, a very large inductor will not be possible. This is in addition to the fact that the use of ferrite materials or iron cores for such an inductor are not practical for two reasons: 1) the static magnetic field from the MRI scanner would align the magnetic dipoles (saturate) in such a ferrite and therefore make the inductor ineffective; and 2) the presence of ferrite materials will cause severe MRI image artifacts. What this means is that if one were imaging the right ventricle of the heart, for example, a fairly large area of the image would be blacked out or image distorted due to the presence of these ferrite materials and the way it interacts with the MRI field. It is also important that the inductance value not vary while in the presence of the main static field. In general, an insulated coiled lead conductor has inductance along its unit length. This inductance can be controlled by the coil diameter and spacing, the number of turns, the diameter of the turns, the pitch of the turns and other factors. This results in a fairly low value of inductance per unit length. On the other hand, if one were to use an inductor chip, one can achieve inductance values in the range of 200 to 500 nanohenries. The L/C ratio is important to determine the impedance of the bandstop filter at its primary resonant center frequency. In general, the higher the value of inductance, the higher the bandstop filter impedance will be at the resonant frequency. It is a principle of the present invention, that the bandstop filter can be realized by coils of wire and parasitic capacitance or by placing discrete inductors in parallel with discrete capacitors. One example would be to place a wire wound chip inductor in parallel with a monolithic ceramic capacitor. On the other hand, bandstop filters can also be realized in the present invention by carefully controlling the turns, pitch and dielectric insulation of a coiled or helical lead conductor such that its parasitic inductance is resonant with its parasitic capacitance at a selected MRI RF frequency.

The relationship between the parallel inductance L and capacitance C is also very important. One could use a very large value of inductance which would result in a very small value of capacitance to be resonant, for example, at the MRI frequency of 64 MHz. However, using a very high value of inductance results in a high number of turns (coils) of very small wire. Using a high number of turns of very small diameter wire has to be done carefully for two reasons. The first reason is that the long length of relatively small diameter wire results in a very high resistance for the inductor. This resistance has to be limited because low frequency pacing or neurostimulator pulses would lose energy passing through the relatively high series resistance. Too much resistance is undesirable where the AMD is sensing biologic signals. For example, in the case of a pacemaker or deep brain stimulator, continuous sensing of low frequency biological signals is required. Too much series resistance in a lead wire system will attenuate such signals thereby making the AMD less efficient. In one embodiment, an inductance on the order of 200 nanohenries is used in parallel with a capacitance of 15 to 20 picofarads to create a resonant bandstop filter at 64 MHz. At resonance, RF currents circulate back and forth between the inductance and the capacitance of the bandstop filter at the MRI RF pulsed frequency. In other words, for a 1.5 Tesla MRI scanner, at 64 million times per second, the capacitor discharges into the inductive field of the inductor and then reverses wherein the inductive field of the inductor collapses into the electric field of the capacitor. This current passes back and forth in the bandstop filter through the resistance of the inductor and the high frequency equivalent series resistance (ESR) of the capacitor. Because of these resistances, this circulating current in the bandstop filter can cause it to heat up. Accordingly, in a preferred embodiment, the bandstop filter is shielded wherein the shield can dissipate heat generated in the bandstop filter into surrounding body fluids or tissues over a relatively large surface area.

It should be also noted that below resonance, particularly at very low frequencies, the implantable lead pacing pulses or biological signals pass through the inductor element of the parallel L-C bandstop filter. Accordingly, it is important that the parasitic resistance of the inductor not be excessive. Conversely, at very low frequencies, no current passes through the capacitor element. At very high frequencies (greater than 1000 MHz), the reactance of the capacitor element drops to a very low value. However, as there is no case where it is actually desirable to have high frequencies pass through the bandstop filter, the parasitic resistive loss of the capacitor is not particularly important. This is also known as the capacitor's equivalent series resistance (ESR). A component of capacitor ESR is the dissipation factor (dielectric loss tangent) of the capacitor (a relatively low frequency phenomena). Off of resonance, it is not particularly important how high the capacitor's dissipation factor or overall ESR is when used as a component of a parallel bandstop circuit 146 as described herein. Accordingly, an air core wound sobnoid-type inductor (which can be coils of the lead conductor) is the ideal choice because it is not affected by MRI signals or fields. As used herein, "airwound" means that there is no ferromagnetic core for the inductor such as a ferrite toroid, slug or cylinder. Because of the space limitations, however, the air wound coil inductor will not be very volumetrically efficient. For this reason, and due to size limitations, it is preferable to keep the inductance value relatively low (typically in the range of 1 to 500 nanohenries).

Referring once again to FIG. 12, one can see the calculations for capacitance by algebraically solving the resonant frequency $f_r$ equation shown for C. Assuming an inductance value of one nanohenry, six nano-farads of capacitance would be required. Six nano-farads of capacitance is a relatively high value of capacitance. However, ceramic dielectrics that provide a very high dielectric constant are well known in the art and are very volumetrically efficient. They can also be made of biocompatible materials making them an ideal choice for use in the present invention. Moreover, a dielectric coating of ceramic or nano-particle dielectric would be a method of providing for a high value of parasitic capacitance.

Figure 13:
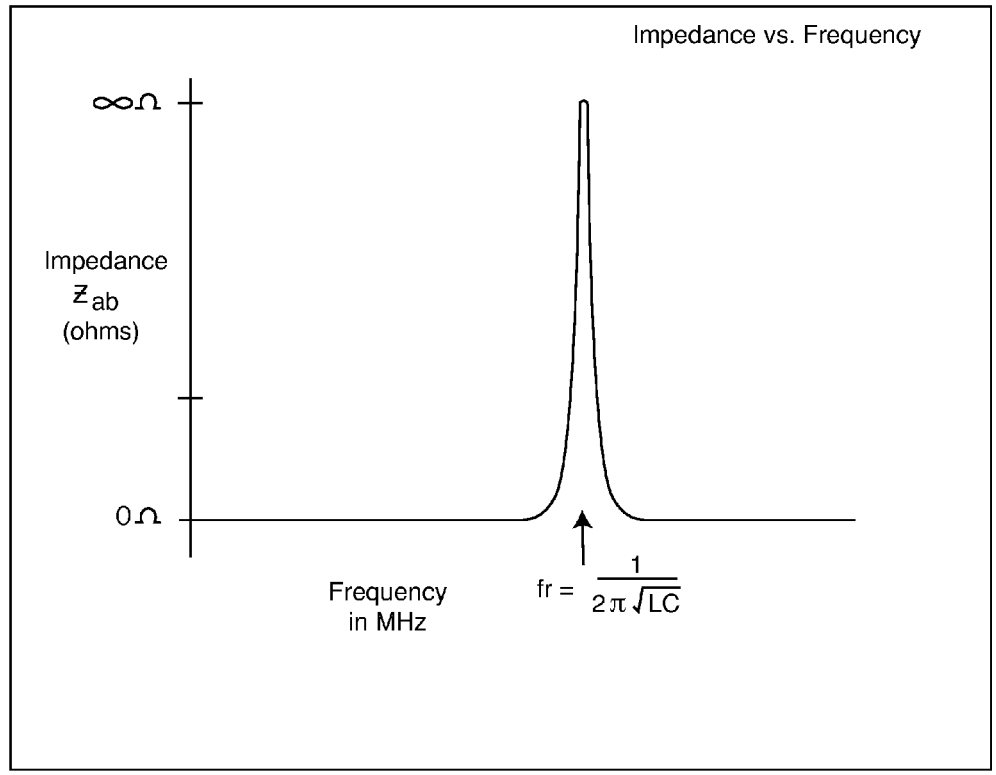
FIG. 13 is a graph showing impedance versus frequency for the parallel bandstop filter circuit of FIG. 11.

FIG. 13 is a graph showing impedance versus frequency for the parallel tank or bandstop filter circuit 146 of FIG. 11. As one can see, using ideal (zero resistance) circuit components, the impedance measured between points A and B for the parallel bandstop filter 146 shown in FIG. 11 is very low (zero) until one approaches the resonant frequency $f_r$. At the frequency of resonance, these ideal components combine together to look like a very high or, ideally, an infinite impedance. The reason for this comes from the denominator of the equation $Z_{ab}$ for the impedance for the inductor in parallel with the capacitor shown as FIG. 14. When the inductive reactance is equal to the capacitive reactance, the two imaginary vectors cancel each other and go to zero. Referring to the equations in FIGS. 14 and 15, one can see in the impedance equation for $Z_{ab}$, that a zero will appear in the denominator when $X_L = X_C$. This has the effect of making the impedance approach infinity as the denominator approaches zero. As a practical matter, one does not really achieve an infinite impedance. However, tests have shown that several hundred or even thousands of ohms can be realized which offers a great deal of attenuation and protection to RF pulsed currents from MRI. What this means is that at one particular unique frequency, the impedance between points A and B in FIG. 11 will appear very high (analogous to opening a switch). Accordingly, it would be possible, for example, in the case of a cardiac pacemaker, to design the cardiac pacemaker for compatibility with one single popular MRI system. For example, in the AMD patient literature and physician manual it could be noted that the pacemaker lead system has been designed to be compatible with 3 Tesla MRI systems. Accordingly, with this particular device, a distal Tip bandstop filter 146 would be incorporated where the L and the C values have been carefully selected to be resonant at a center frequency of 128 MHz, presenting a high impedance at the MRI RF pulse frequency.

Figure 16:
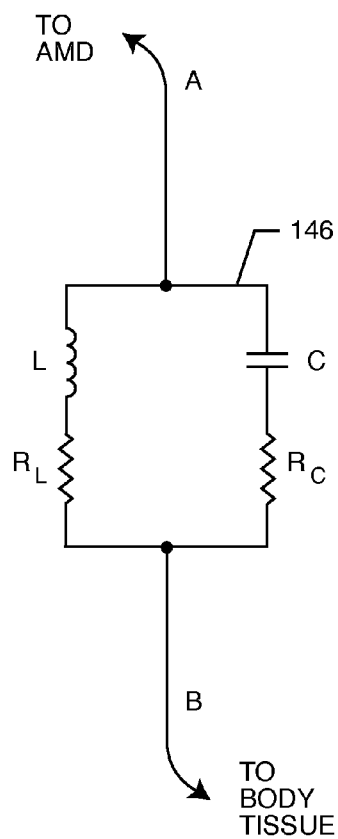
FIG. 16 is a schematic diagram illustrating the parallel bandstop filter circuit of FIG. 11, except in this case the inductor and the capacitor have series resistive losses.

FIG. 16 is a schematic drawing of the parallel bandstop circuit 146 of FIG. 11, except in this case the inductor L and the capacitor C are not ideal. That is, the capacitor C has its own internal resistance $R_C$, which is otherwise known in the industry as equivalent series resistance (ESR). The inductor L also has a resistance $R_L$. For those that are experienced in passive components, one would realize that the inductor L has parallel capacitance. This parasitic capacitance comes from the stray capacitance associated with adjacent inductor turns. Accordingly, the circuit shown in FIG. 16 is a very good approximation model for the novel parallel bandstop circuits 146 as described herein.

This is best understood by considering the FIG. 16 bandstop filter circuit 146 at the frequency extremes. The inductive reactance equation is $X_L = 2\pi f L$ (reference FIG. 15). When the frequency f is close to zero (DC), this means that the inductor looks like a short circuit. It is generally the case that biologic signals are low frequency, typically between 10 Hz and 1000 Hz. For example, in a cardiac pacemaker 100C, the frequencies of interest appear between 10 Hz and 1000 Hz. At these low frequencies, the inductive reactance $X_L$ will be very close to zero ohms. Over this range, on the other hand, the capacitive reactance $X_C$ which has the equation $X_C = 1/(2\pi f c)$ will look like an infinite or open circuit (reference FIG. 15). As such, at low frequencies, the impedance between points A and B in FIG. 16 will equal to $R_L$. Accordingly, the resistance of the inductor ($R_L$) should be kept as small enough to minimize attenuation of biologic signals or attenuation of stimulation pulses to body tissues. This will allow biologic signals to pass through the bandstop filter 146 freely. It also indicates that the amount of capacitive loss $R_C$ is not particularly important. As a matter of fact, it would be desirable if that loss were fairly high so as to not freely pass very high frequency signals (such as undesirable EMI from cellular phones). It is also desirable to have the Q of the circuit shown in FIG. 16 relatively low so that the bandstop filter 3 dB frequency bandwidth can be a little wider. In other words, in a preferred embodiment, it would be possible to have a bandstop filter resonance curve wide enough at the 3 dB and 10 dB down points to attenuate the RF pulsed frequencies over a range of 1.5 Tesla scanners. As previously mentioned, the RF pulsed frequency variation of commercial scanners can be as much as 0.5 MHz to 1 MHz (this variation is MR machine to MR machine and also from manufacturer to manufacturer).

Figure 17:
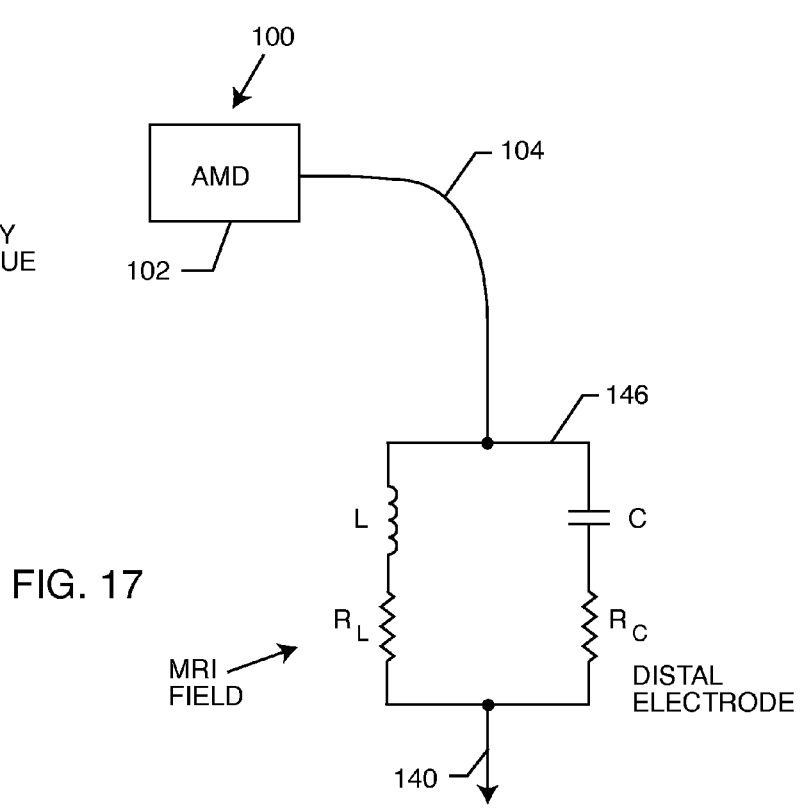
FIG. 17 is a diagram similar to FIG. 8, illustrating the bandstop filter added near the distal electrode.

FIG. 17 is a drawing of the unipolar AMD lead wire system, shown in FIG. 8, with the bandstop filter 146 of the present invention added near the distal electrode 140. As previously described, the presence of the bandstop circuit 146 will present a very high impedance at a selected resonant center frequency as well as across a selected range of MRI RF pulse frequencies. This will prevent currents from circulating through the distal electrode 140 into body tissue at this selected frequency(s). This will provide a very high degree of important protection to the patient so that overheating does not cause tissue damage.

Figure 18:
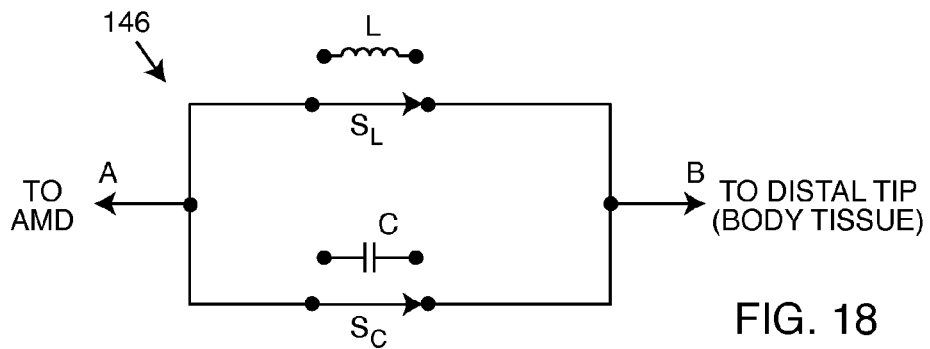
FIG. 18 is a schematic representation of the novel bandstop filter of the present invention, using switches to illustrate its function at various frequencies.

FIG. 18 is a representation of the novel bandstop filter 146 using equivalent switches that open and close at various frequencies to illustrate its function. Inductor L has been replaced with a switch $S_L$. When the impedance of the inductor is quite low, the switch $S_L$ will be closed. When the impedance or inductive reactance of the inductor is high, the switch $S_L$ will be shown open. There is a corresponding analogy for the capacitor element C. When the capacitive reactance looks like a very low impedance, the capacitor switch $S_C$ will be shown closed. When the capacitive reactance is shown as a very high impedance, the switch $S_C$ will be shown open. This analogy is best understood by referring to FIGS. 19, 20 and 21.

Figure 19:
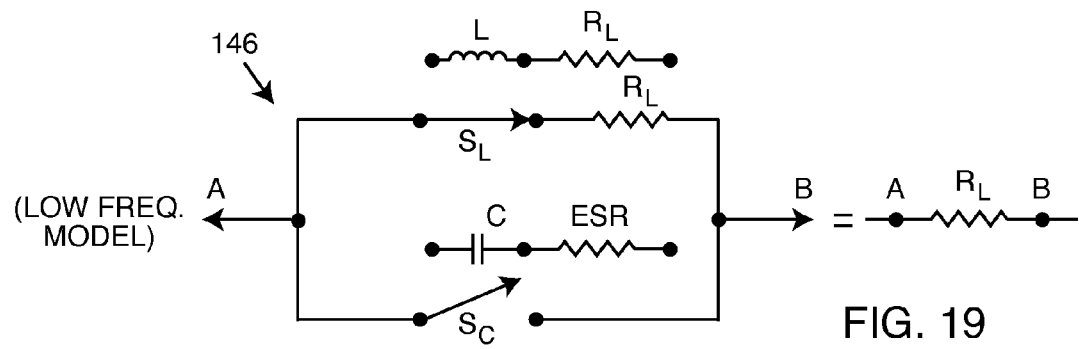
FIG. 19 is a schematic diagram similar to FIG. 18, illustrating the low frequency model of the bandstop filter.

FIG. 19 is the low frequency model of the bandstop filter 146. At low frequencies, capacitors tend to look like open circuits and inductors tend to look like short circuits. Accordingly, switch $S_L$ is closed and switch $S_C$ is open. This is an indication that at frequencies below the resonant frequency of the bandstop filter 146 that currents will flow only through the inductor element and its corresponding resistance $R_L$. This is an important consideration for the present invention that low frequency biological signals not be attenuated. For example, in a cardiac pacemaker, frequencies of interest generally fall between 10 Hz and 1000 Hz. Pacemaker pacing pulses fall within this general frequency range. In addition, the implantable medical device is also sensing biological frequencies in the same frequency range. Accordingly, such signals must be able to flow readily through the bandstop filter's inductor element. A great deal of attention should be paid to the inductor design so that it has a low enough value of parasitic series resistance $R_L$.

Figure 20:
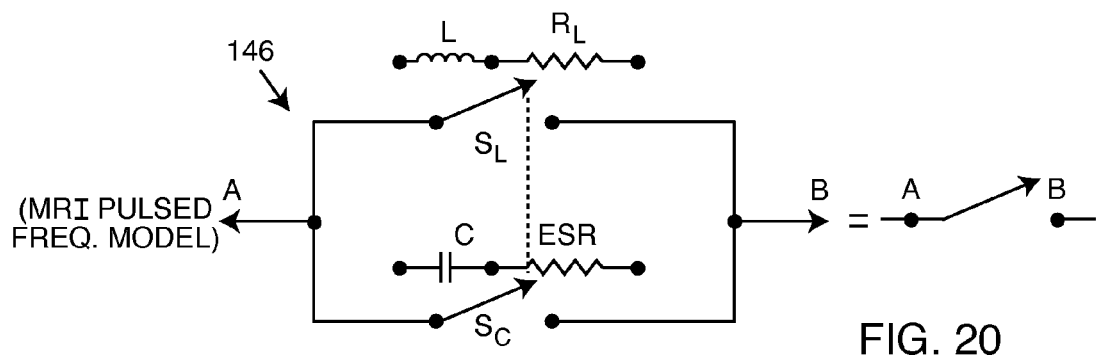
FIG. 20 is a schematic diagram similar to FIGS. 18 and 19, illustrating the model of the bandstop filter of the present invention at its resonant frequency.

FIG. 20 is a model of the novel bandstop filter 146 at its resonant frequency. By definition, when a parallel bandstop circuit is at resonance, it presents a very high impedance to the overall circuit. Accordingly, both switches $S_L$ and $S_C$ are shown open. For example, this is how the bandstop filter 146 prevents the flow of MRI currents through pacemaker lead wires and/or into body tissue at a selected MRI RF pulsed frequency.

Figure 21:
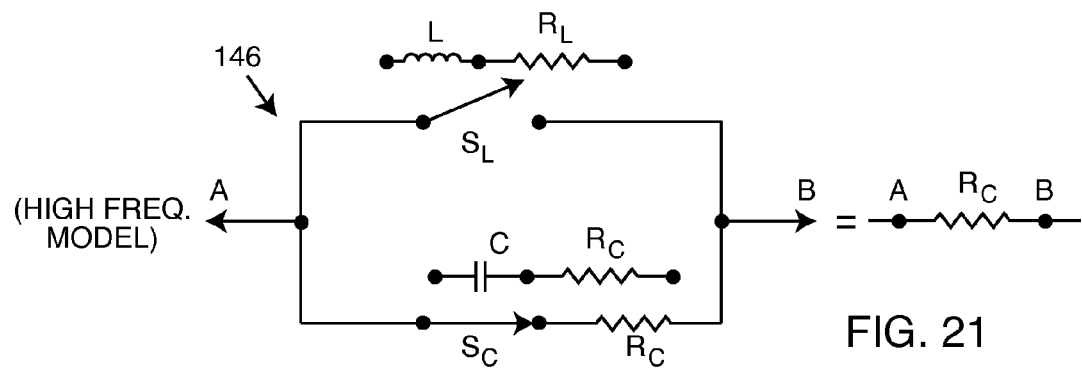
FIG. 21 is a schematic diagram similar to FIGS. 18-20, illustrating a model of the bandstop filter at high frequencies well above the resonant frequency.

FIG. 21 is a model of the bandstop filter 146 at high frequency. At high frequencies, inductors tend to look like open circuits. Accordingly, switch $S_L$ is shown open. At high frequencies, ideal capacitors tend to look like short circuits, hence switch $S_C$ is closed. Fortunately, for the present invention, it is not important how lossy (resistive) the capacitor element C gets at high frequency. This will only serve to attenuate unwanted electromagnetic interference from flowing in the lead wire system. Accordingly, in terms of biological signals, the equivalent series resistance $R_C$ and resulting quality factor of the capacitor element C is not nearly as important as the quality factor of the inductor element L. The equation for inductive reactance ($X_L$) is given in FIG. 15. The capacitor reactance equation ($X_C$) is also given in FIG. 15. As one can see, when one inserts zero or infinity for the frequency, one derives the fact that at very low frequencies inductors tend to look like short circuits and capacitors tend to look like open circuits. By inserting a very high frequency into the same equations, one can see that at very high frequency ideal inductors look like an infinite or open impedance and ideal capacitors look like a very low or short circuit impedance.

Figure 22:
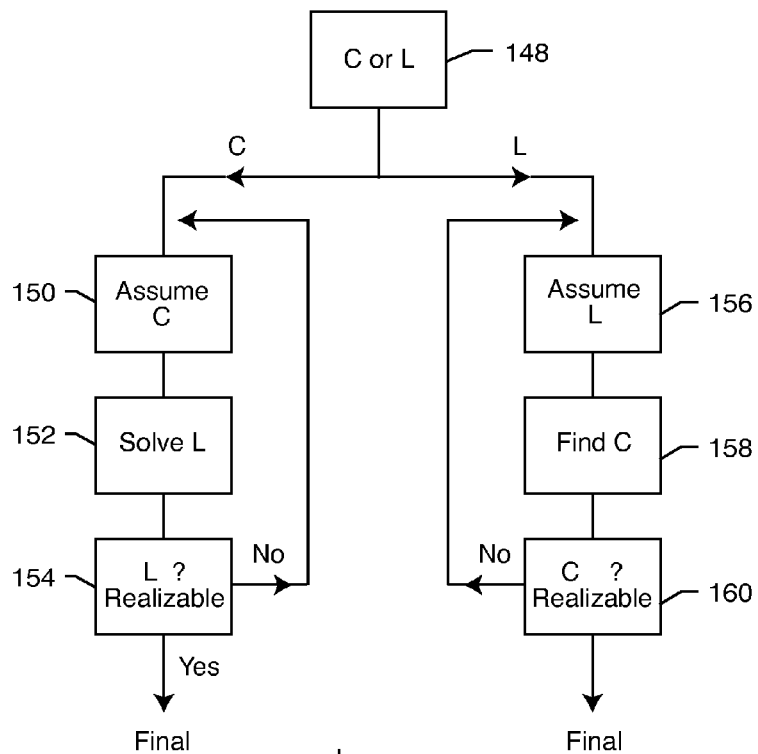
FIG. 22 is a decision tree block diagram illustrating a process for designing the bandstop filters of the present invention.

FIG. 22 is a decision tree block diagram that better illustrates the design process herein. Block 148 is an initial decision step the designer must make. For illustrative purposes, we will start with a value of capacitance that is convenient. This value of capacitance is generally going to relate to the amount of space available in the AMD lead wire system and other factors. These values for practical purposes generally range in capacitance value from a few picofarads up to about 10,000 picofarads. This puts practical boundaries on the amount of capacitance that can be effectively packaged within the scope of the present invention. However, that is not intended to limit the general principles of the present invention, but just describe a preferred embodiment. Accordingly, in the preferred embodiment, one will select capacitance values generally ranging from 1 picofarad up to about 10,000 picofarads and then solve for a corresponding inductance value required to be self-resonant at the selected telemetry frequency. Referring to FIG. 22, one makes the decision whether the design was C first or L first. If one makes a decision to assume a capacitance value C first then one is directed to the left to block 150. In block 150, one does an assessment of the overall packaging requirements of a distal Tip 142 bandstop filter 146 and then assumes a realizable capacitance value. So, in decision block 150, we assume a capacitor value. We then solve the resonant tank equation $f_r$ from FIG. 12 at block 152 for the required value of inductance (L). We then look at a number of inductor designs to see if the inductance value is realizable within the space, parasitic resistance $R_C$, and other constraints of the design. If the inductance value is realizable, then we go on to block 154 and finalize the design. If the inductance value is not realizable within the physical and practical constraints, then we need to go back to block 150 and assume a new value of capacitance. One may go around this loop a number of times until one finally comes up with a compatible capacitor and an inductor design. In some cases, one will not be able to achieve a final design using this alone. In other words, one may have to use a custom capacitor value or design in order to achieve a result that meets all of the design criteria. That is, a capacitor design with high enough internal losses $R_C$ and an inductor design with low internal loss $R_L$ such that the bandstop filter 146 has the required quality factor (Q), that it be small enough in size, that it have sufficient current and high voltage handling capabilities and the like. In other words, one has to consider all of the design criteria in going through this decision tree.

In the case where one has gone through the left hand decision tree consisting of blocks 150, 152 and 154 a number of times and keeps coming up with a "no," then one has to assume a realizable value of inductance and go to the right hand decision tree starting at block 156. One then assumes a realizable value of inductance (L) with a low enough series resistance for the inductor $R_L$ such that it will work and fit into the design space and guidelines. After one assumes that value of inductance, one then goes to decision block 158 and solves the equation C in FIG. 12 for the required amount of capacitance. After one finds the desired amount of capacitance C, one then determines whether that custom value of capacitance will fit into the design parameters. If the capacitance value that is determined in step 160 is realizable, then one goes on and finalizes the design. However, if it is not realizable, then one can go back up to step 156, assume a different value of L and go through the decision tree again. This is done over and over until one finds combinations of L and C that are practical for the overall design.

It is possible to use series discrete inductors or parallel discrete capacitors to achieve the same overall result. For example, in the case of the inductor element L, it would be possible to use two, three or even more (n) individual inductor elements in series. The same is true for the capacitor element that appears in the parallel bandstop filter 146. By adding or subtracting capacitors in parallel, we are also able to adjust the total capacitance that ends up resonating in parallel with the inductance.

Moreover, an inductive coil component has significant parasitic capacitance between its adjacent turns. The inductive parasitic capacitance bandstop filter component can comprise a portion of an implantable lead or even the entire length of an implantable lead. A careful designer using multiple turns can create enough parasitic capacitance such that the inductive coil becomes self-resonant at a predetermined frequency. For example, see U.S. Pat. No. 7,363,090 Col. 19 lines 59-65. In this case, the predetermined frequency would be the MRI pulsed RF center frequency. The inductive-parasitic capacitance bandstop filter-component(s) may be formed of the coaxial or helical conductor turns of the implanted lead 104 itself wherein the parasitic or stray capacitance is formed between adjacent turns. The amount of capacitance is controlled by a dielectric coating on the lead conductor (dielectric constant and thickness), the number of turns, the ECA, the pitch and the coil spacing. Stray capacitance is synonymous with "parasitic capacitance." A discussion of how stray capacitance can be used in bandstop filter applications is found in US 2003/0050557. Multiple inductive components with stray capacitance can also be used to create multiple bandstop filters in series with different resonant frequencies. This would be particularly useful for compatibility with 1.5 Tesla, 3 Tesla and the like MRI scanners.

In all of the previously described embodiments, it is preferred that the bandstop filter be as close to the electrode-to-tissue interface as possible. The reason for this is that the lead and its associated conductors can act as an antenna (and also as a transmission line). When an antenna is an efficient multiple of a wavelength, it can pick up a great deal of energy from the external environment. In particular, the RF pulse fields from an MRI scanner can induce high levels of current in implanted leads and their associated electrodes, which can be damaging to body tissue. In other words, the bandstop filter should be placed in relatively close proximity to the therapy sense or delivery electrodes as illustrated.

This principle varies with the RF pulsed frequency of the MRI scanner. For example, a 0.5 Tesla scanner has an RF pulsed frequency of 21 MHz In this case, the wavelength is long enough where the bandstop filter could be a considerable distance away from the lead distal electrode and still be quite effective. However, when one gets up around 3 Tesla with an RF pulsed frequency of 128 MHz, then the bandstop filter must be much closer to the delivery electrode. This is because the wavelength of the higher RF pulsed frequencies gets much shorter and can therefore couple more effectively to a short distal lead extension (distal of the bandstop filter). In the present invention, preferably the inductive-parasitic capacitance bandstop filter is no more than 15 cm away from the delivery electrode. This will provide effective reduction in current flow at the MRI RF pulsed frequency thereby providing effective cooling at the distal electrode tips.

Figure 23:
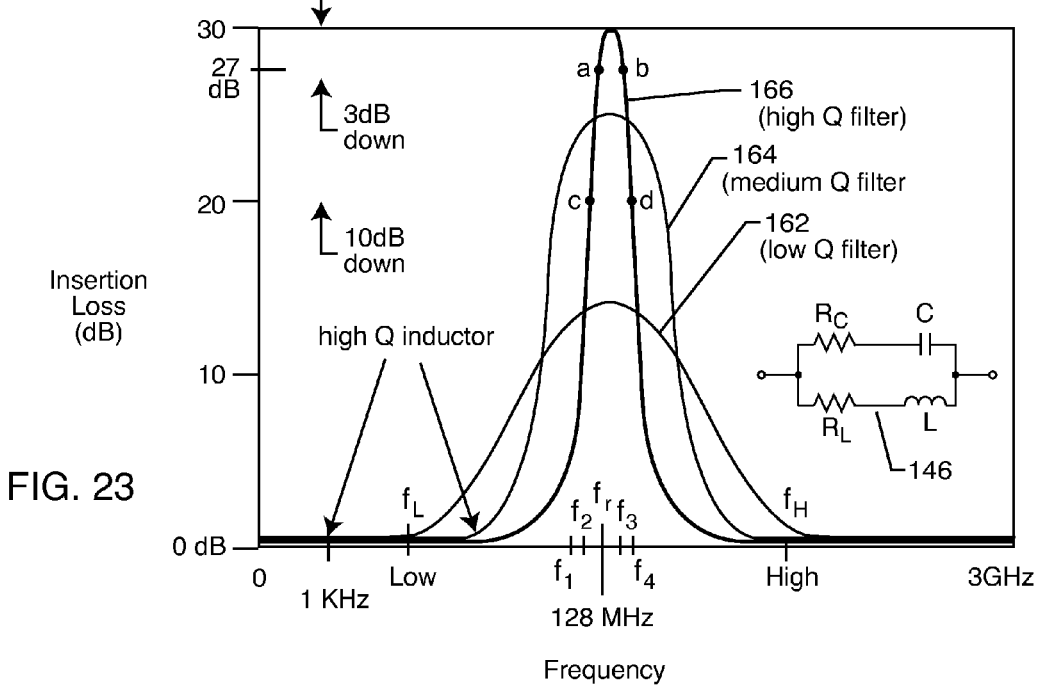
FIG. 23 is graph of insertion loss versus frequency for bandstop filters having differing quality "Q" factors.

Referring now to FIG. 23, the efficiency of the bandstop filter is also measured in terms of a quality factor, Q. The bandstop filter circuit Q is typically expressed using the following equation:

$$Q = \frac{f_r}{\Delta f_{3dB}}$$

Where $f_r$ is the resonance frequency, and $\Delta f_{3dB}$ shown as points a and b in FIG. 23 is the 3 dB bandwidth of the bandstop filter. The 3 dB bandwidth is determined from an insertion loss sweep in a balanced 50-ohm system. It is recognized that an implanted lead source impedance and an AMD input (load) impedance are variable with frequency, lead trajectory and other factors. In other words, it is highly unlikely that an implanted lead source and device load impedance will be 50-ohms. However, to simplify matters and for comparison purposes, the insertion loss curves and resulting 3 dB and 10 dB bandwidths will be calculated and/or measured in a balanced 50-ohm in-vitro (bench top) measurement system. The 3 dB bandwidth is defined the difference in frequency between the insertion loss upper 3 dB down frequency "b" and the lower 3 dB down frequency "a". The upper and lower 3 dB frequencies are generally centered around the resonant frequency of the bandstop filter. These measurements are best conducted using a 50-ohm swept spectrum analyzer or 50-ohm network analyzer of the bandstop filter portion(s) of the implantable lead. Accordingly, the 3 dB bandwidth is $f_3$-$f_2$ and the 10 dB bandwidth is $f_4$-$f_1$.

The 10 dB down points are shown as points "c" and "d" in FIG. 23 and correspond with frequencies $f_1$ and $f_4$. Accordingly, the 10 dB bandwidth is $f_4$-$f_1$ measured either in kHz or MHz. In general, the insertion loss curve can also be equated to an attenuation curve wherein the source and load impedances would be 50 ohms. In practice, the source impedance would be the source impedance of the lead and body tissue and the load impedance would be the input impedance of the AMD itself. Those experienced in the art will realize that the balanced 50-ohm approach defines a repeatable and design comparison test method. For the medium Q filter and the low Q filter, there are also corresponding 3 dB down points and 10 dB down points (not shown for clarity).

Referring once again to FIG. 23, one can see the schematic for the bandstop filter 146 of the present invention including resistors $R_C$ and $R_L$. Resistor $R_C$ represents the equivalent series resistance of the capacitor C, or a discrete series resistor added in series with the capacitor. $R_L$ represents the equivalent series resistance of the inductor L, which is commonly due to the resistance of the coiled wire turns or wire circuit traces of the inductor. $R_L$ could also include a separate discrete chip resistor or other type of resistor added in series with the inductor portion of the bandstop filter 146. Controlling the values of these resistances controls the 3 dB and 10 dB bandwidths and hence the quality factor Q of the bandstop filter.

Both the 3 dB bandwidth and the 10 dB bandwidth can be varied in accordance with the application. For example, if the application is for a very specific situation, for example a dedicated MRI guided catheter lab, then only one MRI scanner is involved. For example, if it is known that only a Siemens 1.5 Tesla MRI scanner of a particular model and known magnet is to be used, then we can be confident of a very specific MRI RF pulsed frequency. The bandstop filter 146 could be designed with relatively narrow 3 dB and 10 dB bandwidths. In this case, the 10 dB bandwidth could be as small as 10 kHz. In this regard it should be borne in mind that the gradient field of the MRI scanner grades the main static field. A way to visualize this is with a patient lying in the supine position on the MRI scanner table. As the gradient field varies, the static magnetic field strength varies from head-to-toe of the patient. This means that the resonant frequency of the protons vary accordingly. In this way, the RF frequency varies thereby obtaining the image slice from the patient. About the narrowest variation is in the order of 10 kHz. On the other hand, if one were to design a bandstop filter 146 for implanted lead applications where multiple MRI scanners (from different manufacturers) needed to be compatible, then a 10 dB bandwidth of 100 kHz minimum would be desirable. In general, in a particularly preferred embodiment, the 10 dB bandwidth would be on the order of megahertz, or a minimum of 500 kHz. By having a 10 dB bandwidth on the order of MHz (0.5 MHz) minimum, one can then be sure that the bandstop filter 146 would be effective over the range of commercially available or labeled 1.5 Tesla MRI scanners. Similar principles apply to 3 Tesla, 5 Tesla and other scanners that have a different static magnetic field strength. In these cases, the RF pulsed frequencies are much higher in frequency and their variation between different manufacturers and also their variation because of the gradient field can be even greater as measured in kHz. In summary, depending upon the application, the 3 dB bandwidth can vary anywhere from 10 kHz to 100 kHz to 0.5 MHz or even to tens of MHz. Similarly, allowing for a "safety margin", the 10 dB bandwidth can vary anywhere from 26 kHz to 200 kHz to 0.5 MHz or even to tens of MHz.

Referring once again to FIG. 23, one can see that at very low frequencies, such as shown by $f_L$, it is important that the bandstop filter 146 represent a very low impedance. This is because the bandstop filter must pass low frequency pacing and biologic sensing signals with very little attenuation. The same is not true of very high frequencies as shown by $f_H$. In this case it would not matter if the bandstop filter offered additional attenuation since there are no biological signals in this range (just high frequency EMI).

Accordingly, the "Q" or quality factor of the bandstop circuit 146 is very important.

In the present invention, the overall Q of the bandstop filter is selected to balance impedance at a selected (resonant center) frequency versus frequency bandwidth characteristics. What this means is, is that the Q of the bandstop filter be sufficiently low so that the 3 dB bandwidth of the bandstop filter is sufficiently wide to attenuate the range of MRI RF pulsed frequencies of interest. On the other hand, the Q of the bandstop filter is balanced or traded off against the impedance of the bandstop filter at resonance. For example, (1) a very high Q bandstop filter will have a very high amount of attenuation (greater than 40 dB) at both at its resonance center frequency and also at its 3 dB bandwidth points, however, (2) the 3 dB bandwidth will be so narrow in frequency (less than 10 kHz) that the high Q bandstop filter will not provide adequate attenuation across a broad enough range of MR RF frequencies (such range of frequencies can result due to variations among scanner static magnetic strengths and/or variations in RF frequency due to "grading" by the MRI gradient field(s)). On the other hand, (1) a very low Q bandstop filter will offer only a very small amount of attenuation (less than 10 dB) at both its resonant center frequency and at its 3 dB bandwidth points, but (2) it will have a relatively wide 3 dB bandwidth which is generally greater than several megahertz. For example, for implanted leads that may be exposed to one particular 1.5 Tesla MRI scanner, a bandstop filter is necessary wherein the overall Q of the bandstop filter is selected to balance impedance at a selected frequency versus frequency bandwidth characteristics such that the bandstop filter offers a minimum of 10 dB of attenuation at its resonant center frequency and also that it have a 3 dB bandwidth of at least 10 kHz. For MRI compatibility, other implanted lead applications may require a bandstop filter attenuation of greater than 20 dB at the resonant frequency and a 3 dB bandwidth of greater than 0.5 MHz. The attenuation of the bandstop filter at its resonant center frequency is a function of the L-C bandstop filter 3 dB bandwidth and its L/C ratio. In general, higher inductance gives higher attenuation at resonance. However, for a given lead geometry, there is a practical limit to the amount of inductance available to the designer. In summary, for a particular implantable lead system, the overall Q of the bandstop filter is selected to balance impedance at a selected (resonant) frequency versus frequency bandwidth characteristics.

As mentioned, it is desirable to have a very low loss circuit at low frequencies such that the biological signals not be undesirably attenuated. The quality factor Q not only determines the loss of the filter, but also affects its 3 dB and 10 dB bandwidths. If one does a plot of the filter response curve (Bode plot), the 3 dB and 10 dB bandwidths determine the attenuation curve, shape and how sharply the filter response will rise and fall. With reference to curve 166 of FIG. 23, for a bandstop filter 146 that is resonate at 128 MHz, an ideal response would be one that had infinite attenuation at 64 MHz, but had zero attenuation at low frequencies below 1 kHz. Obviously, this is not possible given the space limitations and the realities of the parasitic losses within components. In other words, it is not possible (other than at cryogenic temperatures) to build an inductor that has zero internal resistance. Accordingly, the practical realization of a circuit, to accomplish the purposes of the present invention, is a challenging one. This is particularly true when one also considers that the bandstop circuit must also be miniature, highly reliable, and completely biocompatible.

The performance of the circuit is directly related to the efficiency of both the inductance L and the capacitance C; the less efficient each component is, the more heat loss that results, and this can be expressed by the addition of resistor elements, $R_C$, and $R_L$ to the ideal circuit diagram. On the other hand, the effect of lower Q in the bandstop circuit 146 is to broaden the resonance peak about the resonance frequency. By deliberately using a low Q capacitor and/or inductor, one can broaden the resonance such that a moderately high impedance (attenuation) is presented at multiple MRI RF frequencies. As one can see, there are a number of design tradeoffs. Controlling the amount of resistance in the inductor $R_L$ is particularly important for an implantable defibrillator lead. The reason for this is the lead has to conduct a very large pulse current when a patient is defibrillated. This current must flow through the bandstop filter as well as the lead. In a particularly preferred embodiment, diodes are used to divert the current around the bandstop filter. A more thorough description of transient voltage protected bandstop filters is described in US. Patent Application Ser. No. 2010/0023095 to Stevenson et al., the contents of which are incorporated herein by reference.

Referring again to FIG. 23, one can control both the 3 dB bandwidth and the 10 dB bandwidth by controlling the amount of resistance $R_C$ and $R_L$ in the bandpass filter circuit 146. One must be careful not to let the resistance in series with the inductor be too large or biological frequencies will be attenuated. The reason for this is that at very low frequencies (below 1 kHz), the inductive reactance tends to be very low (approximate zero). At the same time, at very low frequencies the capacitive reactance tends to look infinite. Accordingly, for proper operation of delivering pacing pulses or sensing biological activity, the resistor value $R_C$ really does not matter much. Accordingly, a good way to control the Q of the bandstop filter 146 is to establish resistance $R_L$ that is consistent with the parasitic resistances of inductor windings or turns and also carefully control the capacitor ESR. However, one must also control the resistive loss $R_L$ of the inductor L because if the inductor's resistance gets too high, excessive heating of the bandstop filter could occur. This is because there is a high frequency current that oscillates at the MRI pulsed frequency between the capacitor's C electric field and the inductor's L magnetic field. This circulating current can create heating about the bandstop filter in one of two ways: 1) by $I^2R$ heating in either resistance $R_L$ or $R_C$ (or both), or, 2) by eddy current losses in the hermetic or shield housing that surrounds the bandstop filter. Accordingly, a careful balance between component design and bandstop filter Q must be achieved.

The Lamour equation tells us that the frequency of the pulsed RF field is equal to the MRI constant times the static magnetic field strength of the clinical scanner in Teslas. The Lamour constant is 42.56 and the resulting RF frequency is approximately 64 MHz for a typical prior art 1.5-Tesla hydrogen scanner (42.56 times 1.5=63.84 MHz). In any particular MRI scanner, the RF-pulsed frequency does vary as the gradient field grades the static magnetic field. In addition, not all marketing-labeled 1.5-Tesla scanners are the same. There is considerable variation in the static magnetic field strength from different manufacturers. This results in several hundreds of kilohertz or even a half megahertz of difference between the RF pulsed frequency between the various scanner manufacturers. For MRI scanners with stronger magnets, such as 3 Tesla, the RF frequency is higher and the variation of RF frequency between various manufacturers is greater. In this case, the 10 dB bandwidth of the bandstop filter would have to be on the order of tens of MHz (as much as 10 MHz). Accordingly, the bandstop filter 146 is designed to be resonant at a center frequency, $f_r$, representing the center of a range of RF pulsed frequencies. As shown in FIG. 23, a resistance element $R_C$, $R_L$ or both, is added in order to increase the 3 Db and 10 dB bandwidth of the L-C bandstop filter 146. Referring once again to FIG. 23, one can see the attenuation curve for a high Q filter 166, a medium Q filter 164, and a low Q filter 162. The medium Q filter would work for many applications, but the attenuation of the low Q filter generally would not be adequate to be sure that excessive heating at a distal electrode would not occur. In the present invention, the desired curve shapes are 164 or 166. To put this in perspective, for an ideal bandstop filter (meaning that $R_C$ and $R_L$ are both zero), the filter response curve would look like a straight up and down line (not shown) centered above $f_r$. This would, of course, be so narrow that it would be both impractical (other than at cryogenic temperatures) to build and impractical for use over a range of MRI scanners. This resistance element can be a discrete resistor or it can be formed from the leads or circuit traces as a parasitic element that forms the inductance L itself. For simplicity, this resistance element is not shown in some drawings. However, it will be understood that the bandstop filter is designed to attenuate over a range of MRI RF pulsed frequencies on the order of tens of kilohertz, hundreds of kilohertz, or even tens of megahertz.

Figure 24:
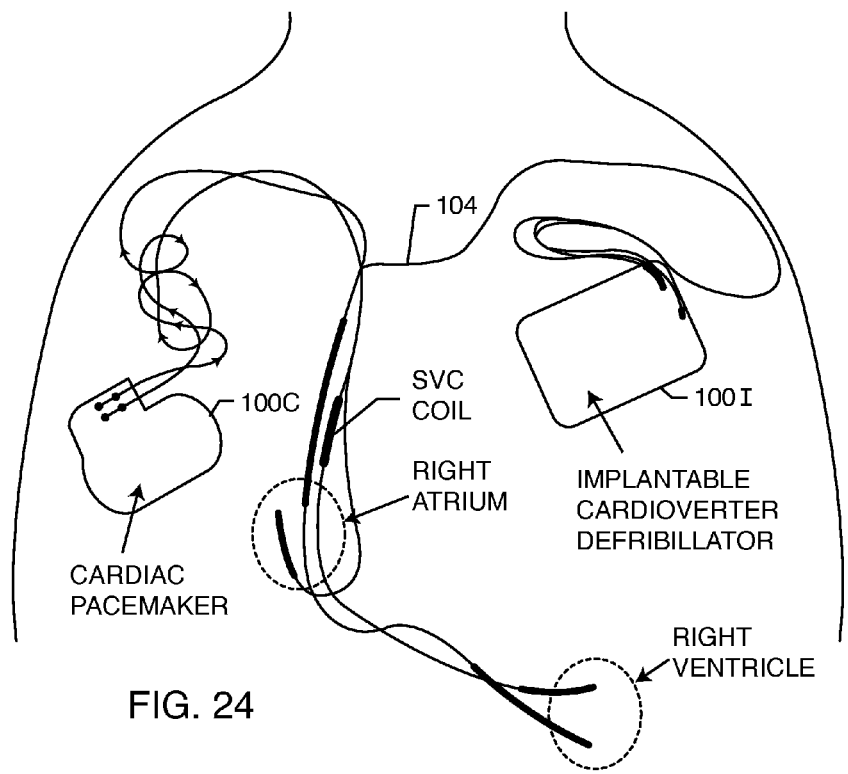
FIG. 24 is a tracing of an exemplary patient x-ray showing an implanted pacemaker and cardioverter defibrillator and corresponding lead wire system.

FIG. 24 is a tracing of an actual patient X-ray. This particular patient required both a cardiac pacemaker 100C and an implantable cardioverter defibrillator 100I. The corresponding lead wire system 104, as one can see, makes for a very complicated antenna and loop coupling situation. The reader is referred to the article entitled, "Estimation of Effective Lead Loop Area for Implantable Pulse Generator and Implantable Cardioverter Defibrillators" provided by the AAMI Pacemaker EMC Task Force.

Referring again to FIG. 24, one can see that from the pacemaker 100C, there is an electrode in both the right atrium and in the right ventricle. Both these involve a Tip and Ring electrode. In the industry, this is known as a dual chamber bipolar lead wire system. Accordingly, the bandstop filters 146 of the present invention would need to be placed at least in the distal Tip in the right atrium and the distal Tip in the right ventricle from the cardiac pacemaker. One can also see that the implantable cardioverter defibrillator (ICD) 100I is implanted directly into the right ventricle. Its shocking Tip and perhaps its super vena cava (SVC) shock coil would also require a bandstop filters of the present invention so that MRI exposure cannot induce excessive currents into the associated lead wire system (S). Modern implantable cardioverter defibrillators (ICDs) incorporate both pacing and cardioverting (shock) features. Accordingly, it is becoming quite rare for a patient to have a lead wire layout as shown in the X-ray of FIG. 24. However, the number of electrodes remain the same. There are also newer combined pacemaker/ICD systems which include biventricular pacemaking (pacing of the left ventricle). These systems can have as many as 9 to even 12 lead wires.

Figure 25:
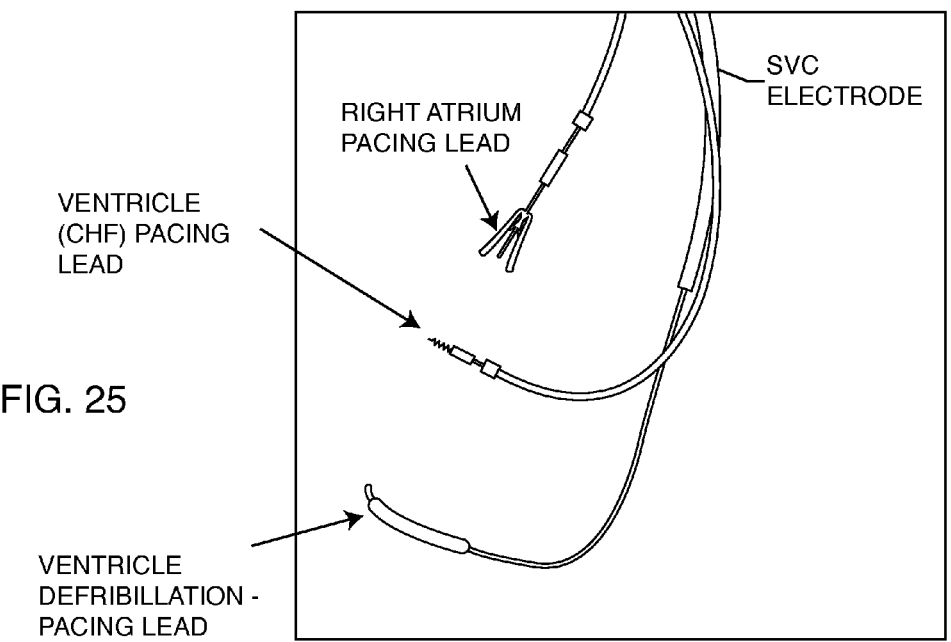
FIG. 25 is a line drawings of an exemplary patent cardiac x-ray of a bi-ventricular lead wire system.

FIG. 25 is a line drawing of an actual patient cardiac X-ray of one of the newer bi-ventricular lead wire systems with various types of electrode Tips shown. The new bi-ventricular systems are being used to treat congestive heart failure, and make it possible to implant leads outside of the left ventricle. This makes for a very efficient pacing system; however, the lead wire system 104 is quite complex. When a lead wire system 104, such as those described in FIGS. 8, 9, 10 and 11, are exposed to a time varying electromagnetic field, electric currents can be induced into such lead wire systems. For the bi-ventricular system, bandstop filters 146 would be required at each of the three distal Tips and optionally at Ring and SVC locations.

Figure 26:
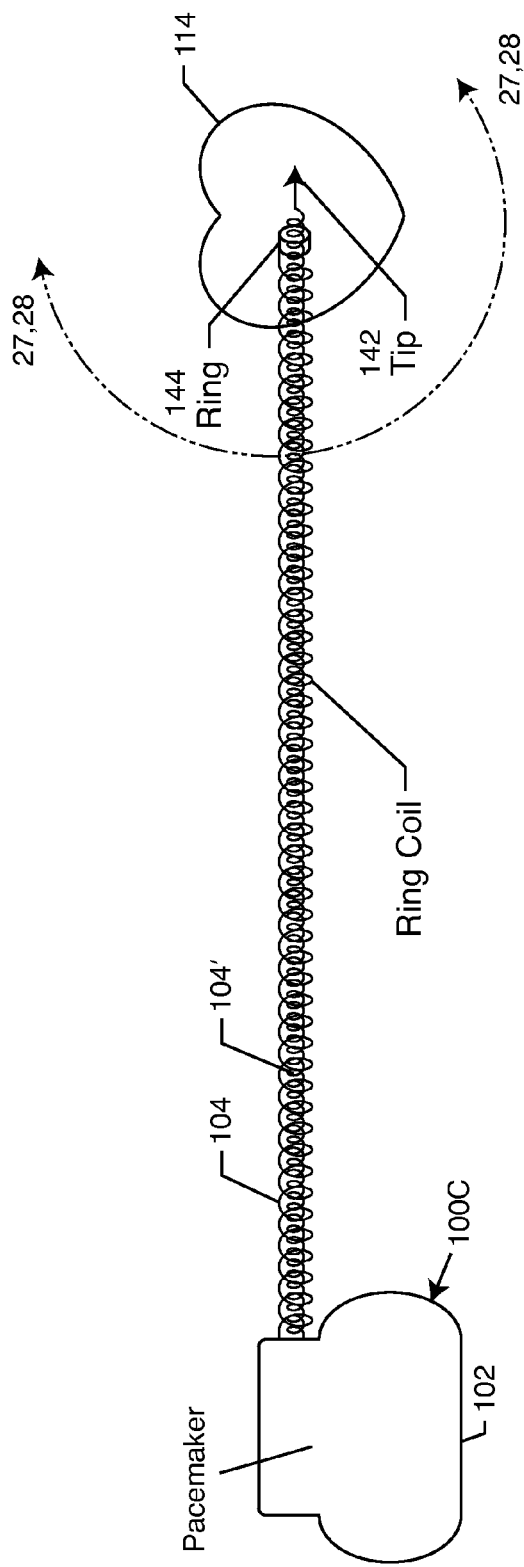
FIG. 26 illustrates a bipolar cardiac pacemaker lead wire showing the distal Tip and the Ring electrodes.

FIG. 26 illustrates a single chamber bipolar cardiac pacemaker lead wire showing the distal Tip 142 and the distal Ring 144 electrodes. This is a spiral wound system where the Ring coil 104 is wrapped around the Tip coil 104'. There are other types of pacemaker lead wire systems in which these two leads lay parallel to one another (known as a bifilar lead system).

Figure 27:
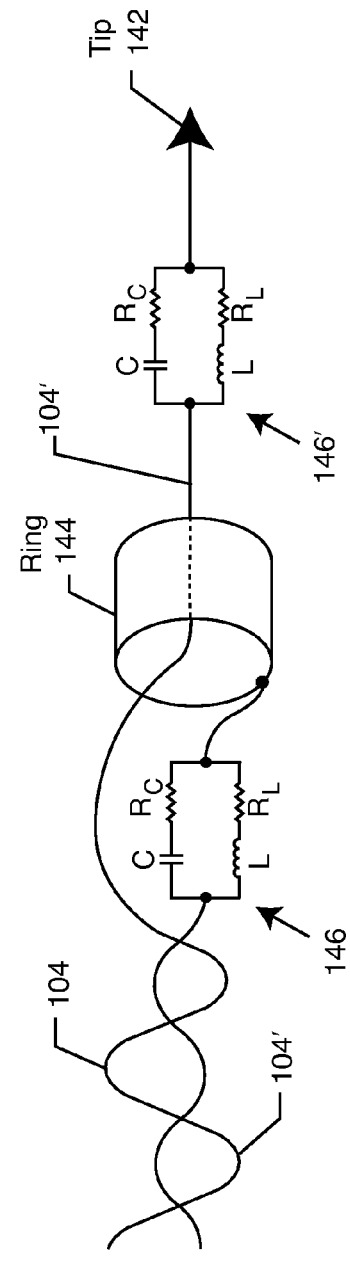
FIG. 27 is an enlarged, fragmented schematic illustration of the area illustrated by the line 27-27 in FIG. 26.

FIG. 27 is a schematic illustration of the area 27-27 in FIG. 26. In the area of the distal Tip 142 and Ring 144 electrodes, bandstop filters 146 and 146' have been placed in series with each of the respective Tip and Ring electrode circuits. Accordingly, at MRI pulsed frequencies, a high impedance will be presented thereby attenuating the flow of undesirable RF current.

Figure 28:
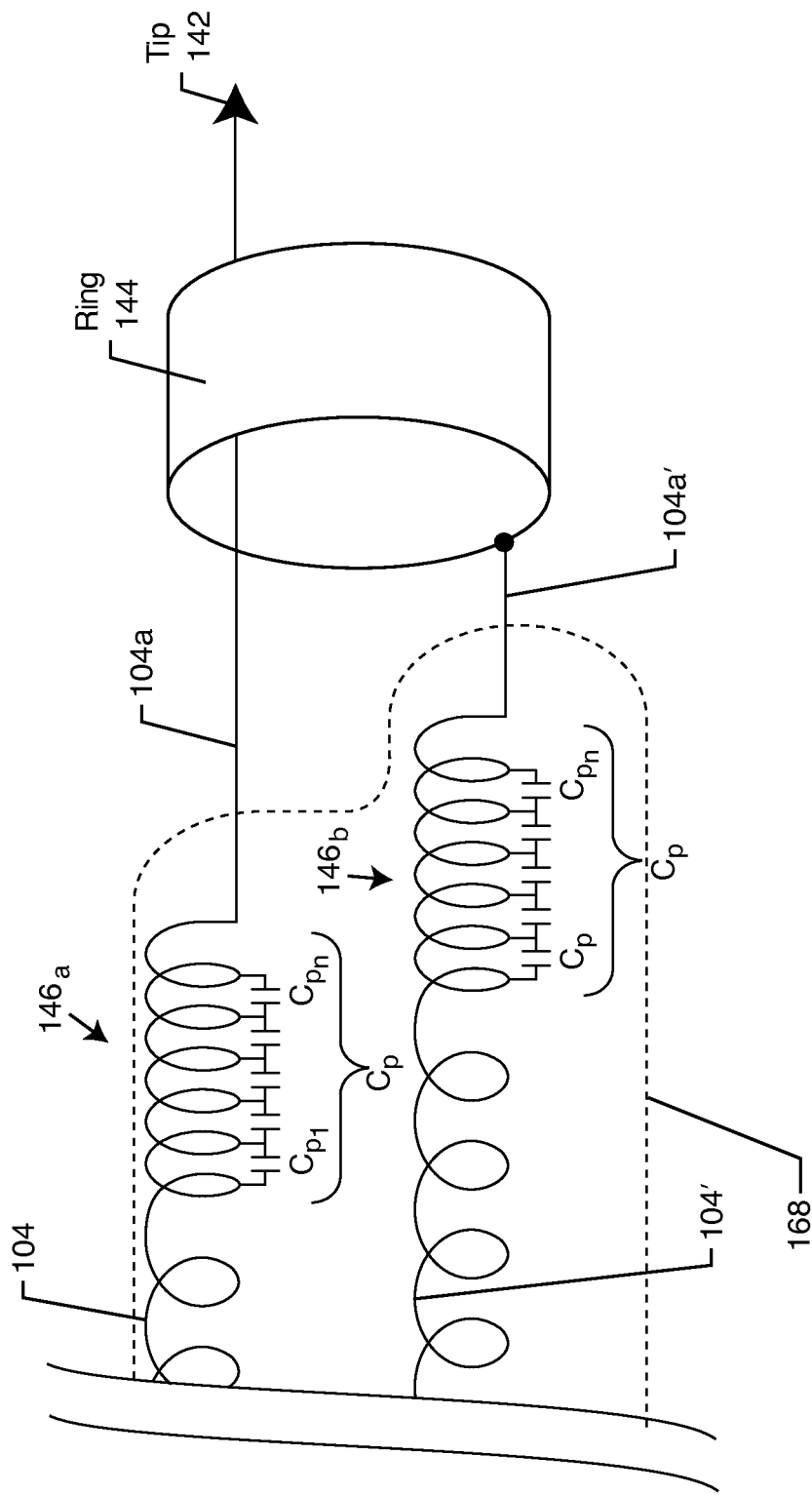
FIG. 28 is similar to FIG. 27, but illustrates bandstop filters formed by lead inductance and parasitic capacitance, disposed within an insulative sheath.

FIG. 28 is a schematic illustration of the area 28-28 from FIG. 26. To the left of the bandstop filters 146$_a$ and 146$_b$, the implantable lead conductors 104 and 104 can either be coiled as shown or straight (filer) or the like. By way of background, the individual conductors of prior art implanted leads are usually not individually insulated. In the prior art, the lead body does have an overall insulation covering 168. In prior art uninsulated adjacent lead conductors the coils tend to short out in many places, particularly when the lead is going around sharp, torturous bends in a venous system. In accordance with the present invention and as shown in FIG. 28, there are two inductive coil-parasitic capacitance bandstop filter sections 146$_a$ and 146$_b$ in series with the coiled implanted lead conductors 104 and 104', wherein the inductive conductors have an insulative coating with a specific dielectric constant material coated over them. These inductive coils L are generally closely spaced (with a predetermined spacing) such that a distributed capacitance Op is formed between the adjacent coils/windings of the inductor. Along the length of both bandstop filters 146$_a$ and 146$_b$ an inductance (inductor) is formed along with the parallel parasitic (or stray) capacitance Cp from turn to turn in order to form the bandstop (tank) filters of the present invention.

As used further herein, the terms "parasitic capacitance" and/or "stray capacitance" and/or "capacitance" are synonymous and refer to the capacitance formed between the adjacent turns of an inductive coil L. In addition, as used herein, the terms "parasitic capacitance" and/or "stray capacitance" and/or "capacitance" can also refer to the total capacitance formed in the inductor coil L which is the sum of all of the individual turn to turn capacitances. Electrically, in FIG. 28, the total capacitance $C=C_{p1}+C_{p2}+\ldots C_{pn}$ appears in parallel with the total inductance L of the inductive coil to form the parallel resonant L-C bandstop filters 146 and 146' of FIG. 27 of the present invention.

In a preferred embodiment, these inductive coil-parasitic capacitance self-resonant bandstop filters 146 and 146' are located at, near or within the distal electrodes of the implantable lead. In the case of FIG. 28, these are the bipolar Tip and/or Ring electrodes 142 and 144 of a typical cardiac pacemaker. Each bandstop filter 146$_a$ and 146$_b$ is a single inductive coil component with enough total parasitic capacitance to be self-resonant at the MRI RF pulsed frequency or frequency range. Accordingly, FIG. 27 is also the equivalent circuit schematic of FIG. 28. The capacitance C, as illustrated in FIG. 27, is the sum of the parasitic capacitances $C_{P1}$ through $C_{pn}$. In this case, "n" indicates that any number of inductor coil turns, as desired, can be created for the inductive coil portion of the leads of 104 and 104'. The self-resonant inductor bandstop filter portions of the implanted leads 104 and 104' can be formed at the same time the overall lead conductor is formed, or they may be prefabricated (coiled) and then installed in one or more locations along the lead by laser welding attachment or the like. In an embodiment, the dielectric insulation that coats the coils of the inductive-parasitic capacitance bandstop filter portions may also coat the entire lead conductor coils (this would facilitate easy fabrication in some cases).

Figure 29:
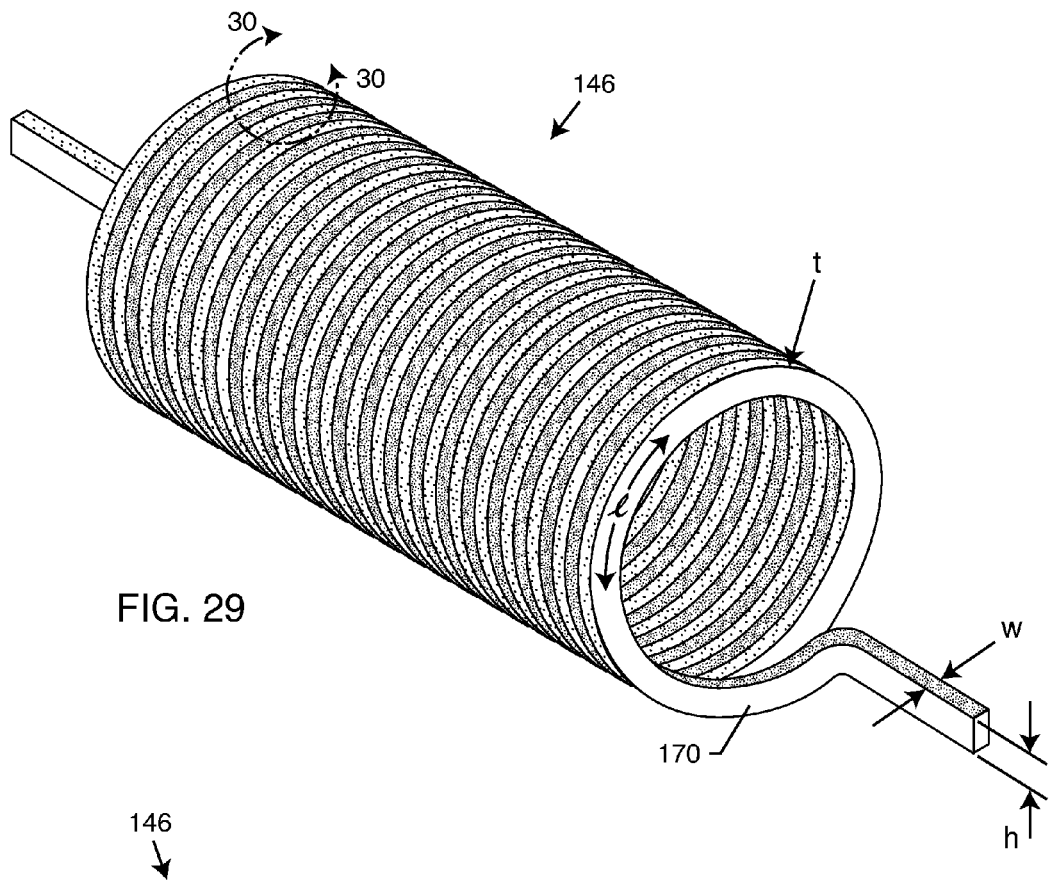
FIG. 29 is an isometric view of an inductive-parasitic capacitance bandstop filter of the present invention.

FIG. 29 is an isometric view of a round inductive coil-parasitic capacitance bandstop filter 146 of the present invention. The bandstop filter 146 is formed from one continuous wound elongated electrical conductor 170. Different shadings are shown to illustrate each individual turn and the fact that the coil turns are preferably closely spaced. In a particularly preferred embodiment, the elongated conductor 170 is of square or rectangular cross-section. The elongated conductor 170 could also be a round cross-section except that this tends to reduce the parasitic capacitance area and may also cause undesirable variability in the parasitic capacitance value. The center of the inductive coil-parasitic capacitance bandstop filter 146 is preferably left hollow to facilitate transvenous guidewire insertion. Hollow bandstop filters for guidewire insertion are described in U.S. Pat. No. 7,702,387, the contents of which are incorporated herein by reference.

Figure 30:
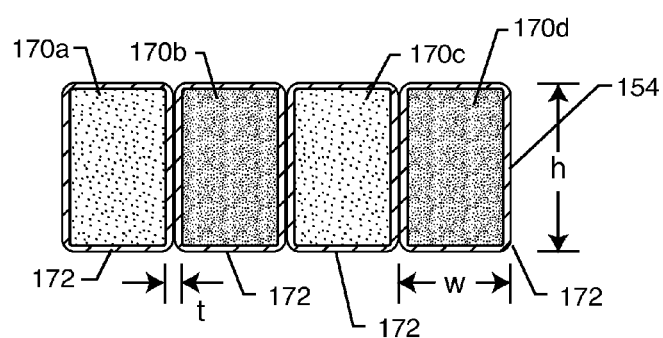
FIG. 30 is a sectional view taken generally from section 30-30 of FIG. 29, showing the adjacent inductor turns.

FIG. 30 is a sectional view generally taken from section 30-30 of FIG. 29. Shown are adjacent turns 170$a$-170$d$ of the electrical conductor 170 that have a dielectric coating 172 over them. This dielectric coating 172 is important for several reasons: 1) so that the individual turns of the inductive coil 170 do not short out to each other; 2) to provide a material with a uniform thickness and dielectric constant so that a significant and consistent parasitic capacitance Cp is formed; and (3) the dielectric coating material 172 has a much higher dielectric constant than air, thereby allowing one to increase or tune the parasitic capacitance Cp between adjacent coils.

Figure 31:
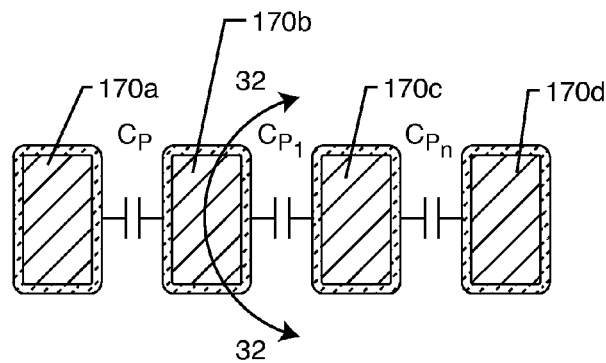
FIG. 31 is an electrical diagrammatic illustration of the structure of FIG. 30, illustrating turn-to-turn parasitic capacitance.

FIG. 31 is an electrical diagrammatic illustration of the structure of FIG. 30. Shown are the parasitic capacitances $C_P$, $C_{P1} \ldots C_{Pn}$. These capacitances end up in parallel with the overall inductance of the coil found between adjacent windings 170$a$-170$d$ of the inductive coil to form a total capacitance in parallel with the overall inductance which forms the bandstop filter 146 of the present invention.

The adjacent coil segments 170$a$, 170$b$, 170$c$, and 170$d$ are shown spaced apart in FIG. 31 so that the parasitic capacitances $C_p$ $C_{p1}$ and $C_p''$ can be shown. In actual embodiments, the coil segments would be closely spaced as shown in FIG. 29.

Figure 32:
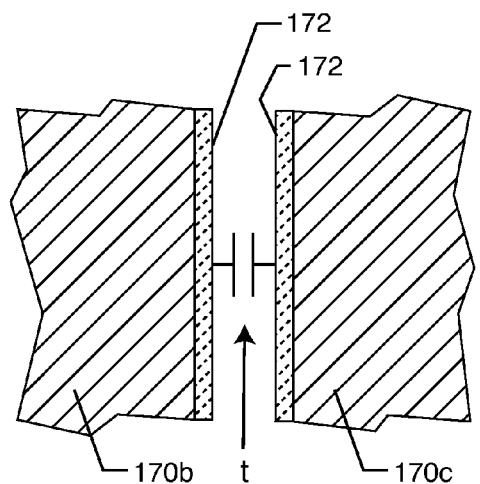
FIG. 32 is an enlarged, fragmented sectional view of the area designated by the line 32-32 in FIG. 31.

FIG. 32 is an enlarged, fragmented sectional view of the area designated by line 32-32 in FIG. 31. In general, the dielectric coatings 172 would be pressed closely together and touching each other (to minimize or eliminate an air gap). In a preferred embodiment, the dielectric coating 172 would be overmolded or coated over the entire inductor coil 170 to provide dimensional stability, electrical isolation from body fluids and to eliminate any air gap completely. Elimination of the air gap maximizes the parasitic capacitance Cp. This is because air has a low dielectric constant (k=1) relative to the dielectric coating 172 which has a dielectric constant of 2 to 30. The coil turns are shown spaced apart widely in FIG. 32 only to illustrate the parasitic capacitance Cp.

Referring to FIGS. 31 and 32, the amount of parasitic capacitance Cp is determined by the overlap area (effective capacitance area or ECA) of the repeating adjacent coil turns 170. One can increase the ECA and hence the amount of parasitic capacitance Cp by increasing the coil height "h" (shown in FIGS. 29 and 30) and/or by the increasing the overall length "l" of the elongated conductor 170. The length l (FIG. 29) can be controlled by inductor coil radius and also coil pitch (a larger pitch increases the length l, and therefore increases both the ECA and the parasitic capacitance Cp. If one were to unwind and lay flat the inductor coil 170, the ECA would be approximately the height h of the elongated conductor times its stretched out length l. The length l could also be approximated wherein length $l=2\pi r_m n$, where $r_m$ is the mean coil radius and n is the number of coil turns (pitch must also be accounted for). The width "w" of the elongated conductor 170 does not affect the turn to turn parasitic capacitance $C_p$ in a significant way (there are fringe effects), however, the width w does significantly affect the resistance $R_L$ of the inductor coil and therefore the overall Q of the bandstop filter 146. The capacitance value is also related to the dielectric constant and thickness of the dielectric coating 172. Reducing the dielectric thickness increases the capacitance value significantly. These relationships are expressed ideally by the following equation:

$$C = \frac{n\kappa A}{t},$$

where "n" is the number of adjacent coil turns 170, "k" is the dielectric constant of the dielectric coating 172, "A" is the effective capacitance area ECA (conductor height "h" times elongated coil conductor 170 length l) and "t" is the total thickness of the dielectric coating 172 between opposing coils. For the overlapping faces of the coil turns of the inductive coil-parasitic capacitance bandstop filter 146, the ECA is relatively large since it includes the entire overlap area. This gives the designer many degrees of freedom in selecting and controlling the parasitic capacitance Cp value.

The inductor coil resistance $R_L$ is determined by a number of factors. DC resistance (or series resistance $R_s$) is given by the formula $R_L=\rho l/A$ wherein "ρ" is the resistivity of the elongated coil conductor material, "l" is the stretched out length of the inductor coil 170 and "A" is the cross-sectional area of the elongated conductor that forms the inductor coil 170. As shown in FIG. 30, the area "A", for a square or rectangular wire coil cross section, is determined by its height "h" times its width "w". For a circular conductor wire, the area A is equal to $\pi r^2$ where r is the radius of the wire. The general equation for resistance (in ohms) of the square or rectangular conductor coil of the preferred embodiment is:

$$R_s = \frac{\rho l}{hw}$$

Figure 33:
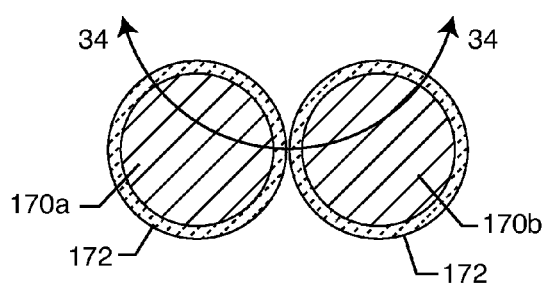
FIG. 33 is similar to FIG. 30, and illustrates an alternative embodiment where the conductor forming the inductor is round instead of square or rectangular.
Figure 34:
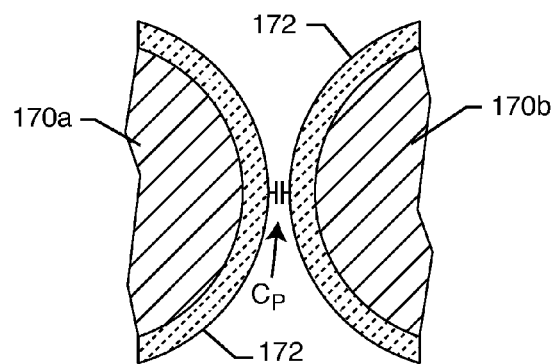
FIG. 34 is an enlarged fragmented sectional view taken generally along the line 34-34 from FIG. 33 illustrating the turn-to-turn parasitic capacitance.

FIG. 33 is similar to FIG. 30 and is substantially the same as FIG. 31, except that the conductor 170 is round (no longer rectangular or square) in cross-section. The conductor shown in FIG. 33 is a conventional round wire which could be used in the present invention but is relatively undesirable. As shown in FIG. 34, the effective capacitance (ECA) overlap area would be very small. Not only would the resulting parasitic capacitance Cp be very small, but it would also be highly variable. Any slight variations in winding compactness or alignment would cause the capacitance value Cp to vary significantly. Accordingly, the present invention preferably comprises an elongated conductor 170 that forms the inductive coil-parasitic capacitance bandstop filter 146 be of either rectangular or square wire, coated, molded or interleaved with a dielectric coating 172. By controlling the geometry (overall conductor length "l" and/or height "h" of the elongated conductor 170, one can control the parasitic capacitance that is formed. In other words, the designer can control the bandstop filter resonant frequency by controlling both the total inductance and the total amount of parasitic capacitance that is formed. Importantly, the designer can also control the Q and resulting 3 dB bandwidth at resonance of the inductive-parasitic capacitance bandstop filter 146.

The primary factor in controlling the inductive-parasitic capacitance bandstop filter Q is to control the resistance of the elongated conductor 170 that forms the inductor coil. The resistivity of the wire ρ (rho) is one of its primary material properties. One can choose from various conductive materials to form the elongated conductor 170. The resistance is also determined by the overall length "l" of the elongated conductor 170 and its cross-sectional area.

Figure 37:
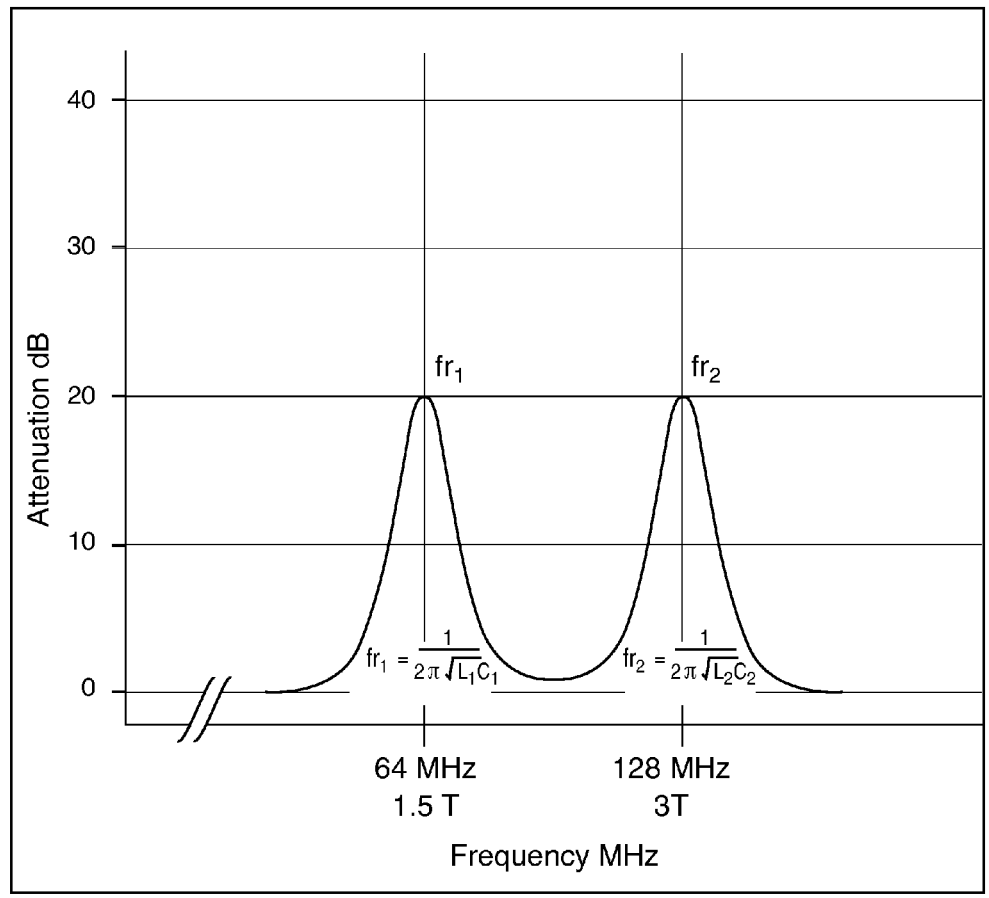
FIG. 37 is a graph of attenuation of the inductive coil-parasitic capacitance bandstop filter of FIGS. 29 and 35 versus frequency.

In additional to turn to turn overlap area (ECA), one also controls the parasitic capacitance Cp by proper selection of the type of dielectric coating 172 and/or, the dielectric thickness. This can be used to control second, third of even n resonant frequencies as well. A primary determining factor of the parasitic capacitance Cp is the effective capacitance area (ECA) which is determined by the amount of planar surface overlap between the adjacent turns of the inductive coil-parasitic capacitance bandstop filter 146. Various inductor segments of the inductive coil-parasitic capacitance bandstop filter 146 can all be of the same cross-sectional shape conductor. On the other hand, various coil segments could have a different cross-sectional area of wire and a different number of turns. One could also vary the dielectric coating 172 type and thickness in each segment in order to obtain a different value of parasitic capacitance Cp. This affords the designer many degrees of freedom in controlling both the inductance and the Q of each resonant section such that multiple resonances can be achieved. (ref. FIG. 37).

There are several ways to apply the dielectric coating 172. One way would be to coat the entire elongated conductor wire 170 before forming the coil wound inductor segments. Another way to do this would be through carefully controlled winding processes where the entire assembly was subsequently dipped or coated with a dielectric material such as vacuum deposited parylene. In another embodiment, a dielectric film could be disposed between or molded over the conductor 170 or the wound inductor coils.

There are various suitable dielectric insulative materials such as Polyimide, aromatic polyimide, liquid crystal polymer, PTFE, PEEK, ETFE, Parylene, tantalum oxides, iridium oxides, niobium oxides, hafnium oxides, ruthenium oxides, any nano-dielectric coating, PFA, FEP, Polyurethane, polyurethane with self-bonding overcoat, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, thermoplastic compounds, polyvinylchloride (PVC), polyolefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PFA, Halar ECTFE, PTFE Teflon, PTFE Teflon film, XLPE & XLPVC, silicone rubber, Polyimide Kapton film, Polyester Mylar film, Kaladex PEN film, crosslinked polyalkene, and various other types of polymer or ceramic materials. Higher dielectric constants can be achieved by nano materials such as nano ceramic powders.

TABLE I

Other suitable dielectric insulative materials.

| Material | Dielectric constant (k) |
| --- | --- |
| $SiO_2$ | 3.9 |
| $Si_3N_4$ | 7 |
| $Al_2O_3$ | 9 |
| $Y_2O_3$ | 15 |
| $La_2O_3$ | 30 |
| $Ta_2O_5$ | 26 |
| $TiO_2$ | 80 |
| $HfO_2$ | 25 |
| $ZrO_2$ | 25 |

Figure 35:
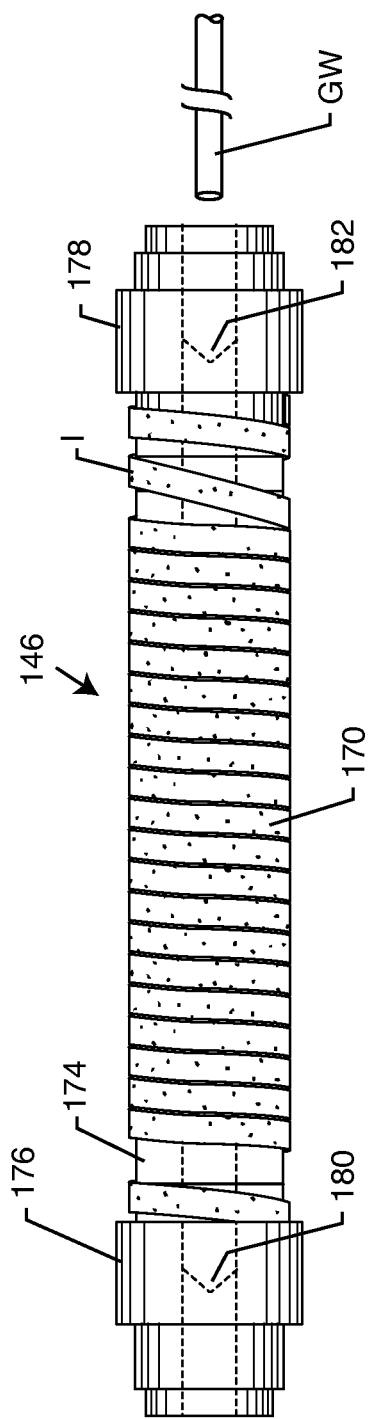
FIG. 35 is an elevational view of the inductive-parasitic capacitance bandstop filter with end caps for convenient mechanical and electrical connection in series with an implanted lead.

FIG. 35 illustrates the inductive coil-parasitic capacitance bandstop filter 146 previously illustrated in FIGS. 28 and 29 with a non-conductive and non-ferromagnetic mandrel 174 and end caps 176 and 178 for convenient mechanical and electrical connection of the inductive coil-parasitic capacitance bandstop filter in series into one or more conductors of an implantable lead of an AMD. The center of the mandrel 174 is preferably hollow to facilitate convenient guide wire transvenous insertion. There are optional valves 180 and 182 which prevent ingress of body fluids during the insertion process. Hollow bandstop filters for transvenous insertion are described in U.S. Pat. No. 7,702,387.

Figure 51:
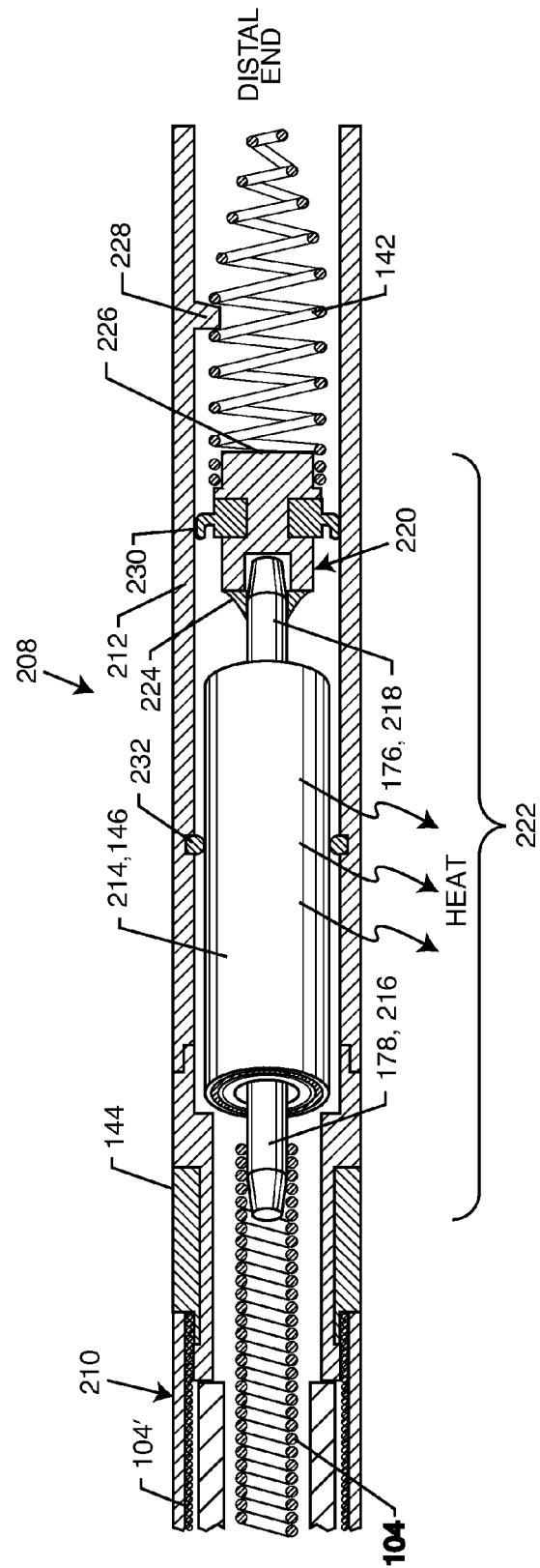
FIG. 51 is a sectional view of an active fixation electrode assembly embodying an inductive coil-parasitic capacitance bandstop filter with seals to prevent ingress of body fluids.

An implantable lead may be comprised of material MP35N which is easily laser welded to mandrel end caps 176 and 178. The inductive coil-parasitic capacitance bandstop filter 146 of the present invention is disposed between these two end caps. End cap 176 would be in series with a distal electrode 140 in contact with body tissues. The inductive coil-parasitic capacitance bandstop filter 146 of the present invention can be disposed anywhere along the length of the implanted lead 104. However, in a particularly preferred embodiment, it is disposed at, near or within the lead distal electrode(s) 140. As shown in FIG. 51, an active fixation tip electrode assembly may be electrically and mechanically connected to end cap 178, 216.

Figure 36:
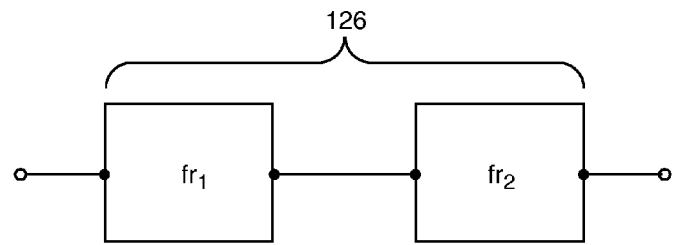
FIG. 36 is an alternate schematic diagram of the inductive coil-parasitic capacitance bandstop filter of FIGS. 28, 29 and 35, illustrating that the bandstop filter may have multiple resonances at $f_{r1}$ and $f_{r2}$.

FIG. 36 is an alternate schematic diagram of the inductive coil-parasitic capacitance bandstop filter 146 of FIGS. 28, 29 and 35 illustrating that the inductive coil-parasitic capacitance bandstop filter may have multiple resonances at $fr_1$ and $fr_2$ or any number of additional resonances $f_n$. For example, the inductive coil-parasitic capacitance bandstop filter 146 can be designed to be resonant at both 64 MHz (1.5-Tesla MRI) and 128 MHz (3-Tesla MRI). Accordingly, this would provide a very high impedance in the implanted lead during patient exposure to either one of these commonly available MRI scanners. Referring once again to FIG. 29 and FIG. 30, one can see that by varying the dielectric material or the dielectric thickness of coating 172 in various sections of the inductive coil-parasitic capacitance bandstop filter 146, one can create a different parasitic capacitance for each section. One can also vary the turn to turn coil ECA, the turn radius and the turn pitch. Accordingly, multiple resonances can be achieved.

FIG. 37 is a graph of attenuation of the inductive coil-parasitic capacitance bandstop filter 146 of FIGS. 29, 35 and 36 versus frequency in MHz. As one can see, there is a resonant peak at both $fr_1$ and $fr_2$ corresponding to 64 MHz and 128 MHz. In both cases, the impedance of the inductive coil-parasitic capacitance bandstop filter 146 is quite high which results in an attenuation value exceeding 10 dB. Through careful design, any number of resonant frequency peaks can be created.

Figure 38:
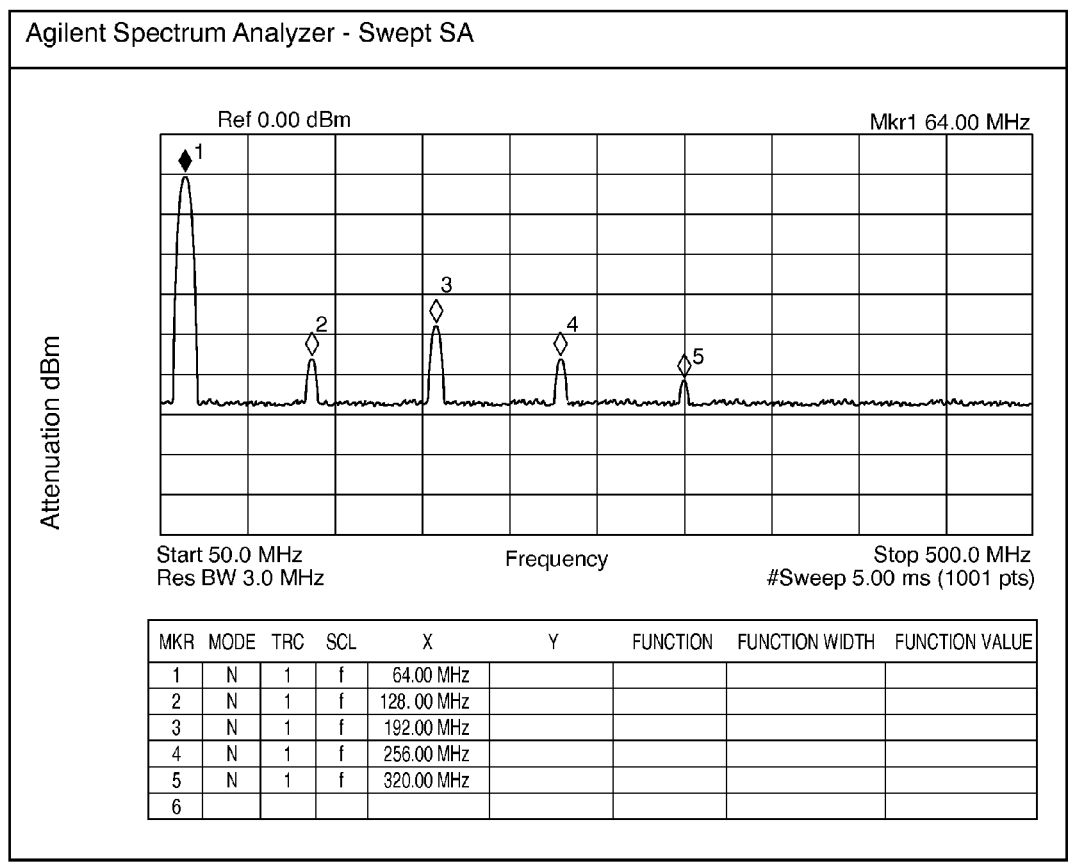
FIG. 38 is a spectrum analyzer scan taken from an RF probe located inside a 1.5 Tesla clinical MRI scanner.

FIG. 38 is a spectrum analyzer scan taken from an RF probe located inside a 1.5 Tesla clinical MRI scanner. The primary RF pulsed frequency is shown at marker 1 as 64 MHz. The harmonics of the RF pulsed frequency are generally not specified or controlled by MRI manufacturer specifications. Accordingly, there is a harmonic (marker 2) at 128 MHz, a harmonic (marker 3) at 192 MHz, a harmonic (marker 4) at 256 MHz and even a harmonic at 320 MHz (marker 5). The primary RF pulsed frequency (64 MHz) and its harmonics can all contribute to RF currents in a lead and particularly RF currents at a distal electrode-to-tissue interface. Accordingly, the primary frequency and its harmonics can all contribute to leadwire heating.

The bandstop filter 146 can be designed to have resonances at the primary RF frequency (64 MHz) and also at its harmonic frequencies. In general, only harmonics of significant amplitude would require attenuation by the inductive coil-parasitic capacitance bandstop filter 146.

Figure 39:
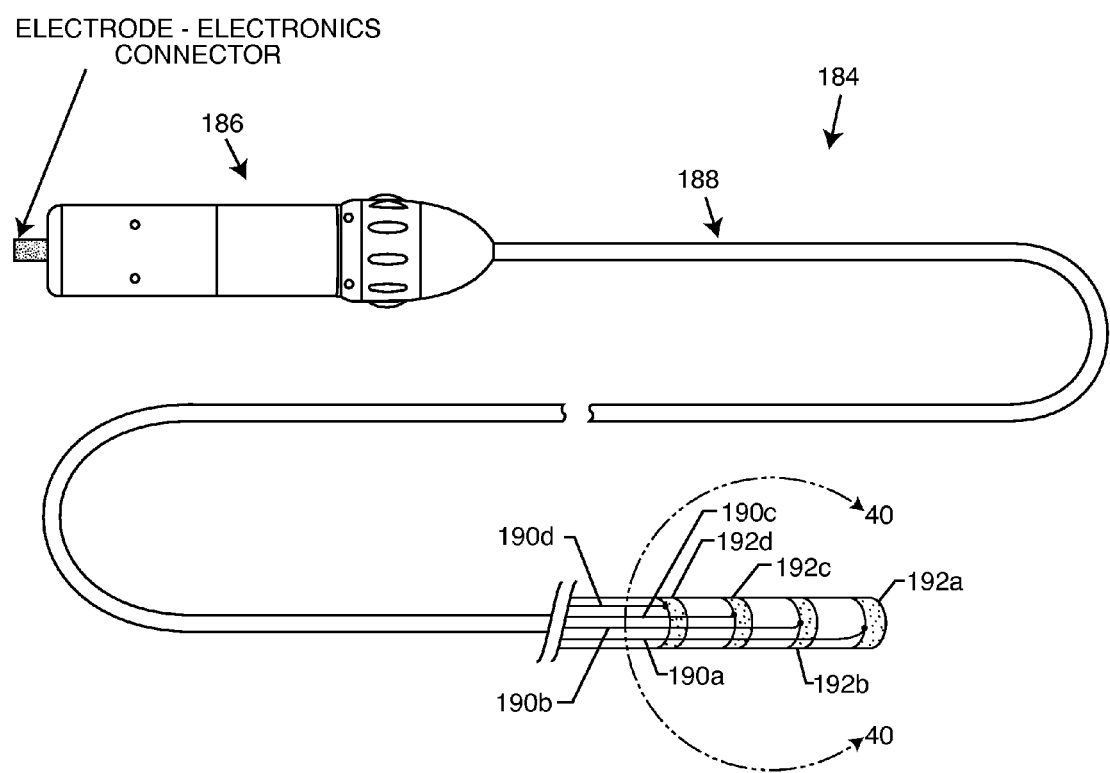
FIG. 39 is a schematic diagram of a prior art probe or catheter showing ablation and sense electrodes.

FIG. 39 is a schematic diagram of a typical probe or catheter 184. Typically, the probe or catheter 184 has a handle or pistol grip 186 connected to a steerable elongated body 188 which includes leadwires 190a-190d. In general, by adjusting the handle 186, the body 188 can be curved through torturous transvenous lead paths. In this case, there are four electrodes shown including ablation electrode 192a, as well as, sense electrodes 192b-192d.

Figure 40:
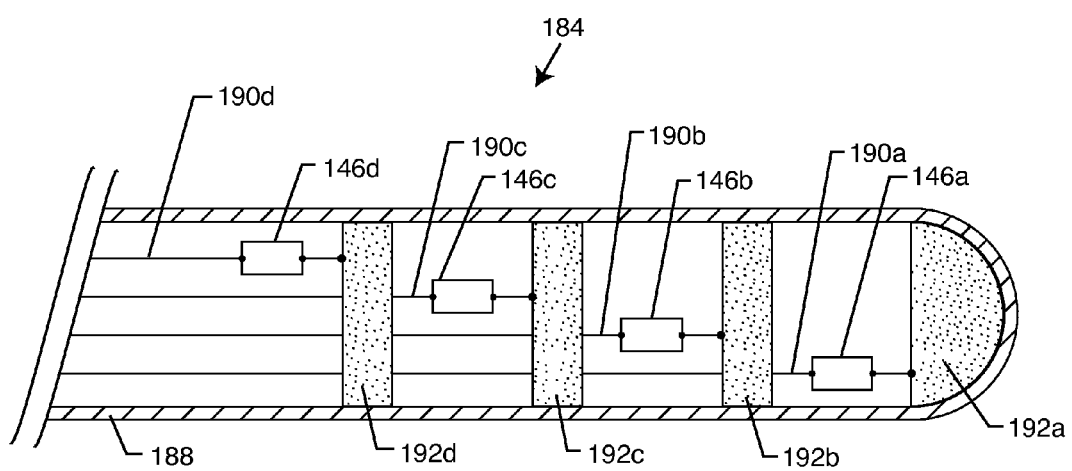
FIG. 40 is taken generally of the area designated by line 40-40 from FIG. 39, and illustrates inductive coil-parasitic capacitance bandstop filters placed in series with each of the electrodes.

FIG. 40 is taken generally of the area designated by line 40-40 from FIG. 39, and illustrates that there is a inductive coil-parasitic capacitance bandstop filter 146a-146d of the present invention in series with each one of the leadwires 190a-190d. As previously described, these inductive coil-parasitic capacitance bandstop filters 146a-146d present a high impedance at the MRI RF pulsed frequency and thereby prevent inadvertent overheating of the distal electrodes 192a-192d. The ablation electrode delivers RF ablation energy only when it's located in a precise location. For example, this precise location could be related to scar tissue formation around atrial pulmonary vein(s) to eliminate atrial fibrillation. Inadvertent electrode heating (from the MRI RF field) is highly undesirable in that scar tissue would occur in unwanted locations. For example, if the sinus node is accidently ablated, the patient would then be pacemaker dependent for the rest of their life.

Figure 41:
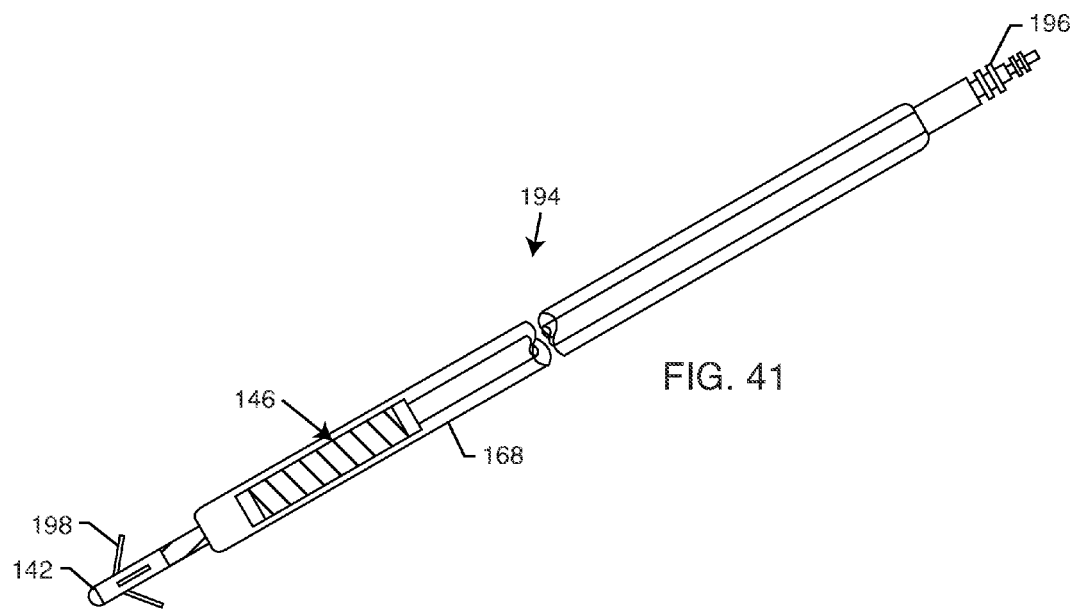
FIG. 41 is an elevational view of a unipolar pacemaker implantable lead having a proximal connector wherein an inductive coil-parasitic capacitance bandstop filter is installed at, near or within the distal electrode.

FIG. 41 illustrates a unipolar pacemaker lead 194 having a proximal connector 196 such as described by International Standards ISO-IS1, DF1, DF4 or IS4. This proximal connector 196 would be plugged into a cardiac pacemaker, a cardioverter defibrillator or the like (not shown). The distal end of the lead has a passive tip electrode 142 with tines 198 which are used to grasp trabecular or other tissue within a human heart. Shown is an inductive coil-parasitic capacitance bandstop filter 146 of the present invention that is located near, at or adjacent to the distal unipolar electrode 142. As previously described, when exposed to an MRI high intensity RF environment, the bandstop filter 146 impedes the undesirable flow of RF currents into body tissues via electrode 142. The lead body has an overall insulation 168 which extends over the inductive coil-parasitic capacitance bandstop filter 146 to a point near the distal electrode 142. This insulation 168 prevents RF currents from circulating through body fluids thereby tending to short out or degrade the impedance of the inductive coil-parasitic capacitance bandstop filter 146. In a preferred embodiment, the overall insulation 168 still provides that the center of the inductive coil-parasitic capacitance bandstop filter 146 can be hollow for convenient guide wire insertion. In addition, the center of the inductive coil-parasitic capacitance bandstop filter 146 could incorporate one or more valves such that additional leads or guide wires placed from the proximal side can be routed and sealed.

Figure 42:
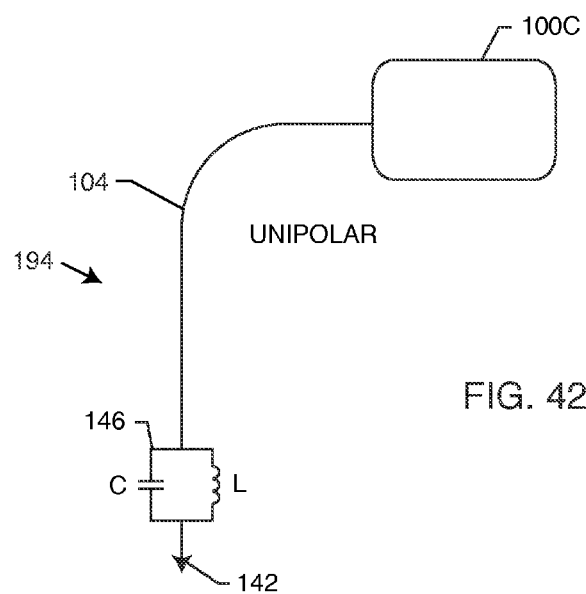
FIG. 42 is a schematic diagram of the unipolar implantable lead of FIG. 41.

FIG. 42 is a schematic diagram of the unipolar lead 194 of FIG. 41 showing the AMD 100C and a inductive coil-parasitic capacitance bandstop filter 146 of the present invention installed preferably at or near the distal tip electrode 142.

Figure 43:
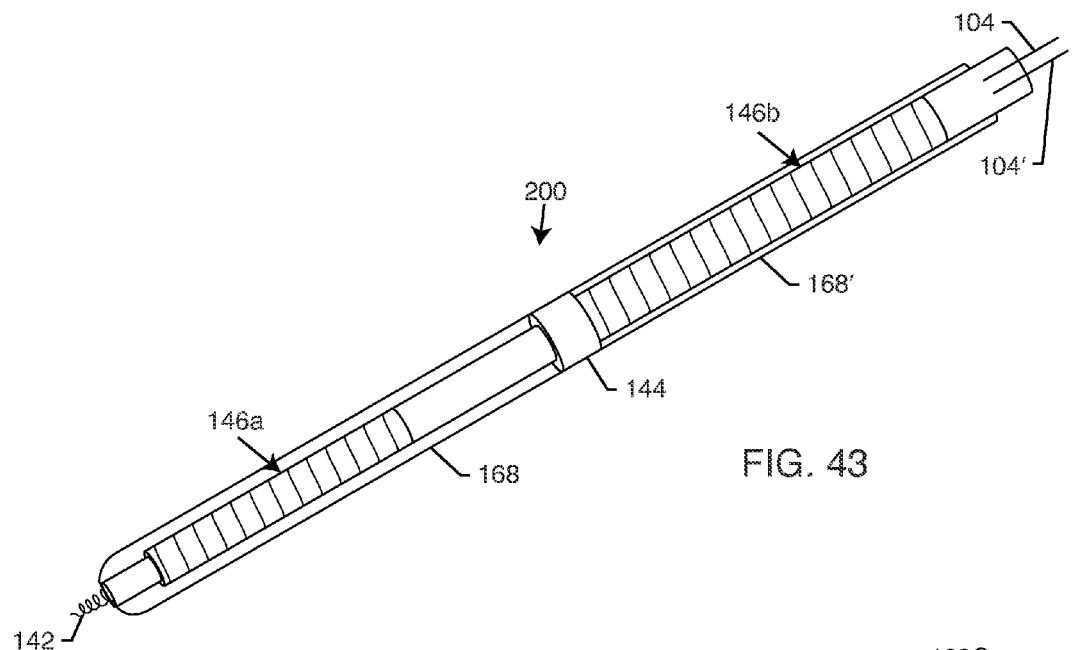
FIG. 43 is a view similar to FIG. 41 except that the inductive coil-parasitic capacitance bandstop filter is associated with both the tip and ring electrodes of a bipolar pacemaker lead.

FIG. 43 is very similar to FIG. 41 except a bi-polar active fixation electrode 200 is shown at the distal end or tip of the implanted lead 104. In this case, the active fixation screw-in helix tip electrode 142 has been extended, which would typically be screwed into cardiac tissue. A ring electrode 144 forms a bi-polar electrode system wherein pacing and sensing can be conducted between the helix tip electrode 142 and the ring electrode 144. There are two lead conductors 104 and 104' which are plugged into the active medical device 100C. There is a inductive coil-parasitic capacitance bandstop filter 146a in series with the active fixation helix electrode 142 and also an optional inductive coil-parasitic capacitance bandstop filter 146b in series with the ring electrode 144. In this way, both the distal helix 142 and ring electrodes 144 would both be prevented from overheating in an MRI environment. Insulation 168 prevents RF currents from flowing through body fluids and shorting out the inductive-parasitic capacitance bandstop filter 146a and insulation material 168' insulates the inductive-parasitic capacitance bandstop filter 146b and performs the same function. In addition, the insulating layer 168 also protects the implanted lead, provides flexibility and lubricity (to ease transvenous lead insertion) and aids in the long-term reliability of the overall lead system.

Figure 44:
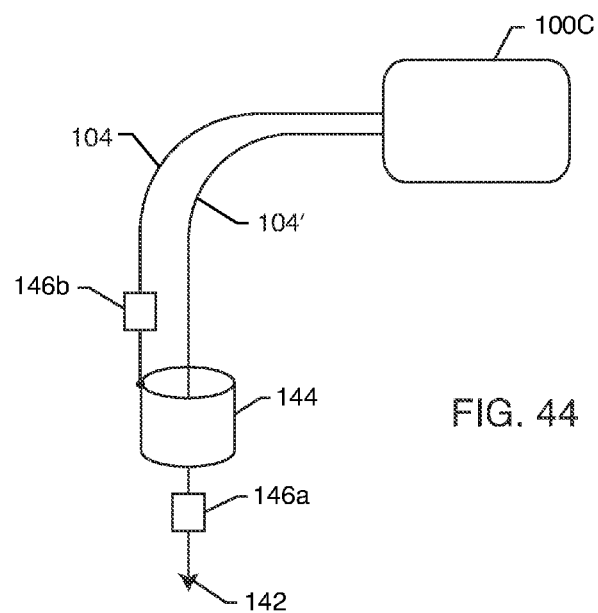
FIG. 44 is a schematic diagram of the bi-polar lead illustrated in FIG. 43.

FIG. 44 is the schematic diagram of the bi-polar lead illustrated in FIG. 43. One can see the active implantable medical device such as a cardiac pacemaker 100C with implanted lead conductors 104 and 104'. Lead conductor 104 is connected in series with a inductive coil-parasitic capacitance bandstop filter 146b to ring electrode 144. Lead conductor 104' has a inductive coil-parasitic capacitance bandstop filter 146a connected in series with active fixation tip electrode 142. As previously described, in preferred embodiments, the inductive coil-parasitic capacitance bandstop filters 146a and 146b are very near, at or within the respective distal electrodes. This prevents RF current induction from MRI fields from coupling around the wave filters and inducing currents in the distal electrodes.

Figure 45:
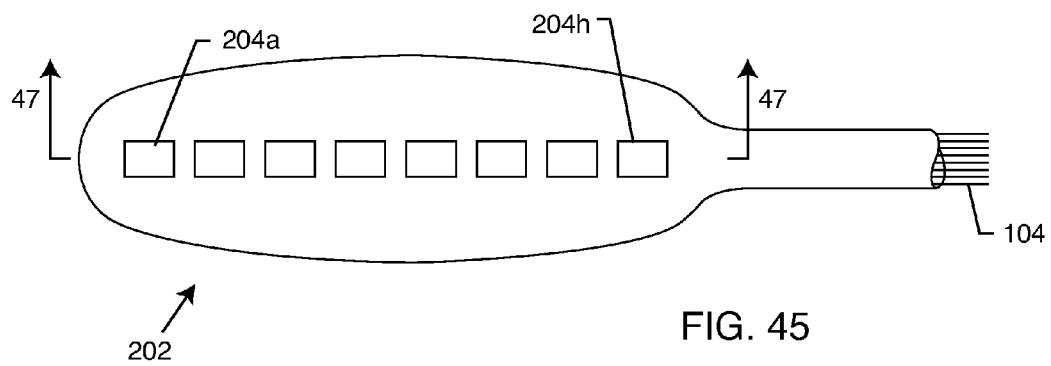
FIG. 45 is an elevational view of an 8-pin neurostimulator paddle electrode.

FIG. 45 illustrates an 8-pin paddle electrode 202 commonly used in neurostimulators such as spinal cord stimulator applications. The eight paddle electrodes are shown as 204a through 204h.

Figure 46:
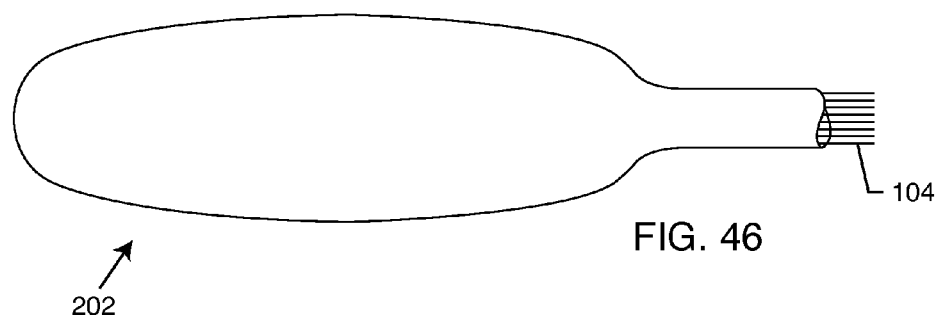
FIG. 46 is an elevational view of the reverse side of the paddle electrode of FIG. 45.

FIG. 46 is the reverse side of the paddle electrode 202 of FIG. 45.

Figure 47:
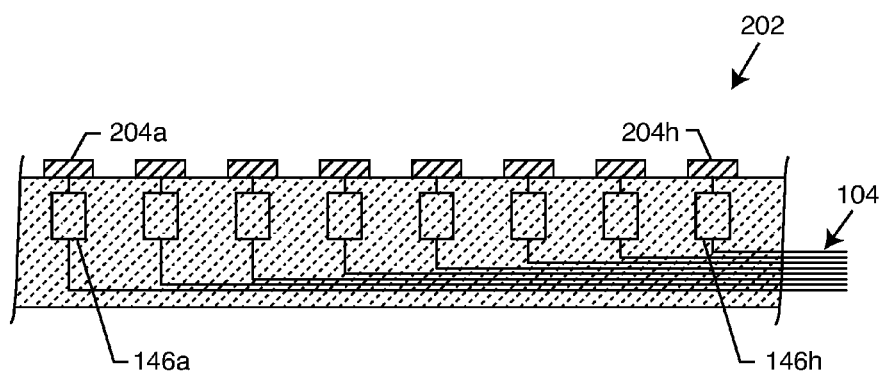
FIG. 47 is an enlarged sectional view taken generally of the area indicated by a line 47-47 from FIG. 45, showing inductive coil-parasitic capacitance bandstop filters in series with each of the electrode conductors.

FIG. 47 is a cross-section taken generally from section 47-47 from FIG. 45. One can see that there is a inductive coil-parasitic capacitance bandstop filter 146 disposed in series with each one of the pad electrodes 204. FIG. 47 is just one electrode array representative example. As used herein, the term electrode includes any type of electrode in contact with body tissue. For example, this includes, but is not limited to, pacemaker electrodes, endocardial electrodes, epicardial electrodes, defibrillator shocking coils, tip electrodes, active fixation electrodes, passive electrodes, ring electrodes, ablation electrodes, deep brain electrodes, nerve cuff electrodes, various types of paddle electrodes, flex cable electrodes, cochlear electrode bundles, Bions, probe/catheter electrodes, skin ECG or EKG electrodes, and the like.

Figure 48:
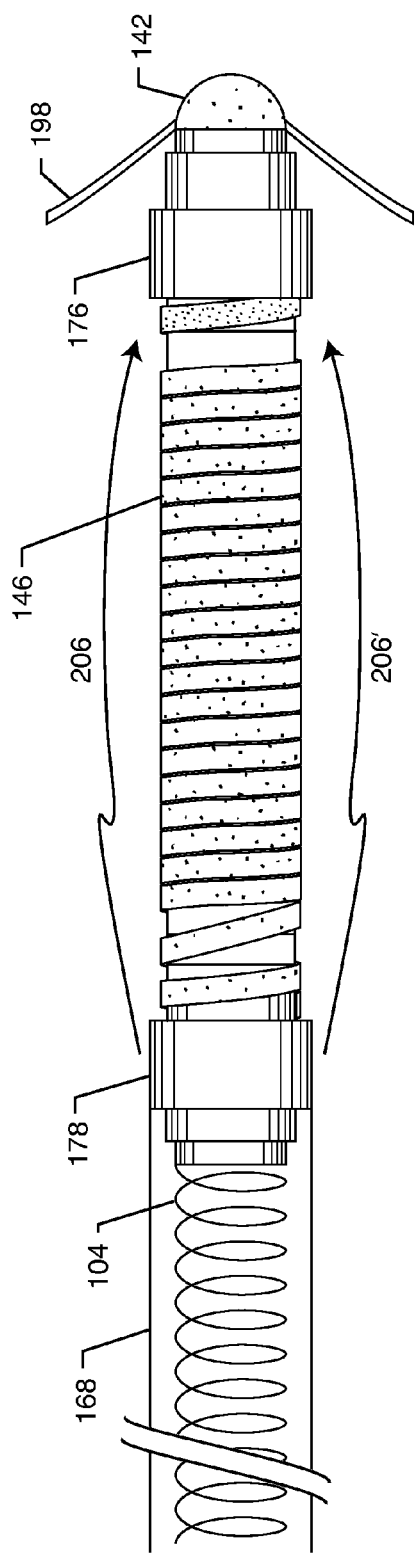
FIG. 48 is an elevational view of the inductive coil-parasitic capacitance bandstop filter of FIG. 35 shown in series with a passive fixation electrode in an implanted lead.

FIG. 48 illustrates the inductive coil-parasitic capacitance bandstop filter 146 with end caps 176 and 178 that were previously illustrated in FIG. 35. End cap 176 is shown attached to the conductor 104 of an implanted lead which has an overall insulation sheath 168. In this case, by way of example, the inductive-parasitic capacitance bandstop filter 146 could present 2000 ohms at its primary resonant frequency of 64 MHz. However, in this configuration, since the inductive coil-parasitic capacitance bandstop filter 146 does not have overall end to end insulation, there are undesirable RF leakage paths 206 and 206' through body tissue (actually, a very large number of leakage paths). The 2000 ohms of impedance desirably impedes the flow of MRI induced RF currents into body tissue through the electrode 142. However, if both ends of the inductive coil-parasitic capacitance bandstop filter 146 are not isolated from each other, parallel paths 206 and 206' result through body fluid (ionic fluid). This parallel path effect as measured by the inventors can be approximately 80 ohms. Referring back to FIG. 48, if an 80 ohms parallel path existed between the end caps 176 and 178, this would seriously degrade the impedance at resonance. The amount of degradation in impedance can result in RF currents flowing through the distal electrode 142 into body tissues that could result in life-threatening overheating of these adjacent tissues.

Figure 49:
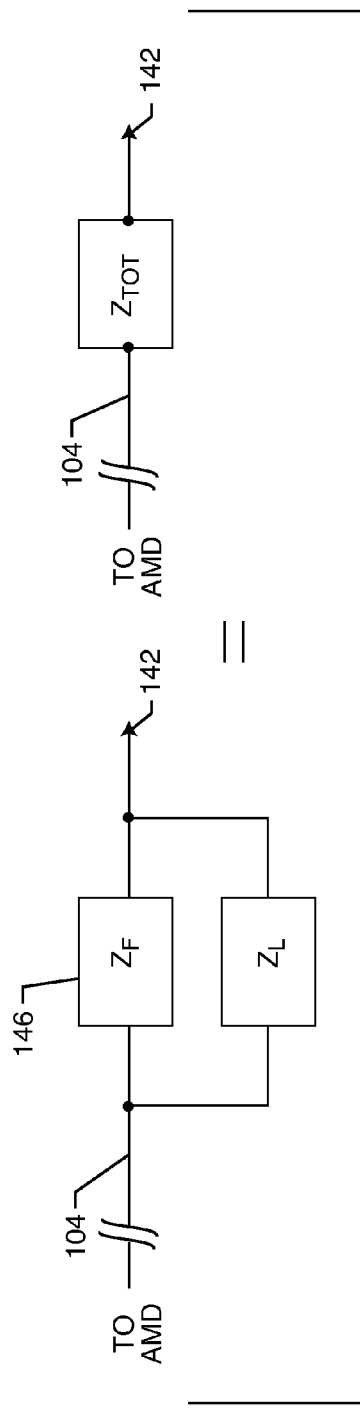
FIG. 49 is a schematic diagram which illustrates undesirable electrical leakage through body fluids in parallel with the inductive coil-parasitic capacitance bandstop filter of FIG. 48.

FIG. 49 is the schematic diagram taken from FIG. 48 showing the 2000-ohm impedance $Z_F$ at resonance of the inductive coil-parasitic capacitance bandstop filter 146. Shown in parallel with the inductive coil-parasitic capacitance bandstop filter 146 is the RF leakage path or 80-ohm impedance of the body tissues $Z_L$. Using the parallel resistance formula, when one has 80 ohms in parallel with 2000 ohms, the result is a combined impedance $Z_{TOT}$ of 76.82 ohms. As one can see, this is a catastrophic reduction of the impedance of the inductive coil-parasitic capacitance bandstop filter 146 at resonance. It is a feature of the present invention that these body fluid paths 206 and 206' be insulated and/or blocked such that they cannot cause leakage in parallel with the inductive coil-parasitic capacitance bandstop filter 146 of the present invention.

Figure 50:
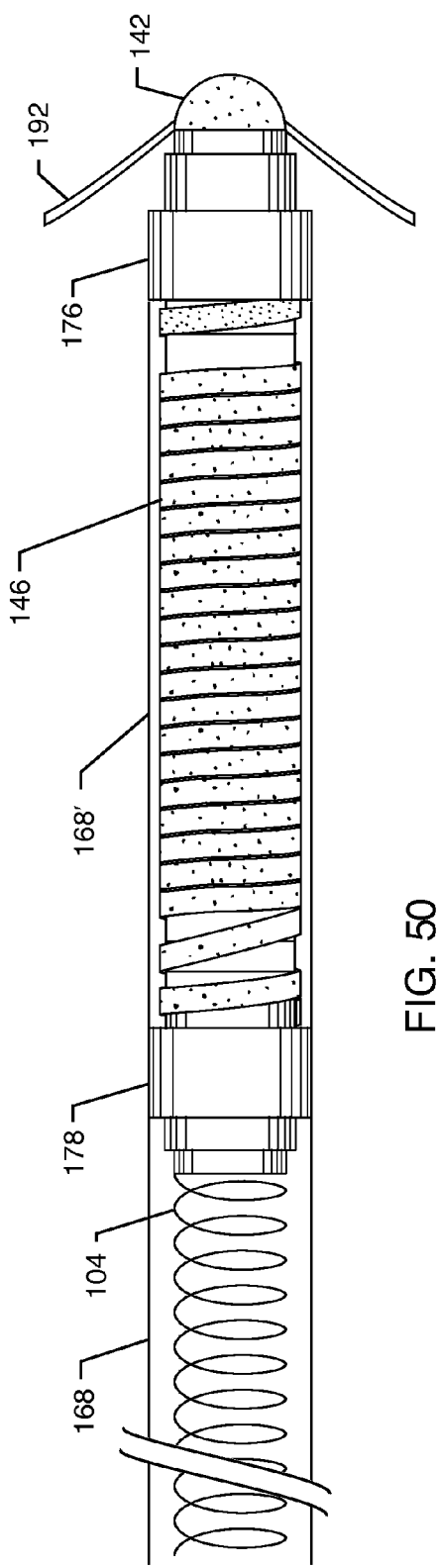
FIG. 50 is an elevational view of the inductive coil-parasitic capacitance bandstop filter of FIG. 48 with electrical insulation disposed over the bandstop filter such that electrical leakage through body fluids is prevented.

FIG. 50 is very similar to FIG. 48 except that the lead insulation 168' has been extended completely over the inductive coil-parasitic capacitance bandstop filter 146 of the present invention. Accordingly, the leakage paths 206 through body fluid or tissues have been eliminated. In this case, the inductive coil-parasitic capacitance bandstop filter 146 of FIG. 50 would present nearly the full 2000 ohms of impedance at the MRI RF-pulsed frequency. It should be noted that no insulation material is perfect. In other words, the insulation material 168' would still allow for a very slight amount of leakage. However, the intention here is that the amount of leakage would be negligible compared to the overall bandstop filter impedance at resonance.

FIG. 51 illustrates an exemplary bipolar active fixation electrode 208 which embodies a lead body 210, a coaxial conductor 104' for the ring electrode 144 and coaxial conductor 104 for the tip (active fixation helix) electrode 142, a collar 212, and a translatable casing 214 which houses the inductive coil-parasitic capacitance bandstop filter 146 of the present invention. The translatable casing 214 includes a pins 216 and 218. The pin 216 is electrically and mechanically connected to the tip electrode lead conductor 104 and the pin 218 is attached to a translatable seal assembly 220 which is also connected to the distal helix electrode 142. The pin 216, the casing 214, the pin 218 and the translatable seal structure 220 all form what is defined herein as a casing subassembly 222. The casing 214 which houses the inductive coil-parasitic capacitance bandstop filter 146 can be hermetically sealed as described in US 2010/0324640 or it can be a rigid or semi-rigid overmolded rigid or semi-rigid non-hermetic subassembly similar to that previously illustrated in FIG. 50.

It is very important that body fluids be prevented from encroaching across the two ends of casing 214 and the inductive coil-parasitic capacitance bandstop filter 146. As previously described, these parallel ionic conduction paths can seriously degrade the impedance of the bandstop filter at resonance.

There will typically be a laser weld (not shown) electrically and mechanically connecting the tip conductor 104 to pin 216. There is also a laser weld 224 connecting pin 218 to a weld sleeve 226 of the translatable seal assembly 220. The weld sleeve 226 may be attached to the pin 218 in any known technique including laser welding, bonding, crimping, adhering, brazing, other forms of welding, or any other suitable method. The weld sleeve 226 is typically laser welded to the helix electrode 142. During transvenous insertion, the active fixation helix tip electrode 142 is retracted (as shown) so that it will not inadvertently stab or poke into body tissues during transvenous lead insertion. When the physician has positioned it in the desirable location (perhaps inside the cardiac right ventricle), then the physician takes a special torque tool and twists the proximal end of lead body 210 tip conductor 104 which causes the entire conductor 104 and casing subassembly 222 to rotate. As the distal helix electrode 142 rotates, it engages a guide 228 which causes the helix 142 to extend and screw into body tissue. The guide 228 may be formed as part of the collar 212 and engages the tip electrode 142 when the tip conductor 104 is rotated. The rotation causes the helical tip electrode 142 to rotate within the collar 212 and thereby translate in a forward manner. At the same time the tip electrode 142 is advancing relative to the collar 212, it is engaging with body tissue by being screwed directly into the tissue forming an attachment. The tip electrode 142 can be rotated in the opposite direction by the tip conductor 104 and thereby disengaged from the tissue for removal and/or reattachment at a different location. This is a method of active affixation which is well known in the art.

A flexible seal 230 slides against the interior of the collar 212 thereby preventing the entrance of ionic body fluids into the inside of the lead body 210. The seal 230 may be bonded, molded, adhered, or formed onto the weld sleeve 226 by any suitable means. The seal 230 can be formed in a multitude of ways, such as multiple wipers, o-rings, thin disks or sheets, and various molded profiles.

There is a secondary optional O-ring seal 232 as shown in FIG. 51. The optional O-ring seal 232 is disposed between the inside diameter of the lead collar 212 and the outside diameter of the translatable casing 214. The purpose of seal 230 and the O-ring seal 232 is to ensure that ionic body fluids cannot be disposed across the important electrical path between pins 216 and 218. Ionic body fluids can represent an undesirable parallel path as low as 80 ohms. Over time, due to bulk permeability, body fluids will eventually penetrate into the interior of the lead body 210. However, this is an osmotic type of action. The resulting fluids that would occur over long periods of time inside the lead body 210 would be distilled and free of ionic contaminants (de-ionized). This means that they would be less conductive of high frequency electrical signals from one end to the other of the inductive coil-parasitic capacitance bandstop filter 146. The presence of optional O-ring 232 is desirable in that it also presents a high impedance to such a parallel circuit path. The casing 214 may also have a conformal insulative coating (not shown) for further electrically isolating terminals 216 and 218 such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 51 may work with or without such coatings. The casing 214 may be a metallic and hermetically container or any biocompatible insulative material.

Referring once again to FIG. 51, in the case where the casing 214 is thermally conductive (such as a thermally conductive metal), it also desirably acts as a heat dissipation shield. The bandstop filter 146 which is enclosed within structure 214 consists of an inductance in parallel with a capacitance. At the frequency of the MRI RF pulsed frequency, the magnetic field of the inductor collapses into the electric field of the capacitor. For example, for a 1.5 Tesla MRI scanner, these currents circulate back and forth between the inductance and the capacitance of the bandstop filter at approximately 64 MHz. Even if the inductor inductance and the capacitance have low parasitic resistive losses, a considerable amount of heat is still built up within the bandstop filter itself. This is why bandstop filters are also known in the prior art as "trap" filters. The energy is literally trapped in the filter which prevents it from going to the distal tip electrode where it could cause undesirable temporary or permanent damage to body tissues. A feature of the present invention is that the bandstop filters can be shielded with a surrounding relatively high surface area thermally conductive material such as a conductive metal in order to dissipate heat energy into surrounding body fluids and tissues. For the relatively large surface area, the amount of temperature rise is quite small compared to when this energy is all concentrated at a distal tip electrode to tissue interface. In a particularly preferred embodiment, the bandstop filter 146 housed within the heat dissipating shield would have a thermally conductive insulative material 168 around it. This would assist in removing heat energy from the bandstop filter and conducting it to the casing 214 where the heat energy can then be dissipated into body fluids and tissues over a relatively large surface area. The heat dissipating shield as illustrated in FIG. 51 is not limited to just active fixation helix electrodes as shown. Heat dissipating shields are also applicable to any bandstop filter associated with an implantable lead and/or distal electrode that is in contact with biological cells or tissues.

Figure 52:
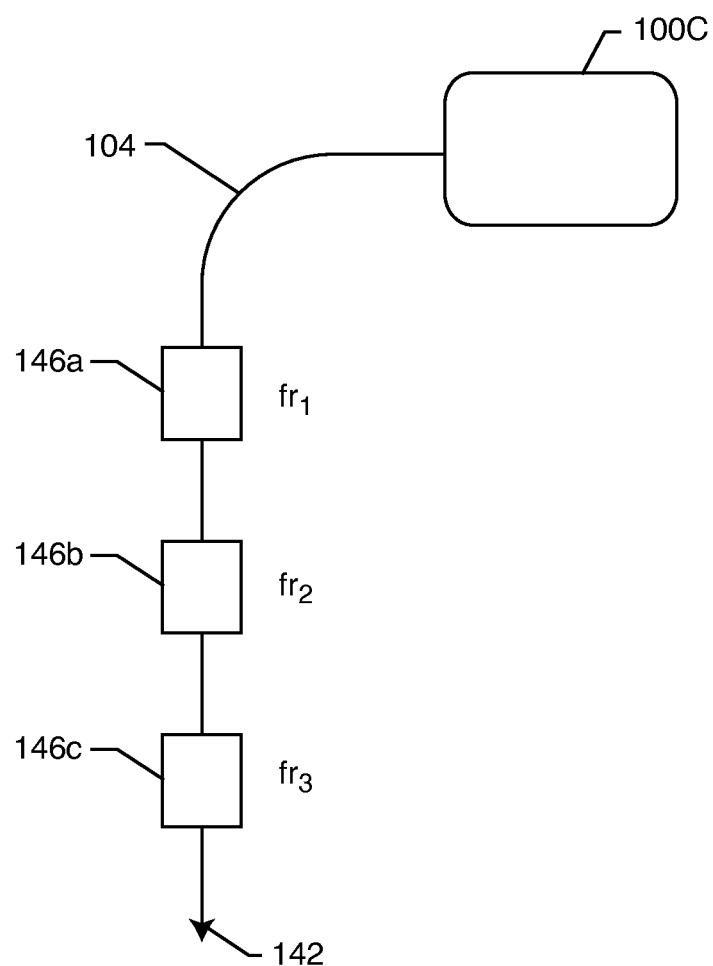
FIG. 52 is a schematic diagram showing that any number of inductive coil-parasitic capacitance bandstop filters may be placed in series anywhere along the length of an implantable lead.

FIG. 52 illustrates that any number of individual or separate discrete inductive coil-parasitic capacitance bandstop filters 146a-146c can be placed in series in any conductor of any implanted lead in multiple locations along the lead length. For example, three different inductive coil-parasitic capacitance bandstop filter (with the same or different resonant frequencies) could be placed in series along the length of an implanted lead 104 as shown. In FIG. 52, there are three different inductive coil-parasitic capacitance bandstop filters that are resonant at $f_{r1}$, $f_{r2}$ and $f_{r3}$; however it will be apparent to those skilled in the art that any number of bandstop filters can be placed in series in an implanted lead. In summary, multiple resonances $fr_1$ and $fr_2$ . . . or $fr_n$ can be created by multiple segments in a single inductive coil-parasitic capacitance bandstop filter or multiple resonances can also be achieved by installing a multiplicity of discrete inductive coil-parasitic capacitance bandstop filter along the length of the lead as shown in FIG. 52.

Figure 53:
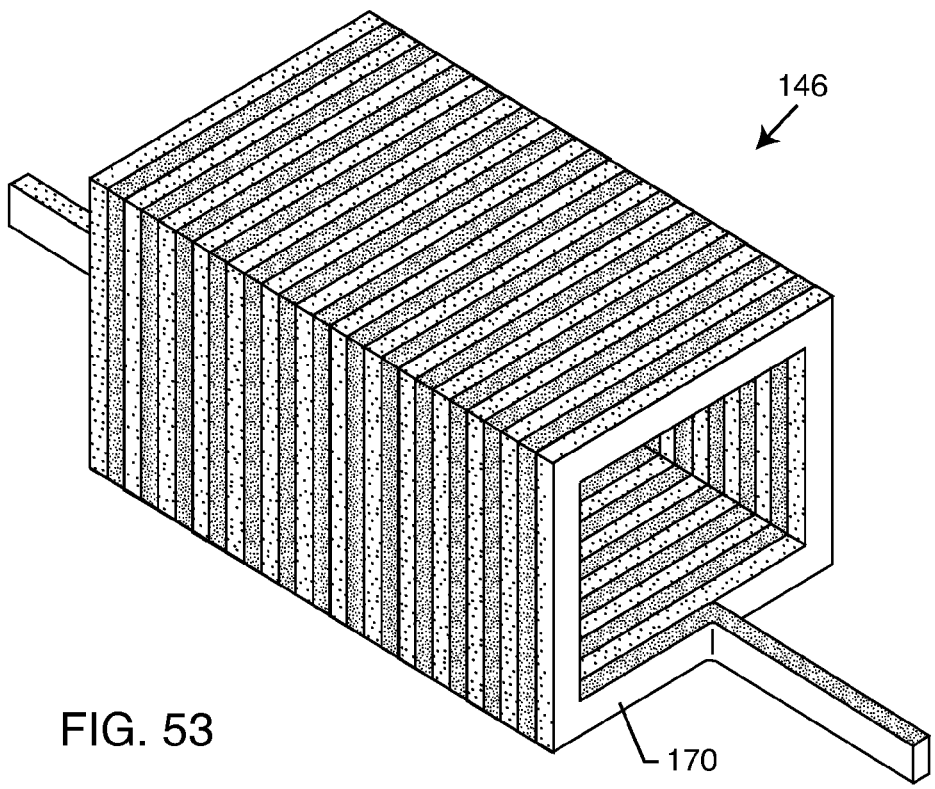
FIG. 53 is an isometric view of an inductive-parasitic capacitance bandstop similar to FIG. 29 except that it has a square cross-section.

FIG. 53 is an inductive-parasitic capacitance bandstop filter as previously illustrated in FIG. 29 except that the cross-sectional area of the inductor is square rather than round.

Figure 54:
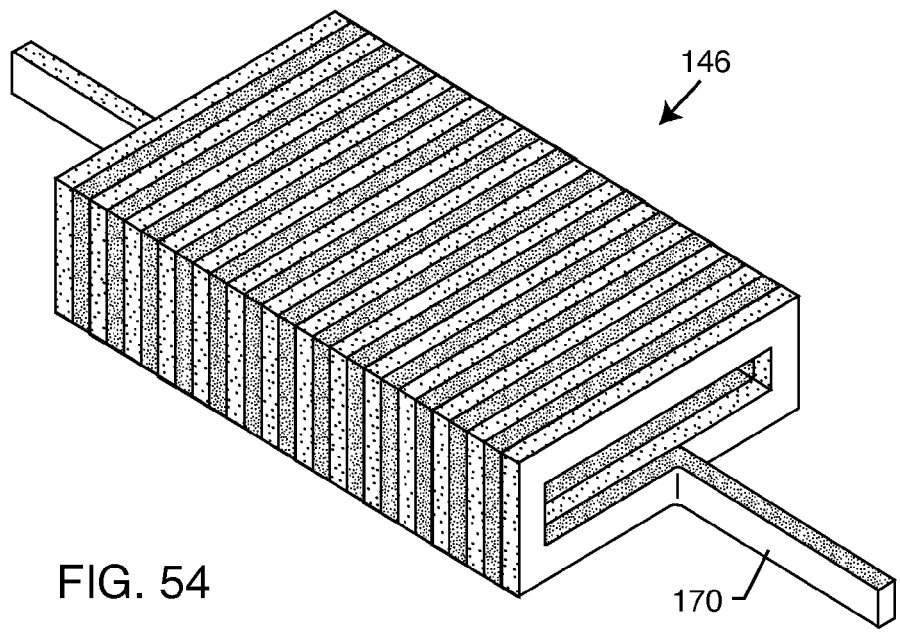
FIG. 54 is an isometric view of an inductive-parasitic capacitance bandstop similar to FIG. 29 except that it has a flattened or rectangular cross-section.

FIG. 54 is the same as FIG. 53, except that the cross-sectional area of the bandstop filter is flat or rectangular.

From the foregoing it will be appreciated that the present invention is broadly directed to a medical diagnostic or therapeutic device which comprises (1) an active medical device including an implantable lead with a conductor extension therefrom and in contact with biological cells, and (2) a bandstop filter associated with the lead conductor, for attenuating current flow through a lead conductor at a selected center frequency or range of frequencies. The bandstop filter comprises, generally, a capacitance in parallel with an inductance. Said parallel capacitance and inductance are placed in series with the lead wire, wherein values of capacitance and inductance are selected such that the bandstop filter is resonant at the selected center frequency or range of frequencies. The bandstop filter has an overall circuit Q wherein the resultant 3 dB bandwidth is at least 10 kHz.

In a particularly preferred form, the inductance is formed as part of a coiled or spiral conductor portion of the implanted lead, and the capacitance is the parasitic capacitance between adjacent turns of the inductance. In this embodiment, the inductance conductor is insulated with a dielectric material. In a particularly preferred form, the range of selected frequencies includes a plurality of MRI RF pulsed frequencies. Bandstop filters are typically disposed at, adjacent to or within a distal electrode of the implantable lead.

Electrical insulation is typically provided for attenuating stray RF currents through body fluids and tissues thereby preventing degradation of the impedance of the bandstop filter resonance. The insulation may be contiguous with an overall insulation of the implantable lead, and may comprise an insulative sleeve which may further form a heat dissipating shield associated with the bandstop filter.

The coiled or spiral conductor of the implantable lead may have separate distinct segments having different cross-sectional areas and/or a different number of turns to form distinct bandstop filters which resonate at different selected center frequencies or ranges of frequencies. In this regard, the coiled or spiral conductor preferably comprises a rectangular or square cross-sectional configuration.

Accordingly, it will be appreciated that the inductance may be inherently derived from the lead's material of construction or structure. Similarly, the capacitance may also be inherently derived from the lead's material of construction or structure.

Although several particular embodiments of the invention have been described in detail for purposes of illustration, various modifications of each may be made without departing from the spirit and scope of the invention. Accordingly, the invention is not to be limited, except as by the appended claims.

The invention claimed is:

1. An implantable medical lead, comprising:
a) an implantable lead conductor extending from a proximal conductor end to a distal conductor portion having a distal conductor end, wherein the proximal conductor end is electrically connectable to an active implantable medical device;
b) a mandrel comprising an intermediate mandrel body extending from a proximal mandrel end cap to a distal mandrel end cap, wherein the proximal and distal mandrel ends are electrically conductive;
c) a self-resonant inductor comprising at least a portion of the lead conductor formed as a coiled inductor contacted with a dielectric material, wherein the coiled inductor contacted with the dielectric material is wrapped around the mandrel body from adjacent to the proximal mandrel end cap to adjacent to the distal mandrel end cap;
d) at least one electrode electrically connected to the distal conductor portion or the distal conductor end, wherein the electrode is contactable with biological cells; and
e) an insulation material extending from at least a first outer surface of the proximal mandrel end cap to a second outer surface of the distal mandrel end cap and covering at least an outer surface of the dielectric material contacting the coiled inductor to thereby prevent RF currents in body fluids and tissues from flowing from and to the proximal and distal mandrel ends by isolating both ends of the self-resonant inductor, which currents would otherwise degrade an impedance at resonance of the self-resonant inductor,
f) wherein the self-resonant inductor has a parasitic capacitance between adjacent turns of the coiled inductor to thereby provide an equivalent circuit comprising an inductance in parallel with the parasitic capacitance,
g) wherein the parasitic capacitance provides a capacitive series resistance ($R_C$) and the self-resonant inductor has an inductance and an inductor series resistance ($R_L$), wherein at low frequencies of about 10 Hz to about 1 kHz an inductive reactance and the inductor series resistance ($R_L$) permit passage of biological signals from the electrode to the proximal lead conductor end while a capacitive reactance and the capacitive series resistance ($R_C$) substantially act as an open circuit to the same biological signals that the self-resonant inductor allows to pass,
h) wherein the self-resonant inductor is resonant at or near an RF frequency, thereby providing a high impedance in series with the lead conductor at or near the RF frequency, and
i) wherein the self-resonant inductor has an overall circuit Q so that the resultant 3-dB bandwidth is at least 100 kHz.

2. The lead of claim 1 wherein the resultant 3-dB bandwidth is on the order of megahertz and at least 0.5 MHz.

3. The lead of claim 1 wherein the resultant 3-dB bandwidth is on the order of MHz and is at least 10 MHz.

4. The lead of claim 1 wherein each of the dielectric material and the insulation material is selected from the group consisting of polyimide, aromatic polyimide, liquid crystal polymer, PTFE, PEEK, ETFE, Parylene, tantalum oxides, iridium oxides, niobium oxides, hafnium oxides, ruthenium oxides, $SiO_2$, $Si_3N_4$, $Al_2O_3$, $Y_2O_3$, $La_2O_3$, $Ta_2O_5$, $TiO_2$, $HfO_2$, $ZrO_2$, PFA, FEP, Polyurethane, polyamide, polyvinyl acetal, polyvinyl acetal overcoated with polyamide, polyurethane overcoated with polyamide, epoxy, polyester (amide) (imide) overcoated with polyamide, polyester (amide) (imide), silicone-treated glass fiber, polyamide-imide, polyvinylchloride (PVC), polylefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PEA, Halar ECTFE, XLPE, XLPVC, silicone rubber, Polyimide Kapton film, Polyester Mylar film, Kaladex PEN film, and a crosslinked polyalkene.

5. The lead of claim 1 wherein each of the dielectric material and the insulation material has a dielectric constant greater than 1 up to 100.

6. The lead of claim 1, wherein a $Q_i$ of the self-resonant inductor is relatively high and a $Q_c$ of the capacitance is relatively low.

7. The lead of claim 1, wherein a $Q_i$ of the self-resonant inductor is relatively low and a $Q_c$ of the capacitance is relatively high.

8. The lead of claim 1, wherein the Q of the self-resonant inductor results in a 3-dB bandwidth that spans a plurality of MRI RF pulsed frequencies.

9. The lead of claim 1 wherein the self-resonant inductor is disposed at, adjacent to, or within the electrode.

10. The lead of claim 1, wherein the self-resonant inductor is integrated into the electrode comprising either a pacemaker Tip electrode or a pacemaker Ring electrode.

11. The lead of claim 1, wherein the self-resonant inductor is at least partially housed within a heat dissipating shield.

12. The lead of claim 1, wherein at least one of the dielectric material and the insulation material is provided with a thermally conductive material.

13. The lead of claim 1, wherein the proximal and distal mandrel ends are provided as conductive end caps.

14. The lead of claim 1, wherein a shape of the lead conductor comprising the coiled inductor is of a rectangular or square cross-sectional configuration.

15. The lead of claim 1, wherein the self-resonant inductor resonates at a center frequency and at one or more of its harmonic frequencies.

16. The lead of claim 1 wherein the insulation material is contiguous with an insulation of the implantable lead conductor.

17. The lead of claim 1 wherein the insulation material comprises an insulative sleeve disposed about the coiled inductor portion of the implantable lead conductor.

18. The lead of claim 1, wherein the coiled inductor portion of the lead conductor includes distinct segments having different numbers of turns contacted with a respective dielectric material to form distinct self-resonant inductors which resonate at different center frequencies or across different ranges of frequencies.

19. The lead of claim 1 wherein the intermediate mandrel body has a first diameter that is less than second and third diameters of the respective proximal and distal ends to thereby provide the mandrel having first and second steps formed from a third outer surface of the intermediate body to the first and second outer surfaces of the respective proximal and distal ends and wherein the insulation material substantially covers the first and second outer surfaces of the proximal and distal ends with the coiled inductor comprising the self-resonant inductor residing in a recess of the mandrel provided by the first and second steps.

20. The lead of claim 1 wherein the mandrel has a hollow lumen extending from the proximal mandrel end cap to the distal mandrel end cap.

21. An implantable lead, comprising:
a) an implantable conductor extending from a proximal conductor end to a distal conductor portion having a distal conductor end, wherein the proximal conductor end is electrically connectable to an active implantable medical device;
b) a mandrel comprising an intermediate mandrel body extending from a proximal mandrel end cap to a distal mandrel end cap, wherein the proximal and distal mandrel ends are electrically conductive;
c) a self-resonant inductor comprising at least a portion of the lead conductor formed as a coiled inductor contacted with a dielectric material, wherein the coiled inductor contacted with the dielectric material is wrapped around the mandrel body from adjacent to the proximal mandrel end cap to adjacent to the distal mandrel end cap;
d) at least one electrode electrically connected to the distal conductor portion or the distal conductor end, wherein the electrode is contactable with biological cells; and
e) an insulation material extending from at least a first outer surface of the proximal mandrel end cap to a second outer surface of the distal mandrel end cap and covering at least an outer surface of the dielectric material contacting the coiled inductor to thereby prevent RF currents in body fluids and tissues from flowing from and to the proximal and distal mandrel ends by isolating both ends of the self-resonant inductor, which currents would otherwise degrade an impedance at resonance of the self-resonant inductor,
f) wherein the self-resonant inductor has a parasitic capacitance between adjacent turns of the coiled inductor to thereby provide an equivalent circuit comprising an inductance in parallel with the parasitic capacitance,
g) wherein the parasitic capacitance provides a capacitive series resistance ($R_C$) and the self-resonant inductor has an inductance and an inductor series resistance ($R_L$), wherein at low frequencies of about 10 Hz to about 1 kHz an inductor reactance and the inductor series resistance ($R_L$) permit passage of biological signals from the electrode to the proximal lead conductor end while a capacitive reactance and the capacitive series resistance ($R_C$) substantially act as an open circuit to the same biological signals that the self-resonant inductor allows to pass,
h) wherein the self-resonant inductor is resonant at or near an RF frequency, thereby providing a high impedance in series with the lead conductor at or near the RF frequency, and
i) wherein the self-resonant inductor has an overall circuit Q, wherein the resultant 3-dB bandwidth is at least 10 kHz and the resultant 10-dB bandwidth is at least 25 kHz.

22. The lead of claim 21 wherein the 3-dB bandwidth is on the order of megahertz and at least 0.5 MHz.

23. The lead of claim 21 wherein the 10-dB bandwidth is on the order of MHz and at least 0.5 MHz.

24. The lead of claim 21 wherein each of the dielectric material and the insulation material is selected from the group consisting of polyimide, aromatic polyimide, liquid crystal polymer, PTFE, PEEK, ETFE, Parylene, tantalum oxides, iridium oxides, niobium oxides, hafnium oxides, ruthenium oxides, $SiO_2$, $Si_3N_4$, $Al_2O_3$, $Y_2O_3$, $La_2O_3$, $Ta_2O_5$, $TiO_2$, $HfO_2$, $ZrO_2$, PFA, FEP, Polyurethane, polyamide, polyvinyl acetal, polyvinyl acetal overcoated with polyamide, polyurethane overcoated with polyamide, epoxy, polyester (amide) imide) overcoated with polyamide, polyester (amide) (imide), silicone-treated glass fiber, polyamide-imide, polyvinylchloride (PVC), polyolefin class: {LDPE, HDPE, TPO, TPR, polyolefin alloys}, LDPE low density, HDPE high density, polypropylene (PP), thermoplastic fluoropolymers, TEFLON FEP, Tefzel ETFE, Kynar PVDF, TEFLON PEA, Halar ECTFE, XLPE, XLPVC, silicone rubber, Polyimide Kapton film, Polyester Mylar film, Kaladex PEN film, and a crosslinked polyalkene.

25. The lead of claim 21 wherein the Q of the self-resonant inductor results in a 3-dB bandwidth that spans a plurality of MRI RE pulsed frequencies.

26. The lead of claim 21 wherein the self-resonant inductor is at least partially housed within a heat dissipating shield.

27. The lead of claim 21 wherein the insulation material is a thermally conductive material.

28. The lead of claim 21 wherein a shape of the lead conductor comprising the coiled inductor is of a rectangular or square cross-sectional configuration.

29. The lead of claim 21 wherein the self-resonant inductor resonates at a center frequency and at one or more of its harmonic frequencies.

30. The lead of claim 21 wherein the coiled inductor portion of the lead conductor includes distinct segments having different numbers of turns contacted with a respective dielectric material to form distinct self-resonant inductors which resonate at different center frequencies or across different ranges of frequencies.

31. The lead of claim 21 wherein each of the dielectric material and the insulation material has a dielectric constant greater than 1 up to 100.

32. The lead of claim 21 wherein the intermediate mandrel body has a first diameter that is less than second and third diameters of the respective proximal and distal ends to thereby provide the mandrel having first and second steps formed from a third outer surface of the intermediate body to the first and second outer surfaces of the respective proximal and distal ends and wherein the insulation material substantially covers the first and second outer surfaces of the proximal and distal ends with the coiled inductor comprising the self-resonant inductor residing in a recess of the mandrel provided by the first and second steps.

33. The lead of claim 21 wherein the mandrel has a hollow lumen extending from the proximal mandrel end cap to the distal mandrel end cap.

34. An implantable medical lead, comprising:
a) an implantable lead conductor extending from a proximal conductor end to a distal conductor portion having a distal conductor end, wherein the proximal conductor end is electrically connectable to an active implantable medical device;
b) a mandrel comprising an intermediate mandrel body extending from a proximal mandrel end cap to a distal mandrel end cap, wherein the proximal and distal mandrel ends are electrically conductive;
c) a self-resonant inductor comprising at least a portion of the lead conductor formed as a coiled inductor contacted with a dielectric material, wherein the coiled inductor contacted with the dielectric material is wrapped around the mandrel body from adjacent to the proximal mandrel end cap to adjacent to the distal mandrel end cap;
d) at least one electrode electrically connected to the distal conductor portion or the distal conductor end, wherein the electrode is contactable with biological cells;
e) an insulation material extending from at least a first outer surface of the proximal mandrel end cap to a second outer surface of the distal mandrel end cap and covering at least an outer surface of the dielectric material contacting the coiled inductor to thereby prevent RF currents in body fluids and tissues from flowing from and to the proximal and distal mandrel ends by isolating both ends of the self-resonant inductor, which currents would otherwise degrade an impedance at resonance of the self-resonant inductor,
f) wherein the self-resonant inductor has a parasitic capacitance between adjacent turns of the coiled inductor to thereby provide an equivalent circuit comprising an inductance in parallel with the parasitic capacitance,
g) wherein the parasitic capacitance provides a capacitive series resistance ($R_C$) and the self-resonant inductor has an inductance and an inductor series resistance ($R_L$), wherein at low frequencies of about 10 Hz to about 1 kHz an inductor reactance and the inductor series resistance ($R_L$) permit passage of biological signals from the electrode to the proximal lead conductor end while a capacitive reactance and the capacitive series resistance ($R_C$) substantially act as an open circuit to the same biological signals that the self-resonant inductor allows to pass,
h) wherein the self-resonant inductor is resonant at or near an RF frequency, thereby providing a high impedance in series with the lead conductor at or near the RF frequency, and
i) wherein the self-resonant inductor has an overall circuit Q so that the resultant 3-dB bandwidth is at least 0.5 MHz and the 10-dB bandwidth is at least 0.5 MHz.

35. The lead of claim 34 wherein each of the dielectric material and the insulation material has a dielectric constant greater than 1 up to 100.

36. The lead of claim 34 wherein the Q of the self-resonant inductor resulting in a 3-dB bandwidth that spans a plurality of MRI RF pulsed frequencies.

37. The lead of claim 34 wherein a shape of the lead conductor comprising the coiled inductor is of a rectangular or square cross-sectional configuration.

38. The lead of claim 34 wherein the self-resonant inductor resonates at a center frequency and at one or more of its harmonic frequencies.

39. The lead of claim 34 wherein the coiled inductor portion of the lead conductor includes distinct segments having different numbers of turns contacted with a respective dielectric material to form distinct self-resonant inductors which resonate at different center frequencies or across different ranges of frequencies.

40. The lead of claim 34 wherein the self-resonant inductor is at least partially housed within a heat dissipating shield.

41. The lead of claim 34 wherein each of the dielectric material and the insulation material has a dielectric constant greater than 1 up to 100.

42. The lead of claim 34 wherein the intermediate mandrel body has a first diameter that is less than second and third diameters of the respective proximal and distal ends to thereby provide the mandrel having first and second steps formed from a third outer surface of the intermediate body to the first and second outer surfaces of the respective proximal and distal ends and wherein the insulation material substantially covers the first and second outer surfaces of the proximal and distal ends with the coiled inductor comprising the self-resonant inductor residing in a recess of the mandrel provided by the first and second steps.

43. The lead of claim 34 wherein the mandrel has a hollow lumen extending from the proximal mandrel end cap to the distal mandrel end cap.

44. An implantable lead, probe or catheter, comprising:
a) a conductor extending from a proximal conductor end to a distal conductor portion having a distal conductor end;
b) a mandrel comprising an intermediate mandrel body extending from a proximal mandrel end cap to a distal mandrel end cap, wherein the proximal and distal mandrel ends are electrically conductive;
c) a self-resonant inductor comprising at least a portion of the lead conductor formed as a coiled inductor contacted with a dielectric material, wherein the coiled inductor contacted with the dielectric material is wrapped around the mandrel body from adjacent to the proximal mandrel end cap to adjacent to the distal mandrel end cap;
d) at least one electrode electrically connected to the lead conductor at the distal conductor portion or the distal conductor end, wherein the electrode is configured for placement in contact with biological cells; and d) an insulation material extending from at least a first outer surface of the proximal mandrel end cap to a second outer surface of the distal mandrel end cap and covering at least an outer surface of the dielectric material contacting the coiled inductor to thereby prevent RF currents in body fluids and tissues from flowing from and to the proximal and distal mandrel ends by isolating both ends of the self-resonant inductor, which currents would otherwise degrade an impedance at resonance of the self-resonant inductor, e) wherein the self-resonant inductor has a parasitic capacitance between adjacent turns of the coiled inductor to thereby provide an equivalent circuit comprising an inductance in parallel with the parasitic capacitance, f) wherein the parasitic capacitance provides a capacitive series resistance ($R_C$) and the self-resonant inductor has an inductance and an inductor series resistance ($R_L$), wherein at low frequencies of about 10 Hz to about 1 kHz an inductor reactance and the inductor series resistance ($R_L$) permit passage of biological signals from the electrode to the proximal lead conductor end while a capacitive reactance and the capacitive series resistance ($R_C$) substantially act as an open circuit to the same biological signals that the self-resonant inductor allows to pass, g) wherein the self-resonant inductor is resonant at or near an RF frequency, thereby providing a high impedance in series with the lead conductor at or near the RF frequency, and h) wherein the self-resonant inductor has an overall circuit Q so that the resultant 3-dB bandwidth is at least 100 kHz.

45. The lead of claim 44 wherein the intermediate mandrel body has a first diameter that is less than second and third diameters of the respective proximal and distal ends to thereby provide the mandrel, having first and second steps formed from a third outer surface of the intermediate body to the first and second outer surfaces of the respective proximal and distal ends and wherein the insulation material substantially covers the first and second outer surfaces of the proximal and distal ends with the coiled inductor comprising the self-resonant inductor residing in a recess of the mandrel provided by the first and second steps.

46. The lead of claim 44 wherein the mandrel has a hollow lumen extending from the proximal mandrel end cap to the distal mandrel end cap.

* * * * *

UNITED STATES PATENT AND TRADEMARK OFFICE
CERTIFICATE OF CORRECTION

| | |
|---|---|
| PATENT NO. | : 8,903,505 B2 |
| APPLICATION NO. | : 13/276484 |
| DATED | : December 2, 2014 |
| INVENTOR(S) | : Robert A. Stevenson et al. |

It is certified that error appears in the above-identified patent and that said Letters Patent is hereby corrected as shown below:

On The Title Page,

Page 4, Column 1, (56) References Cited OTHER PUBLICATIONS, line 1 of 3rd reference, delete "Properies" and insert --Properties--

Page 4, Column 1, (56) References Cited OTHER PUBLICATIONS, line 2 of 3rd reference, delete "Tssues" and insert --Tissues--

Page 4, Column 1, (56) References Cited OTHER PUBLICATIONS, line 1 of 5th reference, delete "Constatine" and insert --Constantine--

Page 4, Column 2, (56) References Cited OTHER PUBLICATIONS, line 4 of 4th reference, delete "INternational" and insert --International--

Page 4, Column 2, (56) References Cited OTHER PUBLICATIONS, line 3 of 7th reference, delete "Defibriallators" and insert --Defibrillators--

In The Drawings,

Sheet 11 of 27, Figure 24 item 100I delete "DEFRIBILLATOR" and insert --DEFIBRILLATOR--

Sheet 11 of 27, Figure 25, at the left side of the figure in the lower phrase description beneath the words "FIG. 25" delete "DEFRIBILLATION" and insert --DEFIBRILLATION--

In The Claims,

Column 39, line 64 (Claim 1, line 10) delete "ends" and insert --end caps--

Column 40, line 14 (Claim 1, line 26) delete "ends" and insert --end caps--

Signed and Sealed this
Seventeenth Day of May, 2016

Michelle K. Lee
*Director of the United States Patent and Trademark Office*

CERTIFICATE OF CORRECTION (continued)
U.S. Pat. No. 8,903,505 B2

Column 40, line 55 (Claim 4, line 12) delete "polylefin" and insert --polyolefin--

Column 40, line 58 (Claim 4, line 15) delete "PEA" and insert --PFA--

Column 41, line 18 (Claim 13, line 2) delete "ends" and insert --end caps--

Column 41, line 40 (Claim 19, line 3) delete "ends" and insert --end caps--

Column 41, line 44 (Claim 19, line 7) delete "ends" and insert --end caps--

Column 41, line 46 (Claim 19, line 9) delete "ends" and insert --end caps--

Column 41, line 61 (Claim 21, line 10) delete "ends" and insert --end caps--

Column 42, line 11 (Claim 21, line 26) delete "ends" and insert --end caps--

Column 42, line 54 (Claim 24, line 12) delete "polylefin" and insert --polyolefin--

Column 42, line 57 (Claim 24, line 15) delete "PEA" and insert --PFA--

Column 42, line 63 (Claim 25, line 3) delete "RE" and insert --RF--

Column 43, line 18 (Claim 32, line 3) delete "ends" and insert --end caps--

Column 43, line 22 (Claim 32, line 7) delete "ends" and insert --end caps--

Column 43, line 24 (Claim 32, line 9) delete "ends" and insert --end caps--

Column 43, line 39 (Claim 34, line 10) delete "ends" and insert --end caps--

Column 43, line 55 (Claim 34, line 26) delete "ends" and insert --end caps--

Column 44, line 39 (Claim 42, line 3) delete "ends" and insert --end caps--

Column 44, line 43 (Claim 42, line 7) delete "ends" and insert --end caps--

Column 44, line 45 (Claim 42, line 9) delete "ends" and insert --end caps--

Column 44, line 57 (Claim 44, line 7) delete "ends" and insert --end caps--

Column 45, line 1 (Claim 44, line 18) delete "d)" and insert --e)--

Column 45, line 7 (Claim 44, line 24) delete "ends" and insert --end caps--

Column 45, line 11 (Claim 44, line 28) delete "e)" and insert --f)--

CERTIFICATE OF CORRECTION (continued)
U.S. Pat. No. 8,903,505 B2

Column 45, line 14 (Claim 44, line 32) delete "f)" and insert --g)--

Column 46, line 1 (Claim 44, line 44) delete "g)" and insert --h)--

Column 46, line 5 (Claim 44, line 48) delete "h)" and insert --i)--

Column 46, line 11 (Claim 45, line 3) delete "ends" and insert --end caps--

Column 46, line 12 (Claim 45, line 4) after the word "mandrel" delete the ","

Column 46, line 15 (Claim 45, line 7) delete "ends" and insert --end caps--

Column 46, line 17 (Claim 45, line 9) delete "ends" and insert --end caps--